(12) United States Patent
Claremon et al.

(10) Patent No.: US 8,680,281 B2
(45) Date of Patent: Mar. 25, 2014

(54) LACTAM INHIBITORS OF 11-β-HYDROXYSTEROID DEHYDROGENASE 1

(75) Inventors: David A. Claremon, Maple Glenn, PA (US); Linghang Zhuang, Chalfont, PA (US); Yuanjie Ye, Ambler, PA (US); Suresh B. Singh, Kendall Park, NJ (US); Colin M. Tice, Ambler, PA (US); Zhenrong Xu, Chalfont, PA (US); Robert D. Simpson, Wilmington, DE (US)

(73) Assignees: Vitae Pharmaceuticals, Inc., Fort Washington, PA (US); Boehringer Ingelheim International GmbH (DE)

( * ) Notice: Subject to any disclaimer, the term of this patent is extended or adjusted under 35 U.S.C. 154(b) by 675 days.

(21) Appl. No.: 12/811,577

(22) PCT Filed: Jan. 7, 2009

(86) PCT No.: PCT/US2009/000057
§ 371 (c)(1),
(2), (4) Date: Jan. 11, 2011

(87) PCT Pub. No.: WO2009/088997
PCT Pub. Date: Jul. 16, 2009

(65) Prior Publication Data
US 2011/0098320 A1    Apr. 28, 2011

Related U.S. Application Data

(60) Provisional application No. 61/010,300, filed on Jan. 7, 2008.

(51) Int. Cl.
*C07D 211/40* (2006.01)
*A61K 31/445* (2006.01)

(52) U.S. Cl.
USPC .......................... 546/216; 514/318

(58) Field of Classification Search
USPC ......................... 546/216; 514/318
See application file for complete search history.

(56) References Cited

U.S. PATENT DOCUMENTS

| | | |
|---|---|---|
| 3,341,538 A | 9/1967 | Fred et al. |
| 3,378,587 A | 4/1968 | Reinhardt |
| 3,681,349 A | 8/1972 | Schwan et al. |
| 3,703,529 A | 11/1972 | Frederick et al. |
| 3,919,047 A | 11/1975 | Vidic et al. |
| 4,009,171 A | 2/1977 | Albertson |
| 4,043,927 A | 8/1977 | Duling et al. |
| 4,108,857 A | 8/1978 | Albertson |
| 4,136,145 A | 1/1979 | Fuchs et al. |
| 4,136,162 A | 1/1979 | Fuchs et al. |
| 4,268,673 A | 5/1981 | Akkerman et al. |
| 5,089,506 A | 2/1992 | Gray et al. |
| 5,098,916 A | 3/1992 | Gray et al. |
| 5,215,992 A | 6/1993 | Gray et al. |
| 5,393,735 A | 2/1995 | Lange et al. |
| 5,410,081 A | 4/1995 | Kunde et al. |
| 5,432,175 A | 7/1995 | Piwinski et al. |
| 5,480,899 A | 1/1996 | Yano et al. |
| 5,502,027 A | 3/1996 | Lange et al. |
| 5,631,209 A | 5/1997 | Lange et al. |
| 5,776,959 A | 7/1998 | Covey et al. |
| 5,780,466 A | 7/1998 | Emonds-Alt et al. |
| 5,811,422 A | 9/1998 | Lam et al. |
| 5,856,273 A | 1/1999 | Kay et al. |
| 5,866,702 A | 2/1999 | Mackman et al. |
| 5,936,124 A | 8/1999 | Hilborn et al. |
| 5,981,436 A | 11/1999 | Drewes et al. |
| 6,066,666 A | 5/2000 | Covey et al. |

(Continued)

FOREIGN PATENT DOCUMENTS

| DE | 1801556 A1 | 5/1970 |
|---|---|---|
| DE | 2105743 A1 | 8/1972 |

(Continued)

OTHER PUBLICATIONS

Mohrle et al J. Prakt. Chem. 2000, 342, 473-485.*
U.S. Appl. No. 12/670,205, filed Jul. 25, 2008, Vitae Pharmaceuticals, Inc.
U.S. Appl. No. 12/670,209, filed Jul. 25, 2008, Vitae Pharmaceuticals, Inc.
U.S. Appl. No. 12/741,522, filed Apr. 30, 2009, Vitae Pharmaceuticals, Inc.

(Continued)

*Primary Examiner* — John Mabry
(74) *Attorney, Agent, or Firm* — McCarter & English LLP; Steven G. Davis; Michael J. DeGrazia

(57) ABSTRACT

This invention relates to novel compounds of the Formula (I), (I*), (Ia), (Ib), (Ic), (Id), (Ie), (If), (If*), (Ig), (Ih), (Ij), (Ik), (Il1-3 ), (Im1-3), (In1-3), (Io1-2), (Ip1-9), (Iq1-9), (Ir1-9) and (Is1-3) pharmaceutically acceptable salts thereof, and pharmaceutical compositions thereof, which are useful for the therapeutic treatment of diseases associated with the modulation or inhibition of 11β-HSD1 in mammals. The invention further relates to pharmaceutical compositions of the novel compounds and methods for their use in the reduction or control of the production of cortisol in a cell or the inhibition of the conversion of cortisone to Cortisol in a cell. (I)

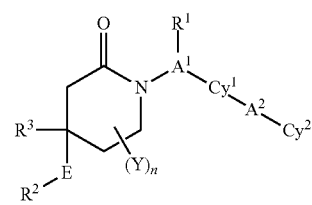

15 Claims, No Drawings

(56) References Cited

U.S. PATENT DOCUMENTS

| | | |
|---|---|---|
| 6,159,990 A | 12/2000 | Lagu et al. |
| 6,242,637 B1 | 6/2001 | Emonds-Alt et al. |
| 6,251,897 B1 | 6/2001 | Ina et al. |
| 6,368,816 B2 | 4/2002 | Walker et al. |
| 6,559,163 B2 | 5/2003 | Cai et al. |
| 6,620,815 B1 | 9/2003 | Lagu et al. |
| 6,635,630 B2 | 10/2003 | Shih et al. |
| 6,638,935 B2 | 10/2003 | Emig et al. |
| 6,653,315 B2 | 11/2003 | Tulshian et al. |
| 6,706,722 B2 | 3/2004 | Emig et al. |
| 6,794,390 B2 | 9/2004 | Lum et al. |
| 6,838,253 B2 | 1/2005 | Walker et al. |
| 6,841,671 B2 | 1/2005 | Noe et al. |
| 6,890,926 B2 | 5/2005 | Emig et al. |
| 6,900,201 B2 | 5/2005 | Noe et al. |
| 6,916,807 B2 | 7/2005 | Freeman-Cook et al. |
| 6,936,615 B2 | 8/2005 | Emig et al. |
| 6,946,487 B2 | 9/2005 | Walker et al. |
| 7,026,310 B2 | 4/2006 | Emig et al. |
| 7,056,912 B2 | 6/2006 | Emig et al. |
| 7,087,400 B2 | 8/2006 | Walker et al. |
| 7,122,531 B2 | 10/2006 | Walker et al. |
| 7,122,532 B2 | 10/2006 | Walker et al. |
| 7,129,231 B2 | 10/2006 | Walker et al. |
| 7,132,551 B2 | 11/2006 | Aquila et al. |
| 7,186,844 B2 | 3/2007 | Ikemoto |
| 7,208,487 B2 | 4/2007 | Bergnes et al. |
| 7,253,198 B2 | 8/2007 | Demont et al. |
| 7,256,005 B2 | 8/2007 | Zitzmann et al. |
| 7,262,212 B2 | 8/2007 | Tsubouchi et al. |
| 7,294,637 B2 | 11/2007 | Aquila et al. |
| 7,417,045 B2 | 8/2008 | Anilkumar et al. |
| 7,566,718 B2 | 7/2009 | Wong et al. |
| 7,652,049 B2 | 1/2010 | Ali et al. |
| 7,897,773 B2 | 3/2011 | Aletru et al. |
| 8,114,868 B2 | 2/2012 | Himmelsbach |
| 8,138,178 B2 | 3/2012 | Claremon et al. |
| 8,202,857 B2 | 6/2012 | Claremon et al. |
| 8,242,111 B2 | 8/2012 | Claremon et al. |
| 8,329,897 B2 | 12/2012 | Xu |
| 8,440,658 B2 | 5/2013 | Claremon et al. |
| 2001/0039286 A1 | 11/2001 | Dinnell et al. |
| 2006/0063819 A1 | 3/2006 | Lanter et al. |
| 2006/0089349 A1 | 4/2006 | Gundertofte et al. |
| 2006/0116382 A1 | 6/2006 | Yao et al. |
| 2006/0194780 A1 | 8/2006 | Nargund et al. |
| 2006/0276457 A1 | 12/2006 | Yu et al. |
| 2006/0276479 A1 | 12/2006 | Kim et al. |
| 2006/0276480 A1 | 12/2006 | Wong et al. |
| 2007/0021611 A1 | 1/2007 | McGuinness et al. |
| 2007/0054919 A1 | 3/2007 | Rosenblum et al. |
| 2007/0082913 A1 | 4/2007 | Kim et al. |
| 2007/0129345 A1 | 6/2007 | Zhuo et al. |
| 2007/0208001 A1 | 9/2007 | Zhuo et al. |
| 2007/0219182 A1 | 9/2007 | Lubisch et al. |
| 2007/0254875 A1 | 11/2007 | Zhi et al. |
| 2007/0254901 A1 | 11/2007 | Bilodeau et al. |
| 2007/0259891 A1 | 11/2007 | Strobel et al. |
| 2008/0004300 A1 | 1/2008 | Strobel et al. |
| 2008/0021029 A1 | 1/2008 | Strobel et al. |
| 2008/0045518 A1 | 2/2008 | Commons et al. |
| 2008/0045578 A1 | 2/2008 | Commons et al. |
| 2008/0045579 A1 | 2/2008 | Commons et al. |
| 2008/0124384 A1 | 5/2008 | Blum |
| 2008/0188482 A1 | 8/2008 | Rice et al. |
| 2008/0249087 A1 | 10/2008 | Rotstein et al. |
| 2008/0269295 A1 | 10/2008 | Haurand et al. |
| 2008/0280933 A1 | 11/2008 | Efremov et al. |
| 2008/0312271 A1 | 12/2008 | Efremov et al. |
| 2009/0018054 A1 | 1/2009 | Ali et al. |
| 2009/0170894 A1 | 7/2009 | Aletru et al. |
| 2009/0264650 A1 | 10/2009 | Cho et al. |
| 2010/0016164 A1 | 1/2010 | Hino et al. |
| 2010/0025636 A1 | 2/2010 | Gelbin et al. |
| 2010/0041637 A1 | 2/2010 | Claremon et al. |
| 2010/0197675 A1 | 8/2010 | Claremon et al. |
| 2010/0256363 A1 | 10/2010 | Xu |
| 2010/0324045 A1 | 12/2010 | Claremon et al. |
| 2010/0331320 A1 | 12/2010 | Renz et al. |
| 2011/0009402 A1 | 1/2011 | Himmelsbach |
| 2011/0015157 A1 | 1/2011 | Claremon et al. |
| 2011/0019643 A1 | 1/2011 | Kim et al. |
| 2011/0021512 A1 | 1/2011 | Claremon et al. |
| 2011/0028445 A1 | 2/2011 | Eckhardt et al. |
| 2011/0034455 A1 | 2/2011 | Claremon et al. |
| 2011/0039286 A1 | 2/2011 | Wu et al. |
| 2011/0053943 A1 | 3/2011 | Claremon et al. |
| 2011/0071139 A1 | 3/2011 | Claremon et al. |
| 2011/0105504 A1 | 5/2011 | Claremon et al. |
| 2011/0112062 A1 | 5/2011 | Claremon et al. |
| 2011/0112082 A1 | 5/2011 | Claremon et al. |
| 2011/0124635 A1 | 5/2011 | Claremon et al. |
| 2011/0136800 A1 | 6/2011 | Eckhardt et al. |
| 2011/0136821 A1 | 6/2011 | Claremon et al. |
| 2011/0190262 A1 | 8/2011 | Himmelsbach et al. |
| 2011/0224242 A1 | 9/2011 | Giethlen et al. |
| 2011/0263582 A1 | 10/2011 | Claremon et al. |
| 2011/0263583 A1 | 10/2011 | Claremon et al. |
| 2011/0263584 A1 | 10/2011 | Claremon et al. |
| 2011/0269736 A1 | 11/2011 | Eckhardt et al. |
| 2011/0269791 A1 | 11/2011 | Peters et al. |
| 2011/0269957 A1 | 11/2011 | Fandrick et al. |
| 2011/0275595 A1 | 11/2011 | Eckhardt et al. |
| 2011/0312950 A1 | 12/2011 | Eckhardt et al. |
| 2012/0040973 A1 | 2/2012 | Claremon et al. |
| 2012/0108578 A1 | 5/2012 | Himmelsbach et al. |
| 2012/0108579 A1 | 5/2012 | Renz et al. |
| 2012/0115853 A1 | 5/2012 | Eckhardt et al. |
| 2012/0172357 A1 | 7/2012 | Himmelsbach |
| 2012/0178746 A1 | 7/2012 | Claremon et al. |
| 2012/0184549 A1 | 7/2012 | Himmelsbach |
| 2012/0190675 A1 | 7/2012 | Himmelsbach |
| 2012/0208804 A1 | 8/2012 | Claremon et al. |
| 2012/0232050 A1 | 9/2012 | Claremon et al. |
| 2012/0277149 A1 | 11/2012 | Hamilton et al. |
| 2012/0277455 A1 | 11/2012 | Qu et al. |

FOREIGN PATENT DOCUMENTS

| | | |
|---|---|---|
| DE | 2108954 A1 | 9/1972 |
| DE | 2229695 A1 | 1/1974 |
| DE | 2338369 A1 | 2/1975 |
| DE | 2354002 A1 | 5/1975 |
| DE | 2411382 A1 | 9/1975 |
| DE | 2437610 A1 | 2/1976 |
| DE | 2828039 A1 | 1/1980 |
| DE | 19918725 A1 | 10/2000 |
| DE | 19929348 A1 | 12/2000 |
| DE | 100 34 623 | 1/2002 |
| DE | 10034623 | 1/2002 |
| EP | 0415642 A1 | 3/1991 |
| EP | 0454444 A1 | 10/1991 |
| EP | 0640594 A1 | 3/1995 |
| EP | 0645387 A | 3/1995 |
| EP | 0471591 B1 | 5/1995 |
| EP | 0847275 A1 | 6/1998 |
| EP | 0928789 A1 | 7/1999 |
| EP | 1156049 A | 11/2001 |
| EP | 1270724 A2 | 1/2003 |
| EP | 1801098 A1 | 6/2007 |
| EP | 1852425 A | 11/2007 |
| EP | 1864971 A | 12/2007 |
| EP | 1935420 | 6/2008 |
| GB | 1077711 | 8/1967 |
| JP | 6092945 A | 4/1994 |
| JP | 7157681 | 6/1995 |
| JP | 2009110842 A2 | 4/1997 |
| JP | 09151179 | 6/1997 |
| JP | 2002179572 A2 | 6/2002 |
| JP | 2003096058 | 4/2003 |
| JP | 2003300884 A2 | 10/2003 |
| JP | 2005-206503 A | 8/2005 |
| JP | 2005239670 | 9/2005 |
| JP | 2005272321 A | 10/2005 |

(56) References Cited

FOREIGN PATENT DOCUMENTS

| | | |
|---|---|---|
| JP | 2007 140188 | 6/2007 |
| JP | 2007 25440 | 10/2007 |
| JP | 2011519374 A | 7/2011 |
| WO | WO 92/07838 | 5/1992 |
| WO | WO 93/07128 | 4/1993 |
| WO | WO 93/13103 | 7/1993 |
| WO | WO 95/31440 | 11/1995 |
| WO | WO 96/14297 A | 5/1996 |
| WO | WO 96/23787 | 8/1996 |
| WO | 96/37494 A1 | 11/1996 |
| WO | 97/07789 A1 | 3/1997 |
| WO | WO 97/36605 | 10/1997 |
| WO | 98/22462 A1 | 5/1998 |
| WO | WO 98/57940 | 12/1998 |
| WO | WO 99/05125 | 2/1999 |
| WO | WO 99/06395 | 2/1999 |
| WO | 0009107 A2 | 2/2000 |
| WO | WO 01/00595 A1 | 1/2001 |
| WO | 0113917 A1 | 3/2001 |
| WO | WO 01/44200 A2 | 6/2001 |
| WO | WO 01/55063 | 8/2001 |
| WO | WO 02/06244 A1 | 1/2002 |
| WO | WO 02/06277 A | 1/2002 |
| WO | WO 02/22572 A2 | 3/2002 |
| WO | WO 03/043988 A1 | 5/2003 |
| WO | WO 03/057673 A | 7/2003 |
| WO | 03/097608 A2 | 11/2003 |
| WO | WO 03/093261 A1 | 11/2003 |
| WO | WO 2004/004722 A1 | 1/2004 |
| WO | WO 2004/009559 A2 | 1/2004 |
| WO | WO 2004/014859 A2 | 2/2004 |
| WO | 2004/046137 A1 | 6/2004 |
| WO | 2004056745 A2 | 7/2004 |
| WO | 2004/089896 A1 | 10/2004 |
| WO | WO 2004/094375 A | 11/2004 |
| WO | WO 2005/000845 | 1/2005 |
| WO | WO 2005/086700 A2 | 9/2005 |
| WO | 2005108360 A1 | 11/2005 |
| WO | WO 2005/108361 | 11/2005 |
| WO | WO 2005/108361 A | 11/2005 |
| WO | 2005116002 A2 | 12/2005 |
| WO | WO 2005/113525 A1 | 12/2005 |
| WO | 2006002349 A1 | 1/2006 |
| WO | WO 2006/003494 A2 | 1/2006 |
| WO | 2006017443 | 2/2006 |
| WO | WO 2006/014357 A | 2/2006 |
| WO | WO 2006/024627 A2 | 3/2006 |
| WO | WO 2006/024628 A | 3/2006 |
| WO | WO 2006/031715 A | 3/2006 |
| WO | WO 2006/040329 | 4/2006 |
| WO | WO 2006/044174 | 4/2006 |
| WO | WO 2006/049952 A | 5/2006 |
| WO | WO 2006/066924 A2 | 6/2006 |
| WO | WO 2006/066948 A1 | 6/2006 |
| WO | WO 2006/090792 A1 | 8/2006 |
| WO | 2006/109056 A1 | 10/2006 |
| WO | WO 2006/104280 A | 10/2006 |
| WO | WO 2007/008529 A2 | 1/2007 |
| WO | WO 2007/124329 A | 1/2007 |
| WO | 2007/022371 A2 | 2/2007 |
| WO | 2007/048595 A1 | 5/2007 |
| WO | WO 2007/051810 | 5/2007 |
| WO | WO 2007/061661 A2 | 5/2007 |
| WO | WO 2007/068330 A1 | 6/2007 |
| WO | 2007/076055 A2 | 7/2007 |
| WO | WO 2007/079186 A2 | 7/2007 |
| WO | WO 2007/081569 A2 | 7/2007 |
| WO | WO 2007/081570 A | 7/2007 |
| WO | WO 2007/081571 A2 | 7/2007 |
| WO | WO 2007/084314 A2 | 7/2007 |
| WO | 2007101270 A1 | 9/2007 |
| WO | 2007103719 A2 | 9/2007 |
| WO | WO 2007/109456 A2 | 9/2007 |
| WO | WO 207/118185 A2 | 10/2007 |
| WO | 2007/127763 A2 | 11/2007 |
| WO | 2007123853 A2 | 11/2007 |
| WO | WO 2007/124254 | 11/2007 |
| WO | WO 2007/124337 | 11/2007 |
| WO | WO 2007/127693 A | 11/2007 |
| WO | WO 2008/000951 | 1/2008 |
| WO | 2008024497 A2 | 2/2008 |
| WO | WO 2008/031227 A1 | 3/2008 |
| WO | WO 2008/036715 A1 | 3/2008 |
| WO | 2008/046578 A2 | 4/2008 |
| WO | WO 2008/046758 A | 4/2008 |
| WO | WO 2008/059948 A | 5/2008 |
| WO | WO 2008/106128 | 9/2008 |
| WO | WO 2008/106128 A | 9/2008 |
| WO | WO 2008/118332 A2 | 10/2008 |
| WO | 2009020140 A1 | 2/2009 |
| WO | WO 2009/017664 | 2/2009 |
| WO | WO 2009/017664 A1 | 2/2009 |
| WO | WO 2009/017671 | 2/2009 |
| WO | WO 2009/061498 | 5/2009 |
| WO | WO 2009/063061 | 5/2009 |
| WO | WO 2009/075835 | 6/2009 |
| WO | WO 2009/088997 | 7/2009 |
| WO | WO 2009/094169 A | 7/2009 |
| WO | WO 2009/100872 | 8/2009 |
| WO | WO 2009/102428 | 8/2009 |
| WO | WO 2009/102460 | 8/2009 |
| WO | 2009/107664 A1 | 9/2009 |
| WO | 2009108332 A1 | 9/2009 |
| WO | WO 2009/117109 | 9/2009 |
| WO | 2009131669 A2 | 10/2009 |
| WO | WO 2009/134384 | 11/2009 |
| WO | WO 2009/134387 | 11/2009 |
| WO | WO 2009/134392 | 11/2009 |
| WO | WO 2009/134400 | 11/2009 |
| WO | WO 2009/138386 | 11/2009 |
| WO | 2010/010150 A1 | 1/2010 |
| WO | WO 2010/010149 | 1/2010 |
| WO | WO 2010/010157 | 1/2010 |
| WO | WO 2010/010174 | 1/2010 |
| WO | WO 2010/011314 | 1/2010 |
| WO | WO 2010/023161 | 3/2010 |
| WO | WO 2010/046445 | 4/2010 |
| WO | 2010089303 A1 | 8/2010 |
| WO | WO 2010/091067 | 8/2010 |
| WO | 2010104830 A1 | 9/2010 |
| WO | WO 2010/127237 | 11/2010 |
| WO | 2010/139673 A1 | 12/2010 |
| WO | 2010141424 A1 | 12/2010 |
| WO | 2011002910 A1 | 1/2011 |
| WO | 2011011123 A1 | 1/2011 |
| WO | 2011031979 A1 | 3/2011 |
| WO | 2011/057054 A1 | 5/2011 |
| WO | 2011056737 A1 | 5/2011 |
| WO | 2011159760 A1 | 12/2011 |
| WO | 2011161128 A1 | 12/2011 |
| WO | 2012059416 A1 | 5/2012 |

OTHER PUBLICATIONS

U.S. Appl. No. 12/990,309, filed Apr. 30, 2009, Vitae Pharmaceuticals, Inc.
U.S. Appl. No. 12/990,296, filed Apr. 30, 2009, Vitae Pharmaceuticals, Inc.
U.S. Appl. No. 12/745,663, filed Nov. 7, 2008, Vitae Pharmaceuticals, Inc.
U.S. Appl. No. 12/747,391, filed Dec. 10, 2008, Vitae Pharmaceuticals, Inc.
U.S. Appl. No. 12/863,634, filed Jan. 21, 2009, Vitae Pharmaceuticals, Inc.
U.S. Appl. No. 12/867,374, filed Feb. 13, 2009, Vitae Pharmaceuticals, Inc.
U.S. Appl. No. 12/933,027, filed Mar. 18, 2009, Vitae Pharmaceuticals, Inc.
U.S. Appl. No. 12/741,532, filed Sep. 27, 2010, Vitae Pharmaceuticals, Inc.
U.S. Appl. No. 12/771,499, filed Apr. 30, 2010, Vitae Pharmaceuticals, Inc.
International Search Report and Written Opinion—(PCT/US2008/009048) Date of Mailing Dec. 4, 2008.

(56) References Cited

OTHER PUBLICATIONS

International Search Report—(PCT/US2009/004261) Date of Mailing Oct. 21, 2009.
Shibata, et al., "Cycloaddition of Oxetanes with Heterocumulenes Catalysed by Organotin Iodine-Lewis Base Complex", Journal of Heterocyclic Chemistry, vol. 24, 1987, pp. 361-363.
Database CA [Online], Chemical Abstracts Service, Fukushima et al., "Preparation of Imidazolidinone Derivatives as 11.beta.-HSD1 Inhibitors", 2007, XP 002531878.
Gavezzotti, "Are Crystal Structures Predictable?", Accounts of Chemical Research, 1994, vol. 27, pp. 309-314.
Vippagunta, et al., "Crystalline Solids", Advanced Drug Deliver Reviews, 2001, vol. 48, pp. 3-26.
MS Bitar, "Glucocorticoid Dynamics and Impaired Wound Healing in Diabetes Mellitus", Am J Pathol., 1998, vol. 152, pp. 547-554.
MS Bitar, et al., "Heat-Shock Protein 72/73 and Impaired Wound Healing in Diabetic and Hypercortisolemic States", Sugery, 1999, vol. 125, pp. 594-601.
MS Bitar, et al., "Glucocorticoid-Dependent Impairment of Wound Healing in Experimental Diabetes: Amelioration by Adrenalectomy and RU 486", J Surg Res., 1999, vol. 82, pp. 234-243.
MS Bitar, "Insulin and Glucocorticoid-Dependent Suppression of the IGF-I System in Diabetic Wounds", Sugery, 2000, vol. 127, pp. 687-695.
Database Caplus [Online] Chemical Abstracts Service, Mallard et al., "Spiroheterocyclic Cycloalkane Compounds. II. Synthesis of 6-Substituted-Tetrahydro-2H-1,3-Oxazine-2-Ones", XP002516521, retrieved from STN Database accession No. 1969:68280 CAS RN: 20057-45-8 abstract.
Chimica Therapeutica, 1968, vol. 3 5 , pp. 321-324, 1968.
Database Caplus [Online] Chemical Abstracts Service, Slyusarenko et al., "Synthesis based on Thionylamides.IV. 2-Alkoxy-5,6-Dihydro-1,3-Oxazines", XP002516522, retrieved from STN Database accession No. 1978:563520 CAS RN: 67868-26-2 abstract.
Zhurnal Organicheskoi Khimii, 1978, vol. 14(5), pp. 1092-1094.
Database CA [Online], Chemical Abstracts Service, Fukushima et al., "Preparation of Imidazolidinone Derivatives as 11.beta.-HSD1 Inhibitors", XP 002531878.
"Khimiia Elementoorganicheskikh Soedineni", 1982, vol. 1982 pp. 22-26.
"Zhurnal Organicheskoi Khimii", 1982, vol. 18, PT 11, p. 2468.
Chemical Abstracts, vol. 98, No. 11, 1983, Columbus, Ohio, US; abstract No. 89280k, Lapkin, et al., "Synthesis of 1,3-oxazin-2,4-diones", p. 552 col. 1, XP002504063 abstract.
Chemical Abstracts, vol. 99, No. 23, 1983, Columbus, Ohio, US; abstract No. 195067b, Saitkulova, et al., "Synthesis involving bromozinc alcoholates of carboxylic acid esters", p. 764 col. 1, XP002504064 abstract.
Goubet, et al., "Conversion of a Thiohydantoin to the Corresponding Hydantoin via a Ring-Opening/Ring Closure Mechanism", Tetrahedron Letters, Elsevier, Amsterdam, 1996, vol. 37, pp. 7727-7730.
Ho-Jane Shue et al., "Cyclic Urea Derivatives as Potent NK1 Selective Antagonists", Bioorganic & Medicinal Chemistry Letters, 2005, vol. 15, pp. 3896-3899.
Ho-Jane Shue et al., "Cyclic Urea Derivatives as Potent NK1 Selective Antagonists. Part II: Effects of Fluoro and Benzylic Methyl Substitutions", Bioorganic & Medicinal Chemistry Letters, 2006, vol. 16, pp. 1065-1069.
Kashima, et al., "Preparation of N-Aryl-2,4-diaminopentanes by the Ring Opening Reaction of 1-Aryl-3,4,5,6-tetrahydro-2-(1H)pyrimidinones", Journal of Heterocyclic Chemistry, vol. 18, 1981, pp. 1595-1596, XP002517485.
Lohray et al., "Enantiospecific Synthesis of 6-Substituted N-Aryl-1,3-Oxazin-2-Ones", Tetrahedron Letters, 1998, vol. 39, pp. 6555-6556.
Malgorzata Wamil and Jonathan R. Seek!, "Inhibition of 11β-hydroxysteroid Dehydrogenase Type 1 as a Promising Therapeutic Target", Drug Discovery Today, 2007, vol. 12, pp. 504-520.
Muehlstadt, et al., "Cyclisation reactions of beta, gamma-unsaturated derivatives of carbonic acid. IX.", Journal Fuer Praktische Chemie, vol. 328, 1986, pp. 163-172, XP002504062 p. 164, compound 4j.
Schoellkopf, et al., "Umsetzungen Alphametallierter Isocyanide Mit Einigen 1,3-Dipolen/Reactions of Alpha-Metalated Osicyanides with Some 1,3-Dipoles", Liebigs Annalen Der Chemie, Verlag Chemie GMBH. Weinheim, DE, 1980, vol. 4, pp. 600-610.
Suga, Seiji et al., ""N-Acyliminium Ion Pool" as a Heterodiene in [4+2] Cycloaddition Reaction", Organic Letters, 2003, vol. 5, pp. 945-947.
Suga, Seiji et al., "Cycloaddition of "N-Acyliminium Ion Pools" with Carbon-Carbon Multiple Bonds", Bulletin of the Chemical Society of Japan, Chemical Society of Japan, 2005, vol. 78, pp. 1206-1217.
Tamaru et al., "Urea as the Most Reactive and Versatile Nitrogen Nucleophile for the Palladium(2+)-Catalyzed Cyclization of Unsaturated Amines", Journal of the American Chemical Society, 1988, vol. 110, pp. 3994-4002.
Yoshida, Masaaki et al., "Selective synthesis of five- and six-membered cyclic carbamates by the reaction of 2-(1-haloalkyl)oxiranes with carbon dioxide and aliphatic primary amines", Heterocycles, Elsevier Science Ltd., 1993, vol. 35 (2), pp. 623-626.
Yoshinao Tamaru, "Palladium(2+)-Catalyzed Intramolecular Aminocarbonylation of 3-Hydroxy-4-pentenylamines and 4-Hydroxy-5-hexenylamines", J. Org. Chem., 1988, pp. 5731-5741.
International Search Report & Written Opinion—(PCT/US2008/009017) Date of Mailing Apr. 12, 2008.
International Search Report Written Opinion—(PCT/US2008/002517) Date of Mailing Dec. 29, 2008.
International Search Report—(PCT/US2009/002653) Date of Mailing Jul. 3, 2009.
International Search Report—(PCT/US2009/002641) Date of Mailing Jul. 3, 2009.
International Search Report—(PCT/US2009/002629) Date of Mailing Jul. 3, 2009.
International Search Report—(PCT/US2009/002633) Date of Mailing Jul. 3, 2009.
International Search Report—PCT/US2008/012618) Date of Mailing Dec. 3, 2009.
International Search Report—(PCT/US2009/000057) Date of Mailing Mar. 25, 2009.
International Search Report—(PCT/US2008/013539) Date of Mailing Mar. 19, 2009.
International Search Report—(PCT/US2009/000853) Date of Mailing Sep. 2, 2009.
International Search Report—(PCT/US2009/000421) Date of Mailing Apr. 15, 2009.
International Search Report—(PCT/US2009/000908) Date of Mailing Sep. 17, 2009.
International Search Report—(PCT/US2009/001712) Date of Mailing Jul. 14, 2009.
Database File Registry [Online], Chemical Abstracts Service, Columbus, Ohio, US, 2007, Database accession No. 958700-63-5, Abstract, XP002556893.
Database File Registry [Online], Chemical Abstracts Service, Columbus, Ohio, US, 2007, Database accession No. 958696-39-4, Abstract, XP002556894.
Database File Registry [Online], Chemical Abstracts Service, Columbus, Ohio, US, 2007, Database accession No. 958696-32-7, Abstract, XP002556895.
Database File Registry [Online], Chemical Abstracts Service, Columbus, Ohio, US, 2007, Database accession No. 958629-39-5, Abstract, XP002556896.
Database File Registry [Online], Chemical Abstracts Service, Columbus, Ohio, US, 2007, Database accession No. 958629-22-6, Abstract, XP002556897.
Database File Registry [Online], Chemical Abstracts Service, Columbus, Ohio. US, 2007, Database accession No. 958629-14-6, Abstract, XP002556898.
Database File Registry [Online], Chemical Abstracts Service, Columbus, Ohio, US, 2007, Database accession No. 958625-83-7, Abstract, XP002556899.

(56) References Cited

OTHER PUBLICATIONS

Database File Registry [Online], Chemical Abstracts Service, Columbus, Ohio, US, 2007, Database accession No. 958599-31-0, Abstract, XP002556900.
International Search Report1'(PCT/US2010/023021) Date of Mailing Aug. 5, 2010.
Office Action dated Jun. 14, 2012 for corresponding U.S. Appl. No. 13/347,784.
Office Action dated May 3, 2012 for corresponding U.S. Appl. No. 13/347,799.
Office Action for U.S. Appl. No. 12/741,522 (U.S. Patent No. 8,138,178), date of mailing Dec. 15, 2010.
Office Action for U.S. Appl. No. 12/741,532 (US Patent No. 8,114,868), date of mailing Dec. 15, 2010.
Office Action for U.S. Appl. No. 12/771,499, date of mailing Dec. 21, 2010.
Olesen et al.: Current Opin Drug Dis Dev, 2001, vol. 4, No. 4, p. 471-478.
Patani et al. Chem Rev, 1996 p. 3147-3176.
Rosenstock et.al. Diabetes Care Jul. 2010, LNKDPUBMED: 20413513, vol. 33, No. 7, pp. 1516-1522.
Senanayake, C. Presentation: "Timely Chemical Process Research is a Critical Part for Efficient Drug Development". 4th Siegfried Symposium, Sep. 23, 2010, p. 1-91, Retrieved from internet: URL: http://www.siegfried/ch/fileadmin/User2/Bilder/Fotogalerien/Symposium_2010/Award_Talk_Senanayake.pdf. Retrieved on Feb. 23, 2010.
Souillac et al., Characterization of Delivery Systems, Differential Scanning Calorimetry, pp. 217-218 (in Encyclopedia of Controlled Drug Delivery, 1999, John Wiley & Sons, pp. 212-227).
Stewart et al. Vitam Norm. 1999;57:249-324.
Sullivan, John M. and Efner, Howard F., "The Preparation of 6-Aryltetrahydro-1,3-oxazin-2-ones and Their Hydrolysis to 3-Substituted Propylamines," The Journal of Organic Chemistry, 33 (5): 2134-2136 (1968).
Taddayon et.al. Expert opinion on Investigational Drugs, Ashley Publication Ltd. 2003, vol. 12, No. 3, pp. 307-324.
Tamaru, Y. et al., "Palladium (2+)-Catalyzed Intramolecular Aminocarbonylation of 3-Hydroxy-4-pentenylamines and 4-Hydroxy-5-hexenylamines". Journal Organic Chemistry, vol. 53, No. 24, 1988, p. 5731-5741.
Tang, W. et al., "Novel and Efficient Chiral Bisphosphorus Ligands for Rhodium-Catalyzed Asymmetric Hydrogenation". Organic Letters, 2010, vol. 12, No. 5, p. 1104-1107.
Tang, W. et al., "Novel, Tunable, and Efficient Chiral Bisdihydrobenzooxaphosphole Ligands for Asymmetric Hydrogenation". Organic Letters, 2010, vol. 12, No. 1., p. 176-179.
Thiel (Nature Biotechnol 2:513-519, 2004).
Thornber et al.: Chem Soc Rev, 1979, vol. 8, p. 563-580.
Vidic et al.: Chem. Ber. 1976, 109, p. 2657-2669.
Wolfling, Janos et al., "Neighboring Group Participation Part 15. Stereoselective Synthesis of Some Steroidal Tetrahydrooxaziin-2-ones, as Novel Presumed Inhibitors of Human 5?-Reductase," Steroids, 69: 451-460 (2004).
Worthy, AD. et al., "Regioselective Hydroformylation of Sulfonamides using a Scaffolding Ligand". Organic Letters, 2009, vol. 11, No. 13—p. 2764-2767.
Yokoyama et al.: J. Med. Chem. 1979, 22, p. 537-553.
Aluri, B.R. et al., "Sterically and Polarity-Controlled Reactions of tBuLi with P=CH-NR Heterocycles: Novel Heterocyclic P-and P,O-Ligands and Preliminary Tests in Transition-Metal Catalysis", Chem. Eur. Journal, vol. 14, 2008, p. 4328-4335.
Aluri. B.R. et al., "Bulky n-Substituted 1,3-Benzazaphospholes: Access via Pd-Catalyzed C-N and C-P Cross Coupling, Lithiation, and Conversion to Novel P=C PtBu2 Hybrid Ligands". Inorganic Chemistry, 2008, 47, p. 6900-6912.
Anderson, (Chem and Biol 10:787-797, 2003).
Bosch et al.: Heterocycles 1980, 14, p. 1983-1988.
CA 1267843-31-1, (Aug. 10, 2009).
CA 154:284276, (Mar. 17, 2011).
Caplus-133:4656—Anantanarayan, A. el. al., "Preparation of heteroarylpyrazoles as P38 kinase inhibitors". 2000.
Caplus-147:134403, Hembrough, TA, et al., Composition and methods comprising proteinase activated receptor 2 antagonists for treatment of angiogenesis and inflammatory disorders and cancer. 2007.
Caplus-77:5360, Helsley, G. C. "Antispasmodic 8-carbamoyl-3-phenylnortropanes". 1972.
Chalmers (TIPS vol. 17, pp. 166-172 Apr. 1996).
Chemical Abstracts, Registry No. 351443-37-3 (Available on Aug. 15, 2001.).
Claremon et al. CAS: 150:214405, 2009.
Database Caplus [Online] Chemical Abstracts Service, Maillard et al., "Spiroheterocyclic Cycloalkane Compounds. II. Synthesis of 6-Substituted-Tetrahydro-2H-1,3-Oxazine-2-Ones", XP002516521, retrieved from STN Database accession No. 1969:68280 CASRN: 20057-45-8 abstract, (1969).
Database Caplus [Online] Chemical Abstracts Service, Slyusarenko et al., "Synthesis based on Thionylamides.IV. 2-Alkoxy-5,6-Dihydro-1,3-Oxazines", XP002516522, retrieved from STN Database accession No. 1978:563520 CAS RN: 67868-26-2 abstract,(1978).
DeMarinis R.M. et.al. Journal of Medicinal Chemistry 1981, vol. 24, No. 12, pp. 1432-1437.
Donohoe, T.J. et al., "Stereoselectivity in the double reductive alkylation of pyrroles: synthesis of cis-3,4-disubstituted pyrrolidines". Chemical Communications, vol. 1999, No. 2, Feb. 1, 1999, p. 141-142.
Evans, B.E. et al., "Orally active, nonpeptide osytocin antagonists". Journal of Medicinal Chemistry, American Chem. Soc., Vo. 35, No. 21, Oct. 15, 1992, p. 3919-3927.
Examiner Interview Summary dated May 2, 2011, in U.S. Appl. No. 12/741,522 (U.S. Patent No. 8,138,178).
Fandrick, DR. et al., "Copper Catalyzed Asymmetric Propargylation of Aldehydes". JACS Communications, Published on Web May 18, 2010, J. Am. Chem. Soc., vol. 132, No. 22, 2010, p. 7600,7601.
Gutkowska et al.: Acta Polonaie Pharmaceutica 1987, 39, p. 411-414.
Gutkowska et al.: Acta Poloniae Pharmaceutica 1986, 43, p. 403-405.
Gutkowska et al.: Acta Poloniae Pharmaceutica, 1982, vol. 39, p. 61-64.
Harno et.al. Trends in Endocrinology and Metabolism, Elsevier Science Publishing, New York 2010, vol. 21, No. 10, pp. 619-627.
Hughes, K.A. et al., "11-beta-hydroxysteroid dehydrogenase type 1 (11b-HSD1) inhibitors in Type 2 diabetes mellitus and obesity". Expert Opinion, Investig. Drugs, 17(4), 2008, pp. 481-496.
International Search Report and Written Opinion for PCT/EP/2009/059496 mailed Nov. 17, 2009.
International Search Report and Written Opinion for PCT/EP2009/059509, mailed Feb. 9, 2009.
Nternational Search Report and Written Opinion for PCT/EP2010/051262 mailed Aug. 7, 2011.
International Search Report and Written Opinion for PCT/EP2011/060386 mailed Sep. 16, 2011.
International Search Report and Written Opinion for PCT/US2010/054912 mailed Mar. 16, 2011.
International Search Report and Written Opinion for PCT/US2012/050679 mailed Oct. 31, 2012.
International Search Report for PCT/EP2009/063913 mailed May 6, 2010.
International Search Report for PCT/EP2011/068938 mailed Mar. 27, 2012.
Kametani et al. Chem Pharma Bull, 1965 vol. 13, No. 3, p. 295-299.
Lightburn, T.E. et al., "Catalytic Scaffolding Ligands: An Efficient Strategy for Direction Reactions". JACS Communications, Published on Web May 25, 2008, Journal American Chem. Soc., vol. 130, No. 29, 2008, p. 9210-9211.
Ma et al.: Synthesis 2007, p. 161-163.
Ma et al.: Tetrahedron 2007, 63, p. 7523-7531.
Morissette et al. Advanced Drug Deliery Reviews 2004, 56, 275-300.
Office Action dated Apr. 3, 2012 for corresponding U.S. Appl. No. 13/318,271.

\* cited by examiner

LACTAM INHIBITORS OF 11-β-HYDROXYSTEROID DEHYDROGENASE 1

RELATED APPLICATIONS

This application is the U.S. National Stage of PCT International Application Number PCT/US2009/000057, filed Jan. 7, 2009, which claims the benefit of U.S. Provisional Application No. 61/010,300, filed Jan. 7, 2008, the entire teachings of which are incorporated herein by reference.

BACKGROUND OF THE INVENTION

Glucocorticoids, such as cortisol (hydrocortisone), are steroid hormones that regulate fat metabolism, function and distribution, and play a role in carbohydrate, protein and fat metabolism. Glucocorticoids are also known to have physiological effects on development, neurobiology, inflammation, blood pressure, metabolism, and programmed cell death. Cortisol and other corticosteroids bind both the glucocorticoid receptor (GR) and the mineralocorticoid receptor (MR), which are members of the nuclear hormone receptor superfamily and have been shown to mediate cortisol function in vivo. These receptors directly modulate transcription via DNA-binding zinc finger domains and transcriptional activation domains.

Until recently, the major determinants of glucocorticoid action were attributed to three primary factors: (1) circulating levels of, glucocorticoid (driven primarily by the hypothalamic-pituitary-adrenal (HPA) axis); (2) protein binding of glucocorticoids in circulation; and (3) intracellular receptor density inside target tissues. Recently, a fourth determinant of glucocorticoid function has been identified: tissue-specific pre-receptor metabolism by glucocorticoid-activating and -inactivating enzymes. These 11β-hydroxysteroid dehydrogenase (11β-HSD) pre-receptor control enzymes modulate activation of GR and MR by regulation of glucocorticoid hormones. To date, two distinct isozymes of 11-beta-HSD have been cloned and characterized: 11β-HSD1 (also known as 11-beta-HSD type 1, 11betaHSD1, HSD11B1, HDL, and HSD11L) and 11β-HSD2. 11β-HSD1 is a bi-directional oxidoreductase that regenerates active cortisol from inactive 11-keto forms, whereas 11β-HSD2 is a unidirectional dehydrogenase that inactivates biologically active cortisol by converting it into cortisone.

The two isoforms are expressed in a distinct tissue-specific fashion, consistent with the differences in their physiological roles. 11β-HSD1 is widely distributed in rat and human tissues; expression of the enzyme and corresponding mRNA have been detected in human liver, adipose tissue, lung, testis, bone and ciliary epithelium. In adipose tissue, increased cortisol concentrations stimulate adipocyte differentiation and may play a role in promoting visceral obesity. In the eye, 11β-HSD1 may regulate intraocular pressure and may contribute to glaucoma; some data suggest that inhibition of 11β-HSD1 may cause a drop in intraocular pressure in patients with intraocular hypertension (Kotelevstev et al. (1997), Proc. Natl. Acad. Sci. USA 94(26):14924-9). Although 11β-HSD1 catalyzes both 11-beta-dehydrogenation and the reverse 11-oxoreduction reaction, 11β-HSD1 acts predominantly as a NADPH-dependent oxoreductase in intact cells and tissues, catalyzing the formation of active cortisol from inert cortisone (Low et al. (1994) J. Mol. Endocrin. 13: 167-174). In contradistinction, 11β-HSD2 expression is found mainly in mineralocorticoid target tissues such as kidney (cortex and medulla), placenta, sigmoid and rectal colon, salivary gland and colonic epithelial cell lines. 11β-HSD2 acts as an NAD-dependent dehydrogenase catalyzing the inactivation of cortisol to cortisone (Albiston et al. (1994) Mol. Cell. Endocrin. 105: R11-R17), and has been shown to protect the MR from glucocorticoid excess (e.g., high levels of receptor-active cortisol) (Blum, et al. (2003) Prog. Nucl. Acid Res. Mol. Biol. 75:173-216).

Mutations in either the 11β-HSD1 or the 11β-HSD2 genes result in human pathology. For example, individuals with mutations in 11β-HSD2 are deficient in this cortisol-inactivation activity and, as a result, present with a syndrome of apparent mineralocorticoid excess (also referred to as 'SAME') characterized by hypertension, hypokalemia, and sodium retention (Edwards et al. (1988) Lancet 2: 986-989; Wilson et al. (1998) Proc. Natl. Acad. Sci. 95: 10200-10205). Similarly, mutations in 11β-HSD1 and in the gene encoding a co-localized NADPH-generating enzyme, hexose 6-phosphate dehydrogenase (H6PD), can result in cortisone reductase deficiency (CRD); these individuals present with ACTH-mediated androgen excess (hirsutism, menstrual irregularity, hyperandrogenism), a phenotype resembling polycystic ovary syndrome (PCOS) (Draper et al. (2003) Nat. Genet. 34: 434-439).

Notably, disruption of homeostasis in the HPA axis by either deficient or excess secretion or action results in Cushing's syndrome or Addison's disease, respectively (Miller and Chrousos (2001) Endocrinology and Metabolism, eds. Felig and Frohman (McGraw-Hill, New York), 4$^{th}$ Ed.: 387-524). Patients with Cushing's syndrome or receiving glucocorticoid therapy develop reversible visceral fat obesity. The phenotype of Cushing's syndrome patients closely resembles that of Reaven's metabolic syndrome (also known as Syndrome X or insulin resistance syndrome), the symptoms of which include visceral obesity, glucose intolerance, insulin resistance, hypertension, type 2 diabetes and hyperlipidemia (Reaven (1993) Ann. Rev. Med. 44: 121-131). Although the role of glucocorticoids in human obesity is not fully characterized, there is mounting evidence that 11β-HSD1 activity plays an important role in obesity and metabolic syndrome (Bujalska et al. (1997) Lancet 349: 1210-1213); (Livingstone et al. (2000) Endocrinology 131: 560-563; Rask et al. (2001) J. Clin. Endocrinol. Metab. 86: 1418-1421; Lindsay et al. (2003) J. Clin. Endocrinol. Metab. 88: 2738-2744; Wake et al. (2003) J. Clin. Endocrinol. Metab. 88: 3983-3988).

Data from studies in mouse transgenic models supports the hypothesis that adipocyte 11β-HSD1 activity plays a central role in visceral obesity and metabolic syndrome (Alberts et al. (2002) Diabetologia. 45(11): 1526-32). Over-expression in adipose tissue of 11β-HSD1 under the control of the aP2 promoter in transgenic mice produced a phenotype remarkably similar to human metabolic syndrome (Masuzaki et al. (2001) Science 294: 2166-2170; Masuzaki et al. (2003) J. Clinical Invest. 112: 83-90). Moreover, the increased activity of 11β-HSD1 in these mice is very similar to that observed in human obesity (Rask et al. (2001) J. Clin. Endocrinol. Metab. 86: 1418-1421). In addition, data from studies with 11β-HSD1-deficient mice produced by homologous recombination demonstrate that the loss of 11β-HSD1 leads to an increase in insulin sensitivity and glucose tolerance due to a tissue-specific deficiency in active glucocorticoid levels (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938).

The published data supports the hypothesis that increased expression of 11β-HSD1 contributes to increased local conversion of cortisone to cortisol in adipose tissue and hence that 11β-HSD1 plays a role in the pathogenesis of central obesity and the appearance of the metabolic syndrome in humans (Engeli, et al., (2004) Obes. Res. 12: 9-17). Therefore, 11β-HSD1 is a promising pharmaceutical target for the treatment of the metabolic syndrome (Masuzaki, et al., (2003) Curr. Drug Targets Immune Endocr. Metabol. Disord. 3: 255-62). Furthermore, inhibition of 11β-HSD1 activity may prove beneficial in treating numerous glucocorticoid-related disorders. For example, 11β-HSD1 inhibitors could be effective in combating obesity and/or aspects of the metabolic syndrome cluster, including glucose intolerance, insulin resistance, hyperglycemia, hypertension, and/or hyperlipidemia (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). In addition, inhibition of 11β-HSD1 activity may have beneficial effects on the pancreas, including the enhancement of glucose-stimulated insulin release (Billaudel and Sutter (1979) Horm. Metab. Res. 11: 555-560; Ogawa et al. (1992) J. Clin. Invest. 90: 497-504; Davani et al. (2000) J. Biol. Chem. 275: 34841-34844).

Furthermore, given that inter-individual differences in general cognitive function have been linked to variability in the long-term exposure to glucocorticoids (Lupien et al. (1998) Nat. Neurosci. 1: 69-73) and dysregulation of the HPA axis resulting in chronic exposure to glucocorticoid excess in certain brain subregions has been theorized to contribute to the decline of cognitive function (McEwen and Sapolsky (1995) Curr. Opin. Neurobiol. 5: 205-216), one might predict that inhibition of 11β-HSD1 could reduce exposure to glucocorticoids in the brain and thereby protect against deleterious glucocorticoid effects on neuronal function, including cognitive impairment, dementia, and/or depression. Notably, it is known that stress and glucocorticoids influence cognitive function (de Quervain et al. (1998) Nature 394: 787-790); and it has been shown that 11β-HSD1, through its control of glucocorticoid action in the brain, may have effects on neurotoxicity (Rajan et al. (1996) Neuroscience 16: 65-70; Seckl (2000) Neuroendocrinol. 18:49-99).

There is also evidence that glucocorticoids and 11β-HSD1 play a role in regulation of in intra-ocular pressure (IOP) (Stokes et al. (2000) Invest. Ophthalmol. Vis. Sci. 41: 1629-1683; Rauz et al. (2001) Invest. Ophthalmol. Vis. Sci. 42: 2037-2042); if left untreated, elevated IOP can lead to partial visual field loss and eventually blindness. Thus, inhibition of 11β-HSD1 in the eye could reduce local glucocorticoid concentrations and IOP, and 11β-HSD1 hence could potentially be used to treat glaucoma and other visual disorders.

Transgenic aP2-11βHSD1 mice exhibit high arterial blood pressure and have increased sensitivity to dietary salt. Moreover, plasma angiotensinogen levels are elevated in the transgenic mice, as are angiotensin II and aldosterone; and treatment of the mice with an angiotensin II antagonist alleviates the hypertension (Masuzaki et al. (2003) J. Clinical Invest. 112: 83-90). This suggests that hypertension may be caused or exacerbated by 11β-HSD1 activity. Thus, 11β-HSD1 inhibitors may be useful for treatment of hypertension and hypertension-related cardiovascular disorders. Inhibition of 11β-HSD1 in mature adipocytes is also expected to attenuate secretion of plasminogen activator inhibitor 1 (PAI-1), which is an independent cardiovascular risk factor (Halleux et al. (1999) J. Clin. Endocrinol. Metabl. 84: 4097-4105).

Glucocorticoids can have adverse effects on skeletal tissues; and prolonged exposure to even moderate glucocorticoid doses can result in osteoporosis (Cannalis (1996) J. Clin. Endocrinol. Metab. 81: 3441-3447). In addition, 11β-HSD1 has been shown to be present in cultures of human primary osteoblasts as well as cells from adult bone (Cooper et al. (2000) Bone 27: 375-381), and the 11β-HSD1 inhibitor carbenoxolone has been shown to attenuate the negative effects of glucocorticoids on bone nodule formation (Bellows et al. (1998) Bone 23: 119-125). Thus, inhibition of 11β-HSD1 is predicted to decrease the local glucocorticoid concentration within osteoblasts and osteoclasts, thereby producing beneficial effects in various forms of bone disease, including osteoporosis.

11β-HSD1 inhibitors may also be useful for immunomodulation. Although glucocorticoids are perceived to suppress the immune system, in actuality, there is a complex, dynamic interaction between the HPA axis and the immune system (Rook (1999) Baillier's Clin. Endocrinol. Metabl. 13: 576-581). Glucocorticoids play a role in modulating the balance between cell-mediated and humoral immune response, with high glucocorticoid activity normally associated with a humoral response. Inhibition of 11β-HSD1 therefore can be used a means of shifting the immune response towards a cell-mediated response. Certain disease states, such as tuberculosis, leprosy (Hansen's disease) and psoriasis, trigger immune responses that are biased towards a humoral response whereas the more effective immune response may be a cell-mediated response. Hence, 11β-HSD1 inhibitors may be useful for treating such diseases.

It has been reported that glucocorticoids inhibit wound healing, especially in diabetic patients with ulcers (Bitar et al. (1999) J. Surg. Res. 82: 234-243; Bitar et al. (1999) Surgery 125: 594-601; Bitar (2000) Surgery 127: 687-695; Bitar (1998) Am. J. Pathol. 152: 547-554). Patients that exhibit impaired glucose tolerance and/or type 2 diabetes often also have impaired wound healing. Glucocorticoids have been shown to increase the risk of infection and delay wound healing (Anstead (1998) Adv. Wound Care 11:277-285). Moreover, there is a correlation between elevated levels of cortisol in wound fluid and non-healing wounds (EP Patent App. No. 0 902 288). Recent published patent applications have suggested that certain 11β-HSD1 inhibitors may be useful for promoting wound healing (PCT/US2006/043, 951).

As evidenced herein, there is a continuing need for new and improved drugs that inhibit 11β-HSD1. The novel compounds of the instant invention are effective inhibitors of 11β-HSD1.

Another embodiment of the invention is a compound of Formulas I, I*, Ia, Ib, Ic, Id, Ie, If, If*, Ig, Ih, Ij, Ik, $Il^{1-3}$, $Im^{1-3}$, $In^{1-3}$, $Io^{1-2}$, $Ip^{1-9}$, $Iq^{1-9}$, $Ir^{1-9}$ or $Is^{1-3}$ or a pharmaceutically acceptable salt, enantiomer or diastereomer thereof, wherein any one of the following provisos apply or any combination thereof:

SUMMARY OF THE INVENTION

It has now been found that compounds of Formula I or pharmaceutically acceptable salts or prodrugs thereof, are effective inhibitors of 11β-HSD1. In a first embodiment, Formula I and its constituent members are defined herein as follows:

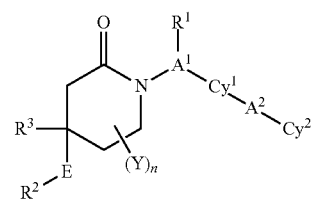

I wherein:

$R^1$ is (a) absent or (b) is selected from $(C_1-C_6)$alkyl, $(C_2-C_6)$alkenyl, $(C_2-C_6)$alkynyl, $(C_1-C_3)$alkoxy$(C_1-C_3)$alkoxy, or $(C_1-C_3)$alkoxy$(C_1-C_3)$alkyl and is optionally substituted with up to four groups independently selected from fluorine, cyano, oxo, $R^4$, $R^4O-$, $(R^4)_2N-$, $R^4O_2C-$, $R^4S$, $R^4S(=O)-$, $R^4S(=O)_2-$, $R^4C(=O)NR^4-$, $(R^4)_2NC(=O)-$, $(R^4)_2NC(=O)O-$, $(R^4)_2NC(=O)NR^4-$, $R^4OC(=O)NR^4-$, $(R^4)_2NC(=NCN)NR^4-$, $(R^4O)_2P(=O)O-$, $(R^4O)_2P(=O)NR^4-$, $R^4OS(=O)_2NR^4-$, $(R^4)_2NS(=O)_2O-$, $(R^4)_2NS(=O)_2NR^4-$, $R^4S(=O)_2NR^4-$, $R^4S(=O)_2NHC(=O)-$, $R^4S(=O)_2NHC(=O)O-$, $R^4S(=O)_2NHC(=O)NR^4-$, $R^4OS(=O)_2NHC(=O)-$, $R^4OS(=O)_2NHC(=O)O-$, $R^4OS(=O)_2NHC(=O)NR^4-$, $(R^4)_2NS(=O)_2NHC(=O)-$, $(R^4)_2NS(=O)_2NHC(=O)O-$, $(R^4)_2NS(=O)_2NHC(=O)NR^4-$, $R^4C(=O)NHS(=O)_2-$, $R^4C(=O)NHS(=O)_2O-$, $R^4C(=O)NHS(=O)_2NR^4-$, $R^4OC(=O)NHS(=O)_2-$, $R^4OC(=O)NHS(=O)_2O-$, $R^4OC(=O)NHS(=O)_2NR^4-$, $(R^4)_2NC(=O)NHS(=O)_2-$, $(R^4)_2NC(=O)NHS(=O)_2O-$, $(R^4)_2NC(=O)NHS(=O)_2NR^4-$, aryl, cycloalkyl, heterocyclyl, heteroaryl, arylamino and heteroarylamino;

$A^1$ is (a) a bond, or (b) $(C_1-C_3)$alkylene, $CH_2CH_2O$, wherein the oxygen is attached to $Cy^1$, or $CH_2C(=O)$, wherein the carbonyl carbon is attached to $Cy^1$;

$Cy^1$ is aryl, heteroaryl, monocyclic cycloalkyl or monocyclic heterocyclyl and is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, $\{(C_3-C_6)$cycloalkyl$\}\{(C_1-C_6)$alkyl$\}$aminocarbonyl, di$(C_3-C_6)$cycloalkylaminocarbonyl, $(C_3-C_6)$cycloalkylaminosulfonyl, $\{(C_3-C_6)$cycloalkyl$\}\{(C_1-C_6)$alkyl$\}$aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, $\{(C_3-C_6)$cycloalkyl$\}\{(C_1-C_6)$alkyl$\}$aminocarbonyl$(C_1-C_6)$alkyl and di$(C_3-C_6)$cycloalkylaminocarbonyl$(C_1-C_6)$alkyl;

$A^2$ is (a) a bond, O, S or $NR^4$; or (b) $(C_1-C_3)$alkylene or $(C_1-C_2)$alkyleneoxy, each of which is optionally substituted with 1 to 4 groups independently selected from methyl, ethyl, trifluoromethyl or oxo;

$Cy^2$ is (a) hydrogen or (b) aryl, heteroaryl, cycloalkyl or heterocyclyl and is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkyl-alkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkyl-alkanesulfinyl, $(C_1-C_6)$alkanesulfonyl, $(C_3-C_6)$cycloalkanesulfonyl, $(C_4-C_7)$cycloalkyl-alkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkyl-aminosulfonyl, heterocyclosulfonyl, $(C_1-C_6)$alkylcarbonylamino, $(C_1-C_6)$alkylcarbonyl-amino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkylamino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, $\{(C_3-C_6)$cycloalkyl$\}\{(C_1-C_6)$alkyl$\}$aminocarbonyl, di$(C_3-C_6)$cycloalkylaminocarbonyl, $(C_3-C_6)$cycloalkylaminosulfonyl, $\{(C_3-C_6)$cycloalkyl$\}\{(C_1-C_6)$alkyl$\}$aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, $\{(C_3-C_6)$cycloalkyl$\}\{(C_1-C_6)$alkyl$\}$aminocarbonyl$(C_1-C_6)$alkyl and di$(C_3-C_6)$cycloalkylaminocarbonyl$(C_1-C_6)$alkyl;

Y is $(C_1-C_6)$alkyl or halo$(C_1-C_6)$alkyl;

n is 0, 1 or 2;

E is (a) a bond or (b) $(C_1-C_3)$alkylene or $(C_1-C_2)$alkylenyloxy, wherein the O is attached to $R^2$, each of which is optionally substituted with 1 to 4 groups independently selected from methyl, ethyl, trifluoromethyl or oxo;

$R^2$ is $(C_2-C_6)$alkyl, aryl, heteroaryl, cycloalkyl or heterocyclyl and is optionally substituted with up to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo ($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylthio, ($C_4$-$C_7$)cycloalkyl-alkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkyl-alkanesulfinyl, ($C_1$-$C_6$)alkanesulfonyl, ($C_3$-$C_6$)cycloalkanesulfonyl, ($C_4$-$C_7$)cycloalkyl-alkanesulfonyl, halo($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkyl-aminocarbonyl, heterocyclylcarbonyl, ($C_1$-$C_6$)alkylaminosulfonyl, di($C_1$-$C_6$)alkyl-aminosulfonyl, heterocyclosulfonyl, ($C_1$-$C_6$)alkylcarbonylamino, ($C_1$-$C_6$)alkylcarbonyl-amino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkylamino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy, ($C_1$-$C_6$)alkylcarbonyl, ($C_3$-$C_6$)cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl;

$R^3$ is selected from ($C_2$-$C_6$)alkyl, ($C_2$-$C_6$)alkenyl, ($C_2$-$C_6$)alkynyl, ($C_3$-$C_5$)cycloalkyl($C_1$-$C_4$)alkyl, ($C_1$-$C_3$)alkoxy($C_1$-$C_3$)alkoxy, or ($C_1$-$C_3$)alkoxy($C_1$-$C_3$)alkyl and is optionally substituted with up to four groups independently selected from fluorine, cyano, oxo, $R^4$, $R^4O$—, ($R^4)_2N$—, $R^4O_2C$—, $R^4C(=O)O$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, spirocycloalkyl; heterocyclyl (which in turn may be optionally substituted with alkyl, haloalkyl, halogen or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo);

$R^4$ is independently selected from H, ($C_1$-$C_6$)alkyl, halo($C_1$-$C_6$)alkyl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, hydroxy($C_1$-$C_6$)alkyl and ($C_1$-$C_6$)alkoxy($C_1$-$C_6$)alkyl; and or a pharmaceutically acceptable salt, enantiomer or diastereomer thereof.

In a second embodiment of the invention, Formula I and its constituent members are defined herein as follows:

$R^1$ is (a) absent or (b) is selected from ($C_1$-$C_6$)alkyl, ($C_2$-$C_6$)alkenyl, ($C_2$-$C_6$)alkynyl or ($C_1$-$C_3$)alkoxy($C_1$-$C_3$)alkyl, wherein each is optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, aryl, cycloalkyl, heterocyclyl, heteroaryl, arylamino and heteroarylamino;

$A^1$ is (a) a bond, or (b) ($C_1$-$C_3$)alkylene, $CH_2CH_2O$, wherein the oxygen is attached to $Cy^1$, or $CH_2C(=O)$, wherein the carbonyl carbon is attached to $Cy^1$;

$Cy^1$ is aryl, heteroaryl, monocyclic cycloalkyl or heterocyclyl, wherein each is optionally substituted with 1 to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)

alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy and ($C_1$-$C_6$)alkylcarbonyl;

$A^2$ is (a) a bond, O, S or $NR^4$; or (b) ($C_1$-$C_3$)alkylene or ($C_1$-$C_2$)alkyleneoxy, each of which is optionally substituted with 1 to 4 groups independently selected from methyl, ethyl, trifluoromethyl or oxo;

$Cy^2$ is (a) hydrogen or (b) aryl, heteroaryl, cycloalkyl or heterocyclyl, wherein each is optionally substituted with 1 to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkyl-aminosulfonyl, heterocyclsulfonyl, ($C_1$-$C_6$)alkylcarbonylamino, ($C_1$-$C_6$)alkylcarbonyl-amino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkylamino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy and ($C_1$-$C_6$)alkylcarbonyl;

Y is ($C_1$-$C_6$)alkyl or halo($C_1$-$C_6$)alkyl;

n is 0, 1 or 2;

E is (a) a bond or (b) ($C_1$-$C_3$)alkylene or ($C_1$-$C_2$)alkylenyloxy, wherein the O is attached to $R^2$, each of which is optionally substituted with 1 to 4 groups independently selected from methyl, ethyl, trifluoromethyl or oxo;

$R^2$ is ($C_2$-$C_6$)alkyl, aryl, heteroaryl, cycloalkyl or heterocyclyl, wherein each is optionally substituted with up to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkyl-alkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkyl-alkanesulfonyl, ($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkyl-aminocarbonyl, heterocyclylcarbonyl, ($C_1$-$C_6$)alkylaminosulfonyl, di($C_1$-$C_6$)alkyl-aminosulfonyl, heterocyclsulfonyl, ($C_1$-$C_6$)alkylcarbonylamino, ($C_1$-$C_6$)alkylcarbonyl-amino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkylamino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy and ($C_1$-$C_6$)alkylcarbonyl;

$R^3$ is selected from ($C_2$-$C_6$)alkyl, ($C_2$-$C_6$)alkenyl, ($C_2$-$C_6$)alkynyl and ($C_1$-$C_3$)alkoxy($C_1$-$C_3$)alkyl, wherein each is optionally substituted with up to four groups independently selected from fluorine, cyano, oxo, $R^4$, $R^4O-$, $(R^4)_2N-$, $R^4O_2C-$, $R^4S$, $R^4S(=O)-$, $R^4S(=O)_2-$, $R^4C(=O)NR^4$, $(R^4)_2NC(=O)-$, $(R^4)_2NC(=O)O-$, $(R^4)_2NC(=O)NR^4-$, $R^4OC(=O)NR^4-$, $(R^4)_2NC(=NCN)NR^4$, $(R^4O)_2P(=O)O-$, $(R^4O)_2P(=O)NR^4-$, $R^4OS(=O)_2NR^4-$, $(R^4)_2NS(=O)_2O-$, $(R^4)_2NS(=O)_2NR^4$, $R^4S(=O)_2NR^4-$, $R^4S(=O)_2NHC(=O)-$, $R^4S(=O)_2NHC(=O)O-$, $R^4S(=O)_2NHC(=O)NR^4$, $R^4OS(=O)_2NHC(=O)-$, $R^4OS(=O)_2NHC(=O)O-$, $R^4OS(=O)_2NHC(=O)NR^4$, $(R^4)_2NS(=O)_2NHC(=O)-$, $(R^4)_2NS(=O)_2NHC(=O)O-$, $(R^4)_2NS(=O)_2NHC(=O)NR^4$, $R^4C(=O)NHS(=O)_2-$, $R^4C(=O)NHS(=O)_2O-$, $R^4C(=O)NHS(=O)_2NR^4$, $R^4OC(=O)NHS(=O)_2-$, $R^4OC(=O)NHS(=O)_2O-$, $R^4OC(=O)NHS(=O)_2NR^4$, $(R^4)_2NC(=O)NHS(=O)_2-$, $(R^4)_2NC(=O)NHS(=O)_2O-$, $(R^4)_2NC(=O)NHS(=O)_2NR^4$, heterocyclyl (which in turn may be optionally substituted with alkyl, haloalkyl or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo);

$R^4$ is independently selected from H, ($C_1$-$C_6$)alkyl, halo($C_1$-$C_6$)alkyl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, hydroxy($C_1$-$C_6$)alkyl and ($C_1$-$C_6$)alkoxy($C_1$-$C_6$)alkyl;

or a pharmaceutically acceptable salt, enantiomer or diastereomer thereof.

Another embodiment of the invention is a method of treating a subject with diabetes comprising the step of administering to the subject in need of such treatment an effective amount of a compound of the structural formula I.

Another embodiment of the invention is a method of treating a subject with cardiovascular risk factors in a subject comprising the step of administering to the subject in need of such treatment an effective amount of a compound of the structural formula I.

Another embodiment of the invention is a method of treating a subject with anxiety and/or depression comprising the step of administering to the subject in need of such treatment an effective amount of a compound of the structural formula I.

Another embodiment of the invention is a method of treating a subject with glaucoma comprising the step of administering to the subject in need of such treatment an effective amount of a compound of the structural formula I.

Another embodiment of the invention is a method of treating a subject with osteoporosis in a subject comprising the step of administering to the subject in need of such treatment an effective amount of a compound of the structural formula I.

A third embodiment of the invention is a compound of Formula (I*):

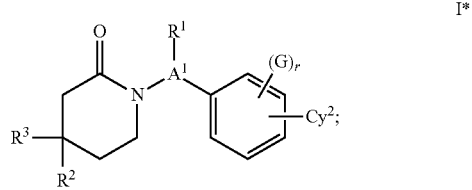

wherein $R^1$ is (a) absent or (b) is selected from $(C_1-C_6)$alkyl, optionally substituted with up to four groups independently selected from fluorine, cyano, oxo, $R^4$, $R^4O-$, $(R^4)_2N-$, $R^4O_2C-$, $R^4S$, $R^4S(=O)-$, $R^4S(=O)_2-$, $R^4C(=O)NR^4-$, $(R^4)_2NC(=O)-$, $(R^4)_2NC(=O)O-$, $(R^4)_2NC(=O)NR^4-$, $R^4OC(=O)NR^4-$, $(R^4)_2NC(=NCN)NR^4-$, $(R^4O)_2P(=O)O-$, $(R^4O)_2P(=O)NR^4-$, $R^4OS(=O)_2NR^4-$, $(R^4)_2NS(=O)_2O-$, $(R^4)_2NS(=O)_2NR^4-$, $R^4S(=O)_2NR^4-$, $R^4S(=O)_2NHC(=O)-$, $R^4S(=O)_2NHC(=O)O-$, $R^4S(=O)_2NHC(=O)NR^4-$, $R^4OS(=O)_2NHC(=O)-$, $R^4OS(=O)_2NHC(=O)O-$, $R^4OS(=O)_2NHC(=O)NR^4-$, $(R^4)_2NS(=O)_2NHC(=O)-$, $(R^4)_2NS(=O)_2NHC(=O)O-$, $(R^4)_2NS(=O)_2NHC(=O)NR^4-$, $R^4C(=O)NHS(=O)_2-$, $R^4C(=O)NHS(=O)_2O-$, $R^4C(=O)NHS(=O)_2NR^4-$, $R^4OC(=O)NHS(=O)_2-$, $R^4OC(=O)NHS(=O)_2O-$, $R^4OC(=O)NHS(=O)_2NR^4-$, $(R^4)_2NC(=O)NHS(=O)_2-$, $(R^4)_2NC(=O)NHS(=O)_2O-$, $(R^4)_2NC(=O)NHS(=O)_2NR^4-$, aryl, cycloalkyl, heterocyclyl, heteroaryl, arylamino and heteroarylamino;

$A^1$ is (a) a bond, or (b) $(C_1-C_3)$alkylene;

r is 0, 1, 2, 3 or 4;

G is independently selected from fluorine, chlorine, bromine, iodine, cyano, nitro, amino, hydroxy, $(C_1-C_6)$alkyl, hydroxy$(C_1-C_6)$alkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, oxo, amino$(C_1-C_6)$alkyl, $(C_1-C_6)$alkylamino$(C_1-C_6)$alkyl, di$(C_1-C_6)$alkylamino$(C_1-C_6)$alkylamino$(C_2-C_6)$alkoxy, $(C_1-C_6)$alkylamino$(C_2-C_6)$alkoxy, di$(C_1-C_6)$alkylamino$(C_2-C_6)$alkoxy and $(C_1-C_6)$alkylcarbonyl; and G is also selected from $(C_3-C_6)$cycloalkyl; hydroxy$(C_3-C_6)$cycloalkyl, halo$(C_3-C_6)$cycloalkyl, heteroaryl when G is attached meta or para to $A^1$;

$Cy^2$ is (a) hydrogen or (b) aryl, heteroaryl, cycloalkyl or heterocyclyl, wherein each is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkyl-aminosulfonyl, heterocyclsulfonyl, $(C_1-C_6)$alkylcarbonylamino, $(C_1-C_6)$alkylcarbonyl-amino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkylamino$(C_2-C_6)$alkoxy, $(C_1-C_6)$alkylamino$(C_2-C_6)$alkoxy, di$(C_1-C_6)$alkylamino$(C_2-C_6)$alkoxy and $(C_1-C_6)$alkylcarbonyl;

$R^2$ is phenyl optionally substituted with up to 4 groups independently selected from fluorine, chlorine, bromine, iodine, cyano, nitro, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkyl-carbonylamino($C_1$-$C_6$)alkyl, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkylamino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy and ($C_1$-$C_6$)alkylcarbonyl;

$R^3$ is substituted $O_2$ alkyl or optionally substituted ($C_3$-$C_6$)alkyl, wherein each substituted group represented by $R^3$ has up to two substituent groups which are independently selected from cyano, oxo, $R^4O$—, $(R^4)_2N$—, $R^4O_2C$—, $R^4S$, $R^4S(=O)$—, $R^4S(=O)_2$—, $R^4C(=O)NR^4$, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$, $R^4S(=O)_2NR^4$—, $R^4S(=O)_2NHC(=O)$—, $R^4S(=O)_2NHC(=O)O$—, $R^4S(=O)_2NHC(=O)NR^4$, $R^4OS(=O)_2NHC(=O)$—, $R^4OS(=O)_2NHC(=O)O$—, $R^4OS(=O)_2NHC(=O)NR^4$, $(R^4)_2NS(=O)_2NHC(=O)$—, $(R^4)_2NS(=O)_2NHC(=O)O$—, $(R^4)_2NS(=O)_2NHC(=O)NR^4$, $R^4C(=O)NHS(=O)_2$—, $R^4C(=O)NHS(=O)_2O$—, $R^4C(=O)NHS(=O)_2NR^4$, $R^4OC(=O)NHS(=O)_2$—, $R^4OC(=O)NHS(=O)_2O$—, $R^4OC(=O)NHS(=O)_2NR^4$, $(R^4)_2NC(=O)NHS(=O)_2$—, $(R^4)_2NC(=O)NHS(=O)_2O$—, $(R^4)_2NC(=O)NHS(=O)_2NR^4$, heterocyclyl (which in turn may be optionally substituted with alkyl, haloalkyl or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo);

$R^4$ is independently selected from H, ($C_1$-$C_6$)alkyl, halo($C_1$-$C_6$)alkyl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, hydroxy($C_1$-$C_6$)alkyl and ($C_1$-$C_6$)alkoxy($C_1$-$C_6$)alkyl;

provided that if E is a bond or $C_1$alkylene, $R_2$ is aryl, heteroaryl or heterocyclyl, $A^1$ is ($C_1$)alkylene, $R^3$ is optionally fluorinated ($C_1$-$C_5$)alkyl, ($C_2$-$C_5$)alkenyl or ($C_2$-$C_6$)alkynyl and $Cy^1$ is optionally substituted phenyl, then $Cy^1$ is not substituted at the ortho position by optionally substituted aryl, heteroaryl, heterocyclyl or cycloalkyl;

or a pharmaceutically acceptable salt, enantiomer or diastereomer thereof.

Another embodiment of the invention is a method of treating a subject with diabetes comprising the step of administering to the subject in need of such treatment an effective amount of a compound of the structural formula I, wherein $A^2$ is (a) a bond, O or S; or (b) ($C_2$-$C_3$)alkylene or ($C_1$-$C_2$)alkyleneoxy, each of which is optionally substituted with 1 to 4 groups independently selected from methyl, ethyl, trifluoromethyl or oxo;

$R^2$ is ($C_1$-$C_6$)alkyl, aryl, heteroaryl, cycloalkyl or heterocyclyl, wherein each is optionally substituted with up to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkyl-alkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkyl-alkanesulfonyl, halo($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkyl-aminocarbonyl, heterocyclylcarbonyl, ($C_1$-$C_6$)alkylaminosulfonyl, di($C_1$-$C_6$)alkyl-aminosulfonyl, heterocyclsulfonyl, ($C_1$-$C_6$)alkylcarbonylamino, ($C_1$-$C_6$)alkylcarbonyl-amino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkylamino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy and ($C_1$-$C_6$)alkylcarbonyl;

$R^3$ is selected from ($C_1$-$C_6$)alkyl, ($C_2$-$C_6$)alkenyl, ($C_2$-$C_6$)alkynyl; and ($C_1$-$C_3$)alkoxy($C_2$-$C_3$)alkyl, wherein each is optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$, $R^4S(=O)_2NR^4$—, $R^4S(=O)_2NHC(=O)$—, $R^4S(=O)_2NHC(=O)O$—, $R^4S(=O)_2NHC(=O)NR^4$, $R^4OS(=O)_2NHC(=O)$—, $R^4OS(=O)_2NHC(=O)O$—, $R^4OS(=O)_2NHC(=O)NR^4$, $(R^4)_2NS(=O)_2NHC(=O)$—, $(R^4)_2NS(=O)_2NHC(=O)O$—, $(R^4)_2NS(=O)_2NHC(=O)NR^4$, $R^4C(=O)NHS(=O)_2$—, $R^4C(=O)NHS(=O)_2O$—, $R^4C(=O)NHS(=O)_2NR^4$, $R^4OC(=O)NHS(=O)_2$—, $R^4OC(=O)NHS(=O)_2O$—, $R^4OC(=O)NHS(=O)_2NR^4$, $(R^4)_2NC(=O)NHS(=O)_2$—, $(R^4)_2NC(=O)NHS(=O)_2O$—, $(R^4)_2NC(=O)NHS(=O)_2NR^4$, heterocyclyl (which in turn may be optionally substituted with alkyl, haloalkyl or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo);

and the remainder of the variables are as described above; provided that if E is a bond or $C_1$alkylene, $R_2$ is aryl, heteroaryl or heterocyclyl, A' is ($C_1$)alkylene, $R^3$ is optionally fluorinated ($C_1$-$C_5$)alkyl, ($C_2$-$C_5$)alkenyl or ($C_2$-$C_6$)alkynyl and $Cy^1$ is optionally substituted phenyl, then $Cy^1$ is not substituted at the ortho position by optionally substituted aryl, heteroaryl, heterocyclyl or cycloalkyl.

Another embodiment of the invention is a method of treating a subject with cardiovascular disease comprising the step of administering to the subject an effective amount of a compound of the structural formula I; wherein $A^1$ is (a) a bond, or (b) ($C_1$alkylene, $CH_2CH_2O$, wherein the oxygen is attached to $Cy^1$, or $CH_2C(=O)$), wherein the carbonyl carbon is attached to $Cy^1$;

$A^2$ is (a) a bond, O or S or; (b) ($C_2$-$C_3$)alkylene or ($C_1$-$C_2$) alkyleneoxy, each of which is optionally substituted with 1 to 4 groups independently selected from methyl, ethyl; trifluoromethyl or oxo;

$R^2$ is ($C_2$-$C_6$)alkyl, aryl, heteroaryl, cycloalkyl or heterocyclyl, wherein each is optionally substituted with up to 4 groups independently selected from fluorine, chlorine, bromine, iodine, cyano, nitro, amino, hydroxy, carboxy, ($C_1$-$C_6$) alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$) alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$) cycloalkylalkoxy, ($C_1$-$C_6$)alkylthio, ($C_3$-$C_6$)cycloalkythio, ($C_4$-$C_7$)cycloalkyl-alkylthio, halo($C_1$-$C_6$)alkylthio, halo($C_3$-$C_6$)cycloalkythio, halo($C_4$-$C_7$)cycloalkylalkylthio, ($C_1$-$C_6$) alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkyl-alkanesulfinyl, ($C_1$-$C_6$)alkanesulfonyl, ($C_3$-$C_6$) cycloalkanesulfonyl, ($C_4$-$C_7$)cycloalkyl-alkanesulfonyl, halo($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$) alkylaminocarbonyl, ($C_1$-$C_3$)alkoxy($C_1$-$C_3$)alkyl-aminocarbonyl, heterocyclylcarbonyl, ($C_1$-$C_6$)alkylaminosulfonyl, di($C_1$-$C_6$)alkyl-aminosulfonyl, heterocyclsulfonyl, ($C_1$-$C_6$) alkylcarbonylamino, ($C_1$-$C_6$)alkylcarbonyl-amino($C_1$-$C_6$) alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$) alkyl, hydroxy($C_1$-$C_6$)alkoxy, heteroaryl, oxo, amino($C_1$-$C_6$) alkyl, ($C_1$-$C_6$)alkylamino($C_1$-$C_6$)alkyl, di($C_1$-$C_6$)alkylamino($C_1$-$C_6$)alkylamino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy and ($C_1$-$C_6$) alkylcarbonyl;

$R^3$ is selected from ($C_2$-$C_6$)alkyl, ($C_2$-$C_6$)alkenyl, ($C_2$-$C_6$) alkynyl; and ($C_1$-$C_3$)alkoxy($C_2$-$C_3$)alkyl, wherein each is optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$, $R^4S(=O)_2NR^4$—, $R^4S(=O)_2NHC(=O)$—, $R^4S(=O)_2NHC(=O)O$—, $R^4S(=O)_2NHC(=O)NR^4$, $R^4OS(=O)_2NHC(=O)$—, $R^4OS(=O)_2NHC(=O)O$—, $R^4OS(=O)_2NHC(=O)NR^4$, $(R^4)_2NS(=O)_2NHC(=O)$—, $(R^4)_2NS(=O)_2NHC(=O)O$—, $(R^4)_2NS(=O)_2NHC(=O)NR^4$, $R^4C(=O)NHS(=O)_2$—, $R^4C(=O)NHS(=O)_2O$—, $R^4C(=O)NHS(=O)_2NR^4$, $R^4OC(=O)NHS(=O)_2$—, $R^4OC(=O)NHS(=O)_2O$—, $R^4OC(=O)NHS(=O)_2NR^4$, $(R^4)_2NC(=O)NHS(=O)_2$—, $(R^4)_2NC(=O)NHS(=O)_2O$—, $(R^4)_2NC(=O)NHS(=O)_2NR^4$, heterocyclyl (which in turn may be optionally substituted with alkyl, haloalkyl or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo);

provided that if E is a bond or $C_1$alkylene, $R_2$ is aryl, heteroaryl or heterocyclyl, A' is ($C_1$)alkylene, $R^3$ is optionally fluorinated ($C_1$-$C_5$)alkyl, ($C_2$-$C_5$)alkenyl or ($C_2$-$C_6$)alkynyl and $Cy^1$ is optionally substituted phenyl, then $Cy^1$ is not substituted at the ortho position by optionally substituted aryl, heteroaryl, heterocyclyl or cycloalkyl; and provided that if $A_1$ and $A_2$ are both a bond and $Cy_1$ is piperidinyl, then $Cy_2$ is not optionally substituted quinazolin-4-amine;

and the remainder of the values are as described for Structural formula I.

Another embodiment of the invention is a method of treating a subject with anxiety and/or depression in a subject comprising the step of administering to the subject in need of such treatment an effective amount of a compound of the structural formula I; wherein $Cy^1$ is aryl, 2- or 3-thienyl, 2- or 3-furanyl, 2- or 3-pyrrolyl, 2-, 3-, or 4-pyridyl, 2-pyrazinyl, 2-, 4-, or 5-pyrimidinyl, 3- or 4-pyridazinyl, 1H-benzimidazol-6-yl, 1H-benzimidazol-5-yl, 2-, 4-, 5-, 6-, 7- or 8-quinazolinyl, 2-, 3-, 5-, 6-, 7- or 8-quinoxalinyl, 2-, 3-, 4-, 5-, 6-, 7- or 8-quinolinyl, 1-, 3-, 4-, 5-, 6-, 7- or 8-isoquinolinyl, 2-, 4-, or 5-thiazolyl, 2-, 3-, 4-, or 5-pyrazolyl, 2-, 3-, 4-, or 5-imidazolyl, monocyclic cycloalkyl or heterocyclyl, wherein each is optionally substituted with 1 to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$) alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$) cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkyl-carbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkylamino$(C_2-C_6)$alkoxy, $(C_1-C_6)$alkylamino$(C_2-C_6)$alkoxy, di$(C_1-C_6)$alkylamino$(C_2-C_6)$alkoxy and $(C_1-C_6)$alkylcarbonyl;

$A^2$ is (a) a bond, O, S or $NR^4$; or (b) $(C_1-C_3)$alkylene or $(C_1-C_2)$alkyleneoxy, each of which is optionally substituted with 1 to 4 groups independently selected from methyl, ethyl, or trifluoromethyl;

E is (a) a bond or (b) $(C_1-C_2)$alkylenyloxy, wherein the O is attached to $R^2$, optionally substituted with 1 to 4 groups independently selected from methyl, ethyl, trifluoromethyl or oxo;

$R^2$ is aryl, heteroaryl, cycloalkyl or heterocyclyl, wherein each is optionally substituted with up to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkyl-alkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkyl-alkanesulfinyl, $(C_1-C_6)$alkanesulfonyl, $(C_3-C_6)$cycloalkanesulfonyl, $(C_4-C_7)$cycloalkyl-alkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkyl-aminocarbonyl, heterocyclylcarbonyl, $(C_1-C_6)$alkylaminosulfonyl, di$(C_1-C_6)$alkyl-aminosulfonyl, heterocyclsulfonyl, $(C_1-C_6)$alkylcarbonylamino, $(C_1-C_6)$alkylcarbonyl-amino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkylamino$(C_2-C_6)$alkoxy, $(C_1-C_6)$alkylamino$(C_2-C_6)$alkoxy, di$(C_1-C_6)$alkylamino$(C_2-C_6)$alkoxy and $(C_1-C_6)$alkylcarbonyl;

$R^3$ is selected from $(C_1-C_6)$alkyl, $(C_2-C_6)$alkenyl, $(C_2-C_6)$alkynyl; and $(C_1-C_3)$alkoxy$(C_2-C_3)$alkyl, wherein each is optionally substituted with up to four groups independently selected from fluorine, cyano, oxo, $R^4$, $R^4O-$, $(R^4)_2N-$, $R^4O_2C-$, $R^4S$, $R^4S(=O)-$, $R^4S(=O)_2-$, $R^4C(=O)NR^4$, $(R^4)_2NC(=O)-$, $(R^4)_2NC(=O)O-$, $(R^4)_2NC(=O)NR^4-$, $R^4OC(=O)NR^4-$, $(R^4)_2NC(=NCN)NR^4$, $(R^4O)_2P(=O)O-$, $(R^4O)_2P(=O)NR^4$, $R^4OS(=O)_2NR^4-$, $(R^4)_2NS(=O)_2O-$, $(R^4)_2NS(=O)_2NR^4$, $R^4S(=O)_2NR^4-$, $R^4S(=O)_2NHC(=O)-$, $R^4S(=O)_2NHC(=O)O-$, $R^4S(=O)_2NHC(=O)NR^4$, $R^4OS(=O)_2NHC(=O)-$, $R^4OS(=O)_2NHC(=O)O-$, $R^4OS(=O)_2NHC(=O)NR^4$, $(R^4)_2NS(=O)_2NHC(=O)-$, $(R^4)_2NS(=O)_2NHC(=O)O-$, $(R^4)_2NS(=O)_2NHC(=O)NR^4$, $R^4C(=O)NHS(=O)_2-$, $R^4C(=O)NHS(=O)_2O-$, $R^4C(=O)NHS(=O)_2NR^4$, $R^4OC(=O)NHS(=O)_2-$, $R^4OC(=O)NHS(=O)_2O-$, $R^4OC(=O)NHS(=O)_2NR^4$, $(R^4)_2NC(=O)NHS(=O)_2-$, $(R^4)_2NC(=O)NHS(=O)_2O-$, $(R^4)_2NC(=O)NHS(=O)_2NR^4$, heterocyclyl (which in turn may be optionally substituted with alkyl, haloalkyl or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo);

and the remainder of the values are as described for Structural formula I.

Another embodiment of the invention is a method of treating a subject with glaucoma comprising the step of administering to the subject in need of such treatment an effective amount of a compound of the structural formula I; wherein $A^1$ is (a) a bond, or (b) $(C_1)$alkylene, $CH_2CH_2O$, wherein the oxygen is attached to $Cy^1$, or $CH_2C(=O)$, wherein the carbonyl carbon is attached to $Cy^1$;

$Cy^1$ is aryl, heteroaryl, monocyclic cycloalkyl or heterocyclyl, wherein each is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkylamino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy and ($C_1$-$C_6$)alkylcarbonyl;

$A^2$ is (a) a bond, O, S or $NR^4$; or (b) ($C_1$-$C_3$)alkylene or ($C_1$-$C_2$)alkyleneoxy, each of which is optionally substituted with 1 to 4 groups independently selected from methyl, ethyl, or trifluoromethyl;

$Cy^1$ is aryl, heteroaryl, monocyclic cycloalkyl or heterocyclyl, wherein each is optionally substituted with 1 to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkane-sulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkane-sulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2$NCO, $H_2NSO_2$, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkylamino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy and ($C_1$-$C_6$)alkylcarbonyl;

$A^2$ is (a) a bond, O, S or $NR^4$; or (b) ($C_1$-$C_3$)alkylene or ($C_1$-$C_2$)alkyleneoxy, each of which is optionally substituted with 1 to 4 groups independently selected from methyl, ethyl, or trifluoromethyl;

and the remainder of the values are as described for Structural formula I.

Another embodiment of the invention is a method of treating osteoporosis in a subject comprising the step of administering to the subject in need of such treatment an effective amount of a compound of the structural formula I; wherein $A^2$ is (a) a bond, O or S; or (b) ($C_1$-$C_3$)alkylene or ($C_1$-$C_2$)alkyleneoxy, each of which is optionally substituted with 1 to 4 groups independently selected from methyl, ethyl, trifluoromethyl or oxo;

and the remainder of the values are as described for Structutral formula I.

DETAILED DESCRIPTION OF THE INVENTION

A fourth embodiment is a compound of Formula I or any one of Formulas Ia-g wherein:

$R^1$ is absent or is methyl or ethyl;
$A^1$ is a bond or $CH_2$ or if $R^1$ is present, then $A^1$ is CH;
$Cy^1$ is phenyl, cyclopropyl, cyclohexyl, pyrrolidinyl, pyridyl, N-oxo-pyridyl, thiazolyl or pyrimidinyl optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, t-butoxycarbonyl, hydroxy, hydroxymethyl, 2-hydroxyethyl, 2-hydroxy-2-propyl, methoxymethyl, methylsulfonyl and methylsulfonylamino;
$A^2$ is a bond, O, $OCH_2CO$ or C=O;
$Cy^2$ is (a) hydrogen or (b) phenyl, thienyl, pyridyl, N-oxopyridyl, cyclopropyl, piperidinyl, piperazinyl, morpholinyl, thiazolyl, oxadiazolyl, thiadiazolyl, pyrazolyl, S,S-dioxothiazinyl, 2-oxo-1,2-dihydropyridyl optionally substituted by 1 to 4 groups independently selected from halo, hydroxy, methoxy, hydroxymethyl, methoxycarbonyl, amino, carbamoyl, methylcarbamoyl, dimethylcarbamoyl, (2-methoxyethyl)aminocarbonyl, acetylamino-methyl, methylsulfonyl, methylsulfonylamino, methylaminosulfonyl, isopropylamino-sulfonyl, dimethylaminosulfonyl, pyrrolidine-1-sulfonyl, methylsulfonylaminomethyl, tetrazolyl, methyl, trifluoromethyl, acetyl, 2-hydroxyethyl and 1-aminoethyl;
n is 0;
E is a bond or $CH_2$;
$R^2$ is isopropyl, thienyl, phenyl, or pyridyl, each optionally substituted with halo, methyl, methylthio or (4-morpholino)methyl;
$R^3$ is methyl, ethyl, propyl, butyl, vinyl, allyl or ethoxyethyl, each optionally substituted with up to two groups independently selected from HO—, MeO—, $H_2$N—, MeC(=O)NH—, MeS(=O)$_2$NH—, $H_2$NC(=O)—, MeNHC(=O)—, $HO_2$C—, $(HO)_2$P(=O)O—, $H_2$NS(=O)$_2$O—, $H_2$NS(=O)$_2$NH—, MeNHC(=O)NH—, MeNHC(=O)O— oxo, cyano, $HO_2$C—, $HOCH_2CH_2$NH—, 4-morpholino, $HOCH_2$C(=O)NH—, $H_2NCH_2$C(=O)NH—, EtNHC(=O)NH, MeOC(=O)NH—, MeNHC(=NC=N)NH—, Me-, MeS—, $MeSO_2$-$MeSO_2$N(Me)-, MeS(=O)$_2$NHC(=O)—, imidazolylamino-, imidazolyl, tetrazolyl, $H_2$NCONH—, $H_2$NCO$_2$—, $HOCH_2CH_2$O—, MeNH—, $Me_2$N— and MeCONMe.

Another embodiment is a compound of Formula Ia:

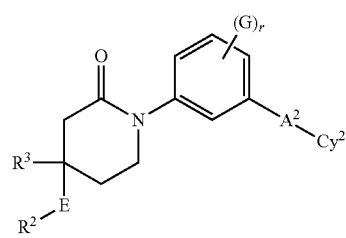

Ia wherein $A^2$, $Cy^2$, E, $R^2$ and $R^3$ are as defined for Formula I above; r is 0, 1, 2, 3 or 4; and substituents G are independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)

cycloalkylalkoxy, (C₁-C₆)alkylthio, (C₃-C₆)cycloalkythio, (C₄-C₇)cycloalkylalkylthio, halo(C₁-C₆)alkylthio, halo(C₃-C₆)cycloalkythio, halo(C₄-C₇)cycloalkylalkylthio, (C₁-C₆)alkanesulfinyl, (C₃-C₆)cycloalkanesulfinyl, (C₄-C₇)cycloalkylalkanesulfinyl, halo(C₁-C₆)alkane-sulfinyl, halo(C₃-C₆)cycloalkanesulfinyl, halo(C₄-C₇)cycloalkylalkanesulfinyl, (C₁-C₆)alkanesulfonyl, (C₃-C₆)cycloalkanesulfonyl, (C₄-C₇)cycloalkylalkanesulfonyl, halo(C₁-C₆)alkanesulfonyl, halo(C₃-C₆)cycloalkane-sulfonyl, halo(C₄-C₇)cyclo-alkylalkanesulfonyl, (C₁-C₆)alkylamino, di(C₁-C₆)alkylamino, (C₁-C₆)alkoxy(C₁-C₆)alkoxy, halo(C₁-C₆)alkoxy(C₁-C₆)alkoxy, (C₁-C₆)alkoxycarbonyl, H₂NCO, H₂NSO₂, (C₁-C₆)alkylaminocarbonyl, di(C₁-C₆)alkylaminocarbonyl, (C₁-C₃)alkoxy(C₁-C₃)alkylaminocarbonyl, heterocyclylcarbonyl, (C₁-C₆)alkylaminosulfonyl, di(C₁-C₆)alkylaminosulfonyl, heterocyclsulfonyl, (C₁-C₆)alkylcarbonylamino, (C₁-C₆)alkylcarbonylamino(C₁-C₆)alkyl, (C₁-C₆)alkylsulfonylamino, (C₁-C₆)alkylsulfonylamino-(C₁-C₆)alkyl, (C₁-C₆)alkoxycarbonyl(C₁-C₆)alkoxy, (C₁-C₆)alkoxy(C₁-C₆)alkyl, halo(C₁-C₆)alkoxy(C₁-C₆)alkyl, hydroxy(C₁-C₆)alkoxy, heteroaryl, amino(C₁-C₆)alkyl, (C₁-C₆)alkylamino(C₁-C₆)alkyl, di(C₁-C₆)alkylamino(C₁-C₆)alkylamino(C₂-C₆)alkoxy, (C₁-C₆)alkylamino(C₂-C₆)alkoxy, di(C₁-C₆)alkylamino(C₂-C₆)alkoxy or (C₁-C₆)alkylcarbonyl;

or a pharmaceutically acceptable salt, enantiomer or diastereomer thereof.

Another embodiment is a compound of Formula Ib:

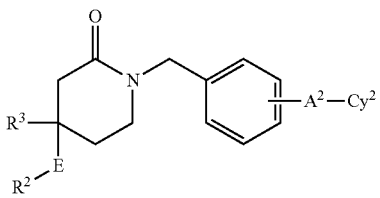

Ib wherein A², Cy², E, R² and R³ are as defined for Formula I above;

or a pharmaceutically acceptable salt, enantiomer or diastereomer thereof.

Another embodiment is a compound of Formula Ic:

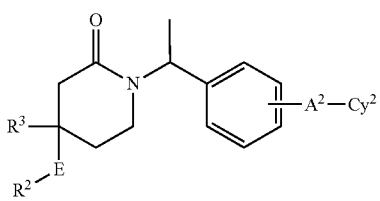

Ic wherein A², Cy², E, R², and R³ are as defined for Formula I above;

or a pharmaceutically acceptable salt, enantiomer or diastereomer thereof.

Another embodiment is a compound of Formula Id:

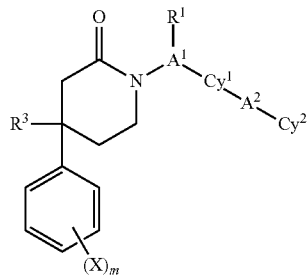

Id wherein A¹, R¹, Cy¹, A², Cy² and R³ are as defined for Formula I above; m is 0, 1, 2, 3 or 4; and substituents X are independently selected from fluorine, chlorine, bromine, iodine, cyano, nitro, amino, hydroxy, carboxy, (C₁-C₆)alkyl, hydroxy(C₁-C₆)alkyl, (C₃-C₆)cycloalkyl, hydroxy(C₃-C₆)cycloalkyl, (C₄-C₇)cycloalkylalkyl, (C₂-C₆)alkenyl, halo(C₂-C₆)alkenyl, hydroxy(C₂-C₆)alkenyl, (C₂-C₆)alkynyl, (C₃-C₆)cycloalkyl(C₂-C₄)alkynyl, halo(C₁-C₆)alkyl, halo(C₃-C₆)cycloalkyl, halo(C₄-C₇)cycloalkylalkyl, (C₁-C₆)alkoxy, (C₃-C₆)cycloalkoxy, (C₄-C₇)cycloalkylalkoxy, halo(C₁-C₆)alkoxy, halo(C₃-C₆)cycloalkoxy, halo(C₄-C₇)cycloalkylalkoxy, (C₁-C₆)alkylthio, (C₃-C₆)cycloalkythio, (C₄-C₇)cycloalkyl-alkylthio, halo(C₁-C₆)alkylthio, halo(C₃-C₆)cycloalkythio, halo(C₄-C₇)cycloalkylalkylthio, (C₁-C₆)alkanesulfinyl, (C₃-C₆)cycloalkanesulfinyl, (C₄-C₇)cycloalkylalkanesulfinyl, halo(C₁-C₆)alkane-sulfinyl, halo(C₃-C₆)cycloalkanesulfinyl, halo(C₄-C₇)cycloalkyl-alkanesulfinyl, (C₁-C₆)alkanesulfonyl, (C₃-C₆)cycloalkanesulfonyl, (C₄-C₇)cycloalkyl-alkanesulfonyl, halo(C₁-C₆)alkanesulfonyl, halo(C₃-C₆)cycloalkanesulfonyl, halo(C₄-C₇)cyclo-alkylalkanesulfonyl, (C₁-C₆)alkylamino, di(C₁-C₆)alkylamino, (C₁-C₆)alkoxy(C₁-C₆)alkoxy, halo(C₁-C₆)alkoxy(C₁-C₆)alkoxy, (C₁-C₆)alkoxycarbonyl, H₂NCO, H₂NSO₂, (C₁-C₆)alkylaminocarbonyl, di(C₁-C₆)alkylaminocarbonyl, (C₁-C₃)alkoxy(C₁-C₃)alkylaminocarbonyl, heterocyclylcarbonyl, (C₁-C₆)alkylaminosulfonyl, di(C₁-C₆)alkyl-aminosulfonyl, heterocyclsulfonyl, (C₁-C₆)alkylcarbonylamino, (C₁-C₆)alkylcarbonyl-amino(C₁-C₆)alkyl, (C₁-C₆)alkylsulfonylamino, (C₁-C₆)alkylsulfonylamino(C₁-C₆)alkyl, (C₁-C₆)alkoxycarbonyl(C₁-C₆)alkoxy, (C₁-C₆)alkoxy(C₁-C₆)alkyl, halo(C₁-C₆)alkoxy(C₁-C₆)alkyl, hydroxy(C₁-C₆)alkoxy, heteroaryl, amino(C₁-C₆)alkyl, (C₁-C₆)alkylamino(C₁-C₆)alkyl, di(C₁-C₆)alkylamino(C₁-C₆)alkylamino(C₂-C₆)alkoxy, (C₁-C₆)alkylamino(C₂-C₆)alkoxy, di(C₁-C₆)alkylamino(C₂-C₆)alkoxy and (C₁-C₆)alkylcarbonyl;

or a pharmaceutically acceptable salt, enantiomer or diastereomer thereof.

In a specific embodiment, A²-Cy² is meta or para to the carbon atom bonded to -A₁.

Another embodiment is a compound of Formula Ie:

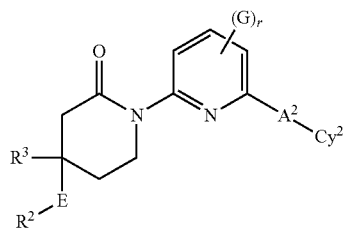

Ie wherein $A^2$, $Cy^2$, E, $R^2$ and $R^3$ are as defined for Formula I above, r is 0, 1, 2, 3 or 4; and substituents G are independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkyl-alkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkyl-alkanesulfinyl, $(C_1-C_6)$alkanesulfonyl, $(C_3-C_6)$cycloalkanesulfonyl, $(C_4-C_7)$cycloalkyl-alkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkyl-aminocarbonyl, heterocyclylcarbonyl, $(C_1-C_6)$alkylaminosulfonyl, di$(C_1-C_6)$alkylamino-sulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxy-carbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkylamino$(C_2-C_6)$alkoxy, $(C_1-C_6)$alkylamino$(C_2-C_6)$alkoxy, di$(C_1-C_6)$alkylamino$(C_2-C_6)$alkoxy and $(C_1-C_6)$alkylcarbonyl;

or a pharmaceutically acceptable salt, enantiomer or diastereomer thereof.

Another embodiment is a compound of Formula If:

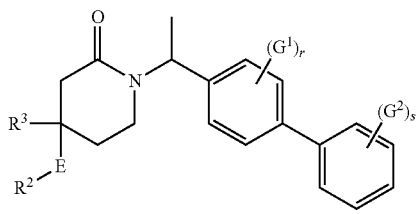

If wherein E, $R^2$ and $R^3$ are as defined for Formula I above, r and s are independently 0, 1, 2, 3 or 4; and $G^1$ and $G^2$ are independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkyl-alkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkyl-aminocarbonyl, heterocyclylcarbonyl, $(C_1-C_6)$alkylaminosulfonyl, di$(C_1-C_6)$alkylamino-sulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxy-carbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkylamino$(C_2-C_6)$alkoxy, $(C_1-C_6)$alkylamino$(C_2-C_6)$alkoxy, di$(C_1-C_6)$alkylamino$(C_2-C_6)$alkoxy and $(C_1-C_6)$alkylcarbonyl;

or a pharmaceutically acceptable salt, enantiomer or diastereomer thereof.

Yet another embodiment is a compound of the structural formula (If*):

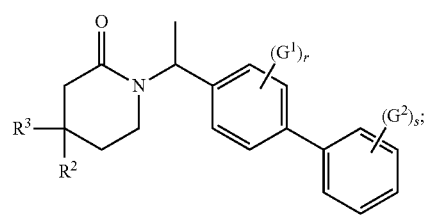

If* wherein
r and s are independently 0, 1, 2, 3 or 4; and
$G^1$ and $G^2$ are independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkyl-aminocarbonyl, heterocyclylcarbonyl, $(C_1-C_6)$alkylaminosulfonyl, di$(C_1-C_6)$alkylamino-sulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxy-carbonyl$(C_1-C_6)$alkoxy, $(C_1-C_6)$alkoxy$(C_1-C_6)$alkyl, halo$(C_1-C_6)$alkoxy$(C_1-C_6)$ alkyl, hydroxy($C_1$-$C_6$)alkoxy, heteroaryl, amino($C_1$-$C_6$)alkyl, ($C_1$-$C_6$)alkylamino($C_1$-$C_6$)alkyl, di($C_1$-$C_6$)alkylamino($C_1$-$C_6$)alkylamino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy and ($C_1$-$C_6$)alkylcarbonyl;

or a pharmaceutically acceptable salt, enantiomer or diastereomer thereof.

Another embodiment is a compound of Formula Ig:

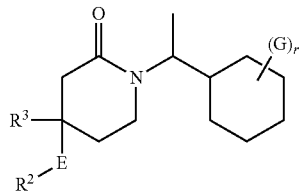

Ig wherein E, $R^2$ and $R^3$ are as defined for Formula I above, r is 0, 1, 2, 3 or 4; and substituents G are independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkyl-alkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkyl-alkanesulfinyl, ($C_1$-$C_6$)alkanesulfonyl, ($C_3$-$C_6$)cycloalkanesulfonyl, ($C_4$-$C_7$)cycloalkyl-alkanesulfonyl, halo($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkyl-aminocarbonyl, heterocyclylcarbonyl, ($C_1$-$C_6$)alkylaminosulfonyl, di($C_1$-$C_6$)alkylamino-sulfonyl, heterocyclsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxy-carbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, amino($C_1$-$C_6$)alkyl, ($C_1$-$C_6$)alkylamino($C_1$-$C_6$)alkyl, di($C_1$-$C_6$)alkylamino($C_1$-$C_6$)alkylamino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy and ($C_1$-$C_6$)alkylcarbonyl;

or a pharmaceutically acceptable salt, enantiomer or diastereomer thereof.

Another embodiment is a compound of Formula Ih:

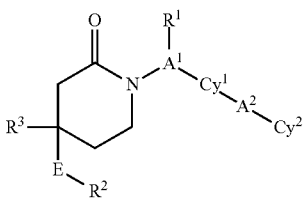

Ih

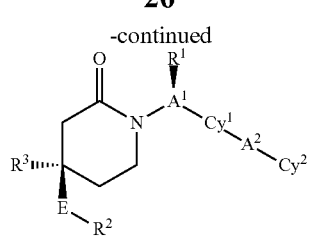

wherein, $Cy^1$, $A^1$, $R^1$, $A^2$, $Cy^2$, $R^2$, E and $R^3$ are as defined for the first, second, third or fourth embodiments described for Formula I above and at least one and preferably both stereocenters are in the configuration depicted.

Another embodiment is a compound of Formula Ii:

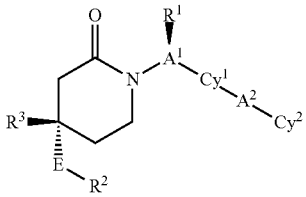

Ii wherein, $Cy^1$, $A^1$, $R^1$, $A^2$, $Cy^2$, $R^2$, E and $R^3$ are as defined for the first, second, third or fourth embodiments described for Formula I above and at least one and preferably both stereocenters are in the configuration depicted.

Another embodiment is a compound of Formula Ij:

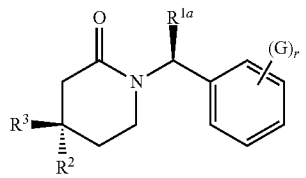

Ij wherein $R^2$ and $R^3$ are as defined for the first or second embodiments described for Formula I above, $R^{1a}$ is methyl or ethyl, r is 0, 1, 2, 3 or 4, and substituents G are independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkyl-aminocarbonyl, heterocyclylcarbonyl, ($C_1$-$C_6$)alkylaminosulfonyl, di($C_1$-$C_6$)alkylamino-sulfonyl, heterocyclosulfonyl, ($C_1$-$C_6$)

alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxy-carbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkylamino$(C_2-C_6)$alkoxy, $(C_1-C_6)$alkylamino$(C_2-C_6)$alkoxy, di$(C_1-C_6)$alkylamino$(C_2-C_6)$alkoxy and $(C_1-C_6)$alkylcarbonyl;
or a pharmaceutically acceptable salt, enantiomer or diastereomer thereof.

Alternatively for Formula Ij:
$R^2$ and $R^3$ are as defined for the first or second embodiments described for Formula I above, $R^{1a}$ is methyl or ethyl, r is 0, 1, 2, 3 or 4, and substituents G are independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkyl-carbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkylamino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, {$(C_3-C_6)$cycloalkyl}{$(C_1-C_6)$alkyl}aminocarbonyl, di$(C_3-C_6)$cycloalkylaminocarbonyl, $(C_3-C_6)$cycloalkylaminosulfonyl, {$(C_3-C_6)$cycloalkyl}{$(C_1-C_6)$alkyl}aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, {$(C_3-C_6)$cycloalkyl}{$(C_1-C_6)$alkyl}aminocarbonyl$(C_1-C_6)$alkyl and di$(C_3-C_6)$cycloalkylaminocarbonyl$(C_1-C_6)$alkyl; or
a pharmaceutically acceptable salt, enantiomer or diastereomer thereof.

Another embodiment is a compound of Formula Ik:

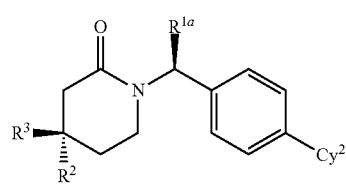

Ik wherein $Cy^2$, $R^2$ and $R^3$ are as defined for the first or second embodiments described for Formula I above, and $R^{1a}$ is methyl or ethyl;
or a pharmaceutically acceptable salt, enantiomer or diastereomer thereof.

Another embodiment is a compound of Formula Ik wherein $R^{1a}$ is methyl or ethyl, $R^2$ is phenyl optionally substituted with up to 2 groups selected from halogen, methyl, trifluoromethyl and cyano, $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl and $Cy^2$ is heterocyclyl optionally substituted with up to 3 groups independently selected from those described for $G^2$ in Formula If and oxo;
or a pharmaceutically acceptable salt, enantiomer or diastereomer thereof.

Another embodiment is a compound of Formula Ik wherein $R^{1a}$ is methyl or ethyl, $R^2$ is phenyl optionally substituted with up to 2 groups selected from halogen, methyl, trifluoromethyl and cyano, $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl and $Cy^2$ is 5-oxo-4,5-dihydro-1H-pyrazolyl, 3-oxo-2,3-dihydro-1H-pyrazolyl, 5-oxo-4,5-dihydro-1H-imidazolyl, 2-oxo-2,3-dihydro-1H-imidazolyl, 5-oxo-4,5-dihydro-1H-1,2,4-triazol-3-yl, 5-oxo-4,5-dihydro-1,3,4-thiadiazolyl, 1,2-dihydro-2-oxopyridyl, 2,3-dihydro-3-oxopyridazinyl, 1,2-dihydro-2-oxopyrimidinyl, 3,4-dihydro-4-oxopyrimidinyl or 1,2-dihydro-2-oxopyrazinyl optionally substituted with up to 3 groups independently selected from fluorine, chlorine, cyano, hydroxy, amino, $(C_1-C_4)$alkyl, $(C_3-C_4)$cycloalkyl, $(C_3-C_4)$cycloalkyl$(C_1-C_2)$alkyl, halo$(C_1-C_4)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl, and $(C_1-C_4)$alkylcarbonylamino; or a pharmaceutically acceptable salt, enantiomer or diastereomer thereof.

Another embodiment is a compound of Formula Ik wherein $R^{1a}$ is methyl or ethyl, $R^2$ is phenyl optionally substituted with up to 2 groups selected from halogen, methyl, trifluoromethyl and cyano, $R^3$ is 2-hydroxy-2-methylpropyl or 2-cyano-2-methylpropyl and $Cy^2$ is 1,2-dihydro-2-oxopyridyl, 2,3-dihydro-3-oxopyridazinyl, 1,2-dihydro-2-oxopyrimidinyl, 3,4-dihydro-4-oxopyrimidinyl or 1,2-dihydro-2-oxopyrazinyl optionally substituted with up to 2 groups independently selected from $(C_1-C_4)$alkyl, $(C_3-C_4)$cycloalkyl, halo$(C_1-C_4)$alkyl and halogen;
or a pharmaceutically acceptable salt, enantiomer or diastereomer thereof.

Another embodiment is a compound of Formula Ik wherein $R^{1a}$ is methyl or ethyl, $R^2$ is phenyl optionally substituted with up to 2 groups selected from halogen, methyl, trifluoromethyl and cyano, $R^3$ is 2-hydroxy-2-methylpropyl or 2-cyano-2-methylpropyl and $Cy^2$ is heteroaryl optionally substituted with up 2 groups selected from $(C_1-C_4)$alkyl, halo$(C_1-C_4)$alkyl, halogen, cyano, $CONH_2$, $(C_1-C_4)$alkylaminocarbonyl, di($C_1$-$C_4$)alkylaminocarbonyl and ($C_3$-$C_5$)cycloalkylaminocarbonyl or a pharmaceutically acceptable salt, enantiomer or diastereomer thereof. In another embodiment, $Cy^2$ is heteroaryl optionally substituted with one group selected from ($C_1$-$C_4$)alkyl, halo($C_1$-$C_4$)alkyl, halogen, cyano, CONHMe and CONMe$_2$; or a pharmaceutically acceptable salt, enantiomer or diastereomer thereof. In an alternative embodiment CONH$_2$ is excluded as a permissible substituent when $Cy^2$ is pyridine or thiazole. In yet another embodiment, $Cy^2$ is heteroaryl optionally substituted with one group selected from ($C_1$-$C_4$)alkyl, halo($C_1$-$C_4$)alkyl, halogen, cyano;

or a pharmaceutically acceptable salt, enantiomer or diastereomer thereof.

Another embodiment is a compound of Formula Ik wherein $R^{1a}$ is methyl or ethyl, $R^2$ is phenyl or fluorophenyl, $R^3$ is 2-hydroxy-2-methylpropyl or 2-cyano-2-methylpropyl and $Cy^2$ is pyridine, pyridine N-oxide, pyridazine, pyrimidine, pyrazine, thiazole, pyrazole or thiadiazole optionally substituted with methyl, fluorine, chlorine, cyano, CONH$_2$, CONHMe, CONMe$_2$, CONHt-Bu or CONHc—Pr;

or a pharmaceutically acceptable salt, enantiomer or diastereomer thereof. In an alternative embodiment CONH$_2$ is excluded as a permissible substituent when $Cy^2$ is pyridine or thiazole.

Another embodiment of the invention is a compound of any one of Formulas Il$^{1-3}$ or a pharmaceutically acceptable salt, enantiomer or diastereomer thereof:

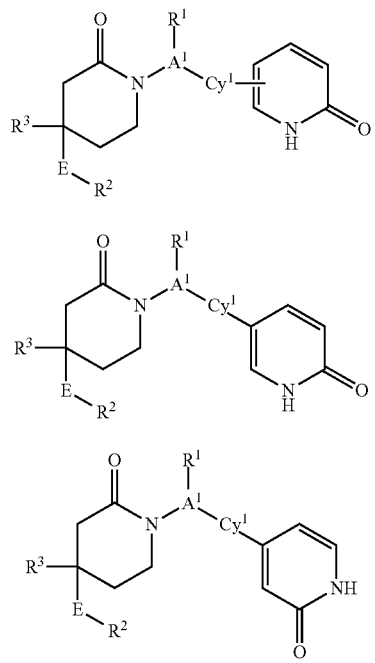

In Formulas Il$^{1-3}$, the oxodihydropyridyl ring in Formulas Il$^{1-3}$ are optionally substituted (substitution at ring carbons bonded to hydrogen and ring nitrogen atoms bonded to hydrogen atoms are encompassed, i.e., a "substitutable ring nitrogen atom") with up to four substituents as described above for $Cy^2$. Suitable substituents for $Cy^2$ and suitable values for $R^1$, $R^2$, $R^3$, $A^1$, $Cy^1$ and E are as defined in any one of the first, second, third or fourth embodiments. Alternatively, suitable substituents for $Cy^1$ and the oxodihydropyridyl ring in Formulas Il$^{1-3}$ are as described for $G^1$ and $G^2$, respectively, in Formula If, and values for $R^1$, $R^2$, $R^3$, $A^1$, $Cy^1$ and E are as defined in any one of the first, second, third or fourth embodiments. Alternatively, suitable substituents for $Cy^1$ include ($C_1$-$C_4$)alkyl, ($C_1$-$C_4$)alkoxy, ($C_1$-$C_4$)haloalkyl, ($C_1$-$C_4$)haloalkoxy, halogen, cyano and nitro; suitable substituents for a substitutable ring nitrogen atom in the oxodihydropyridyl ring in Formulas Il$^{1-3}$ include ($C_1$-$C_4$)alkyl, ($C_3$-$C_4$)cycloalkyl, ($C_3$-$C_4$)cycloalkyl($C_1$-$C_2$)alkyl, and ($C_1$-$C_4$)haloalkyl; suitable substituents for a ring carbon atom in the oxodihydropyridyl ring in Formulas Il$^{1-3}$ include fluorine, chlorine, cyano, hydroxy, amino, ($C_1$-$C_4$)alkyl, ($C_3$-$C_4$)cycloalkyl, ($C_3$-$C_4$)cycloalkyl($C_1$-$C_2$)alkyl, halo($C_1$-$C_4$)alkyl, ($C_1$-$C_4$)alkoxy, ($C_1$-$C_4$)haloalkoxy, CONH$_2$, ($C_1$-$C_4$)alkylaminocarbonyl, di($C_1$-$C_4$)alkylaminocarbonyl and ($C_1$-$C_4$)alkylcarbonylamino; and suitable values for $R^1$, $R^2$, $R^3$, $A^1$, $Cy^1$ and E are as defined in any one of the first, second, third or fourth embodiments.

For each of the embodiments described in the previous paragraph, $R^1$ is preferably methyl or ethyl.

For each of the embodiments described in the paragraph immediately following Formulas Il$^{1-3}$, $R^1$ is preferably methyl or ethyl; and $R^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas Il$^{1-3}$, $R^1$ is preferably methyl or ethyl; and $R^3$ is H$_2$NC(=O)CMe$_2$CH$_2$, 3-hydroxy-3-methylbutyl, 2-hydroxy-2-methylpropyl or 2-cyano-2-methylpropyl.

For each of the embodiments described in the paragraph immediately following Formulas Il$^{1-3}$, $R^1$ is preferably methyl or ethyl; $R^2$ is phenyl optionally substituted with 1, 2 or 3 substituents selected from halo, cyano, CONH$_2$, ($C_1$-$C_4$)alkyl, ($C_1$-$C_4$)haloalkyl, and SO$_2$Me; and $R^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas Il$^{1-3}$, $R^1$ is preferably methyl or ethyl; $R^2$ is phenyl optionally substituted with 1, 2 or 3 substituents selected from halo, cyano, CONH$_2$, ($C_1$-$C_4$)alkyl, ($C_1$-$C_4$)haloalkyl, and SO$_2$Me; and $R^3$ is H$_2$NC(=O)CMe$_2$CH$_2$, 3-hydroxy-3-methylbutyl, 2-hydroxy-2-methylpropyl or 2-cyano-2-methylpropyl.

For each of the embodiments described in the paragraph immediately following Formulas Il$^{1-3}$, $R^1$ is preferably methyl or ethyl; and $R^3$ is 2-hydroxy-2-methylpropyl or 2-cyano-2-methylpropyl.

For each of the embodiments described in the paragraph immediately following Formulas Il$^{1-3}$, $R^1$ is preferably methyl or ethyl; $R^2$ is phenyl or fluorophenyl; and $R^3$ is 2-hydroxy-2-methylpropyl or 2-cyano-2-methylpropyl.

For each of the embodiments described in the paragraph immediately following Formulas Il$^{1-3}$, $R^1$ is preferably methyl or ethyl; $R^2$ is phenyl or fluorophenyl; $R^3$ is 2-hydroxy-2-methylpropyl or 2-cyano-2-methylpropyl; the substituent on the substitutable ring nitrogen atom in the oxodihydropyridyl ring in Formulas Il$^{1-3}$ is ($C_1$-$C_4$)alkyl, ($C_3$-$C_4$)cycloalkyl, ($C_3$-$C_4$)cycloalkyl($C_1$-$C_2$)alkyl, or ($C_1$-$C_2$)haloalkyl; and one or two ring carbon atoms in the oxodihydropyridyl ring in Formulas Il$^{1-3}$ are optionally substituted with methyl or ethyl.

Another embodiment of the invention is a compound of any one of Formulas Im$^{1-3}$, or a pharmaceutically acceptable salt, enantiomer or diastereomer thereof:

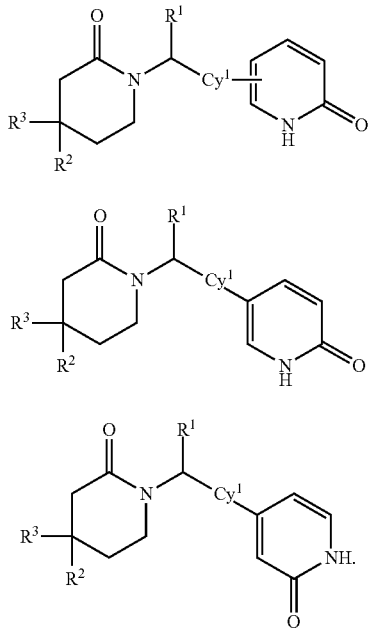

In Formulas Im$^{1-3}$, the oxodihydropyridyl ring are optionally substituted (substitution at ring carbons bonded to hydrogen and at nitrogen atoms bonded to hydrogen atoms are encompassed, i.e., a "substitutable ring nitrogen atom") with up to four substituents as described above for Cy$^2$. Suitable substituents for Cy$^2$ and suitable values for R$^1$, R$^2$, R$^3$ and Cy$^1$ are as defined in any one of the first, second, third or fourth embodiments. Alternatively, suitable substituents for Cy$^1$ and the oxodihydropyridyl ring in Formulas Im$^{1-3}$ are as described for G$^1$ and G$^2$, respectively, in Formula If, and values for R$^1$, R$^2$, R$^3$ and Cy$^1$ are as defined in any one of the first, second, third or fourth embodiments. Alternatively, suitable substituents for Cy$^1$ include (C$_1$-C$_4$)alkyl, (C$_1$-C$_4$) alkoxy, (C$_1$-C$_4$)haloalkyl, (C$_1$-C$_4$)haloalkoxy, halogen, cyano and nitro; suitable substituents for a substitutable ring nitrogen atom in the oxodihydropyridyl ring in Formulas Im$^{1-3}$ include (C$_1$-C$_4$)alkyl, (C$_3$-C$_4$)cycloalkyl, (C$_3$-C$_4$)cycloalkyl(C$_1$-C$_2$)alkyl and (C$_1$-C$_4$)haloalkyl; suitable substituents for a ring carbon atom in the oxodihydropyridyl ring in Formulas Im$^{1-3}$ include fluorine, chlorine, cyano, hydroxy, amino, (C$_1$-C$_4$)alkyl, (C$_3$-C$_4$)cycloalkyl, (C$_3$-C$_4$)cycloalkyl (C$_1$-C$_2$)alkyl, halo(C$_1$-C$_4$)alkyl, (C$_1$-C$_4$)alkoxy, (C$_1$-C$_4$)haloalkoxy, CONH$_2$, (C$_1$-C$_4$)alkylaminocarbonyl, di(C$_1$-C$_4$) alkylaminocarbonyl and (C$_1$-C$_4$)alkylcarbonylamino; and suitable values for R$^1$, R$^2$, R$^3$ and Cy$^1$ are as defined in any one of the first, second, third or fourth embodiments.

For each of the embodiments described in the previous paragraph, R$^1$ is preferably methyl or ethyl.

For each of the embodiments described in the paragraph immediately following Formulas Im$^{1-3}$, R$^1$ is preferably methyl or ethyl; and R$^3$ is MeSO$_2$NHCH$_2$CH$_2$CH$_2$, H$_2$NC (=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas Im$^{1-3}$, R$^1$ is preferably methyl or ethyl; and R$^3$ is H$_2$NC(=O)CMe$_2$CH$_2$, 3-hydroxy-3-methylbutyl, 2-hydroxy-2-methylpropyl or 2-cyano-2-methylpropyl.

For each of the embodiments described in the paragraph immediately following Formulas Im$^{1-3}$, R$^1$ is preferably methyl or ethyl; R$^2$ is phenyl optionally substituted with 1, 2 or 3 substituents selected from halo, cyano, CONH$_2$, (C$_1$-C$_4$) alkyl, (C$_1$-C$_4$)haloalkyl and SO$_2$Me; and R$^3$ is MeSO$_2$NHCH$_2$CH$_2$CH$_2$, H$_2$NC(=O)CH$_2$CH$_2$, H$_2$NC(=O) CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas Im$^{1-3}$, R$^1$ is preferably methyl or ethyl; R$^2$ is phenyl optionally substituted with 1, 2 or 3 substituents selected from halo, cyano, CONH$_2$, (C$_1$-C$_4$) alkyl, (C$_1$-C$_4$)haloalkyl and SO$_2$Me; and R$^3$ is H$_2$NC(=O) CMe$_2$CH$_2$, 3-hydroxy-3-methylbutyl, 2-hydroxy-2-methylpropyl or 2-cyano-2-methylpropyl.

For each of the embodiments described in the paragraph immediately following Formulas Im$^{1-3}$, R$^1$ is preferably methyl or ethyl; and R$^3$ is 2-hydroxy-2-methylpropyl or 2-cyano-2-methylpropyl.

For each of the embodiments described in the paragraph immediately following Formulas Im$^{1-3}$, R$^1$ is preferably methyl or ethyl; R$^2$ is phenyl or fluorophenyl; and R$^3$ is 2-hydroxy-2-methylpropyl or 2-cyano-2-methylpropyl.

For each of the embodiments described in the paragraph immediately following Formulas Im$^{1-3}$, R$^1$ is preferably methyl or ethyl; R$^2$ is phenyl or fluorophenyl; R$^3$ is 2-hydroxy-2-methylpropyl or 2-cyano-2-methylpropyl; the substituent on the substitutable ring nitrogen atom in the oxodihydropyridyl ring in Formulas Im$^{1-3}$ is (C$_1$-C$_4$)alkyl, (C$_3$-C$_4$) cycloalkyl, (C$_3$-C$_4$)cycloalkyl(C$_1$-C$_2$)alkyl, or (C$_1$-C$_2$) haloalkyl; and one or two ring carbon atoms in the oxodihydropyridyl ring in Formulas Im$^{1-3}$ are optionally substituted with methyl or ethyl.

Another embodiment of the invention is a compound of any one for Formulas In$^{1-3}$, or a pharmaceutically acceptable salt thereof:

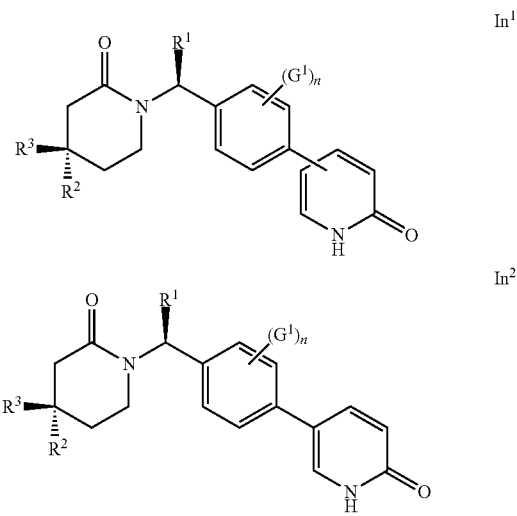

-continued

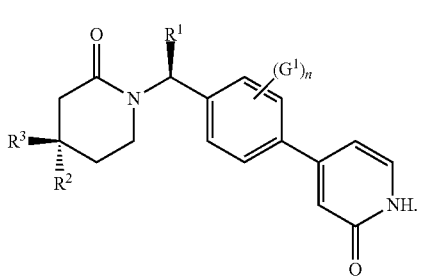

In³

In Formulas In¹⁻³, the oxodihydropyridyl ring in Formulas In¹⁻³ are optionally substituted (substitution at ring carbons bonded to hydrogen and at nitrogen atoms bonded to hydrogen atoms are encompassed, i.e., a "substitutable ring nitrogen atom") with up to four substituents as described above for $Cy^2$; suitable values for $G^1$ are as described for $G^1$ in Formula If; n is 0, 1, 2 or 3; and suitable substituents for $Cy^2$ and suitable values for $R^1$, $R^2$ and $R^3$ are as defined in any one of the first, second, third or fourth embodiments. Alternatively, n is 0, 1, 2 or 3; suitable values for $G^1$ and substituents for the oxodihydropyridyl ring in Formulas In¹⁻³ are as described for $G^1$ and $G^2$, respectively, in Formula If, and values for $R^1$, $R^2$ and $R^3$ are as defined in any one of the first, second, third or fourth embodiments. Alternatively, n is 0, 1, 2 or 3; suitable values for $G^1$ include $(C_1-C_4)$alkyl, $(C_1-C_4)$alkoxy, $(C_1-C_4)$haloalkyl, $(C_1-C_4)$haloalkoxy, halogen, cyano and nitro; suitable substituents for a substitutable ring nitrogen atom in the oxodihydropyridyl ring in Formulas In¹⁻³ include $C_1-C_4$ alkyl, $(C_3-C_4)$cycloalkyl, $(C_3-C_4)$cycloalkyl$(C_1-C_2)$alkyl and $C_1-C_4$ haloalkyl; and suitable values for $R^1$, $R^2$ and $R^3$ are as defined in any one of the first, second, third or fourth embodiments.

For each of the embodiments described in the previous paragraph, $R^1$ is preferably methyl or ethyl.

For each of the embodiments described in the paragraph immediately following Formulas In¹⁻³, $R^1$ is preferably methyl or ethyl; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas In¹⁻³, $R^1$ is preferably methyl or ethyl; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiments described in the paragraph immediately following Formulas In¹⁻³, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas In¹⁻³, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiments described in the paragraph immediately following Formulas In¹⁻³, $R^1$ is preferably methyl or ethyl; and $R^3$ is 2-hydroxy-2-methylpropyl or 2-cyano-2-methylpropyl.

For each of the embodiments described in the paragraph immediately following Formulas In¹⁻³, $R^1$ is preferably methyl or ethyl; $R^2$ is phenyl or fluorophenyl; and $R^3$ is 2-hydroxy-2-methylpropyl or 2-cyano-2-methylpropyl.

For each of the embodiments described in the paragraph immediately following Formulas In¹⁻³, $R^1$ is preferably methyl or ethyl; $R^2$ is phenyl or fluorophenyl; $R^3$ is 2-hydroxy-2-methylpropyl or 2-cyano-2-methylpropyl; the substituent on the substitutable ring nitrogen atom in the oxodihydropyridyl ring in Formulas In¹⁻³ is $(C_1-C_4)$alkyl, $(C_3-C_4)$cycloalkyl, $(C_3-C_4)$cycloalkyl$(C_1-C_2)$alkyl, or $(C_1-C_2)$haloalkyl; and one or two ring carbon atoms in the oxodihydropyridyl ring in Formulas In¹⁻³ are optionally substituted with methyl or ethyl.

Another embodiment of the invention is a compound represented by any one of Formulas Io¹⁻² or a pharmaceutically acceptable salt thereof:

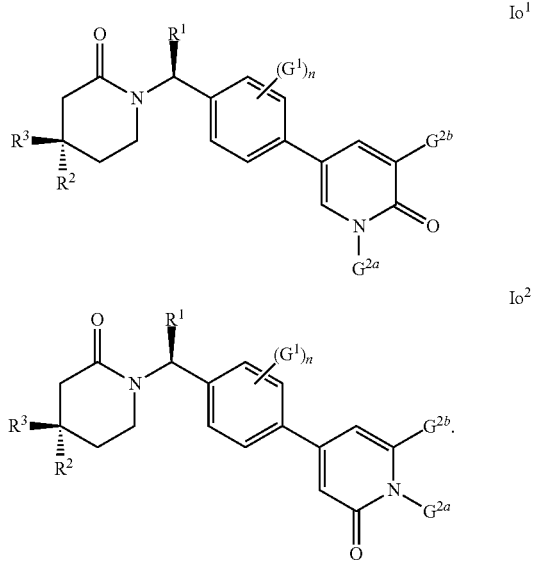

In Formulas Io¹⁻², $G^1$ is $(C_1-C_4)$alkyl, $(C_1-C_4)$alkoxy, $(C_1-C_4)$haloalkyl, $(C_1-C_4)$haloalkoxy, halogen, cyano or nitro; n is 0, 1 or 2; $G^{2a}$ is $(C_1-C_4)$alkyl, $(C_3-C_4)$cycloalkyl or $(C_1-C_4)$haloalkyl; $G^{2b}$ is hydrogen, fluorine, chlorine, cyano, hydroxy, amino, $(C_1-C_4)$alkyl, $(C_3-C_4)$cycloalkyl, $(C_3-C_4)$cycloalkyl$(C_1-C_2)$alkyl, halo$(C_1-C_4)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl or $(C_1-C_4)$alkylcarbonylamino; and suitable values for $R^1$, $R^2$ and $R^3$ are as defined in any one of the first, second, third or fourth embodiments.

For each of the embodiments described in the previous paragraph, $R^1$ is preferably methyl or ethyl.

For each of the embodiments described in the paragraph immediately following Formulas Io¹⁻², $R^1$ is preferably methyl or ethyl; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas Io¹⁻², $R^1$ is preferably methyl or ethyl; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiments described in the paragraph immediately following Formulas Io¹⁻², $R^1$ is preferably methyl or ethyl; $R^2$ is phenyl optionally substituted with 1, 2 or 3 substituents selected from halo, cyano, $CONH_2$, $(C_1-C_4)$ alkyl, $(C_1-C_4)$haloalkyl and $SO_2Me$; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas $Io^{1-2}$, $R^1$ is preferably methyl or ethyl; $R^2$ is phenyl optionally substituted with 1, 2 or 3 substituents selected from halo, cyano, $CONH_2$, $(C_1-C_4)$ alkyl, $(C_1-C_4)$haloalkyl and $SO_2Me$; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiments described in the paragraph immediately following Formulas $Io^{1-2}$, $R^1$ is preferably methyl or ethyl; and $R^3$ is 2-hydroxy-2-methylpropyl or 2-cyano-2-methylpropyl.

For each of the embodiments described in the paragraph immediately following Formulas $Io^{1-2}$, $R^1$ is preferably methyl or ethyl; $R^2$ is phenyl or fluorophenyl; and $R^3$ is 2-hydroxy-2-methylpropyl or 2-cyano-2-methylpropyl.

For each of the embodiment described in the paragraph immediately following Formulas $Io^{1-2}$, $R^1$ is preferably methyl or ethyl; $R^2$ is phenyl or fluorophenyl; $R^3$ is 2-hydroxy-2-methylpropyl or 2-cyano-2-methylpropyl; the substituent $G^{2a}$ is selected from $(C_1-C_4)$alkyl, $(C_3-C_4)$cycloalkyl, $(C_3-C_4)$cycloalkyl$(C_1-C_2)$alkyl, and $(C_1-C_2)$haloalkyl; and $G^{2b}$ is optionally selected from hydrogen, methyl or ethyl.

Another embodiment of the invention is a compound of any one of Formulas $Ip^{1-6}$ or a pharmaceutically acceptable salt, enantiomer or diastereomer thereof:

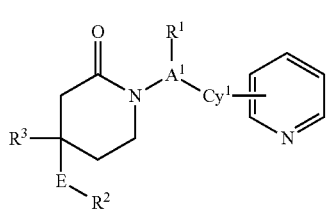

$Ip^1$

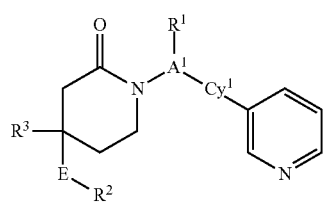

$Ip^2$

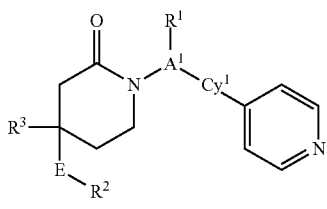

$Ip^3$

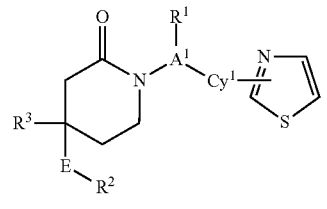

$Ip^4$

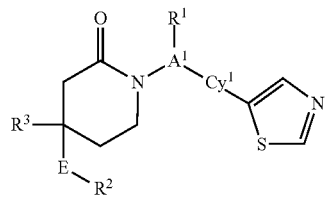

$Ip^5$

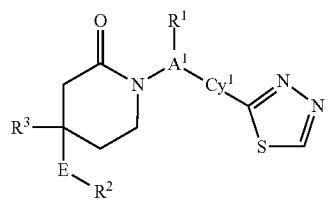

$Ip^6$

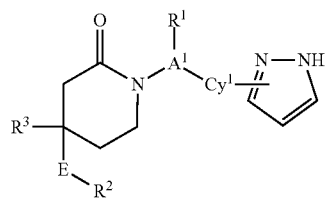

$Ip^7$

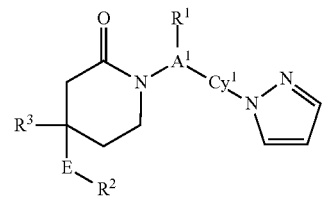

$Ip^8$

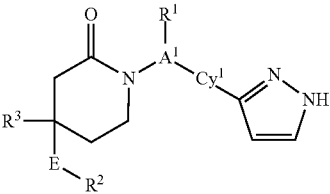

$Ip^9$

In Formulas $Ip^{1-9}$, the pyridine, pyrazole, thiazole and thiadiazole rings in Formulas $Ip^{1-9}$ are optionally substituted (substitution at ring carbons bonded to hydrogen and ring nitrogen atoms bonded to hydrogen atoms are encompassed, i.e., a "substitutable ring nitrogen atom") with up to four substituents as described above for $Cy^2$. Alternatively, —CHO, $NH_2$—$SO_2NH_2$, —COOH, and —$CONH_2$ are excluded as permissible substituents for the pyridine, pyrazole, thiazole and thiadiazole rings at the position corresponding to $Cy^2$ for all of the specific embodiments described above for Formulas $Ip^{1-9}$. Suitable substituents for $Cy^2$ and suitable values for $R^1$, $R^2$, $R^3$, $A^1$, $Cy^1$ and E are as defined in any one of the first, second, third or fourth embodiments. Alternatively, suitable substituents for $Cy^1$ and the pyridine, pyrazole, thiazole and thiadiazole rings in Formulas $Ip^{1-9}$ are as described for $G^1$ and $G^2$, respectively, in Formula If, and values for $R^1$, $R^2$, $R^3$, $A^1$, $Cy^1$ and E are as defined in any one of the first, second, third or fourth embodiments. Alternatively, suitable substituents for $Cy^1$ include $(C_1-C_4)$alkyl, $(C_1-C_4)$alkoxy, $(C_1-C_4)$haloalkyl, $(C_1-C_4)$haloalkoxy, halogen, cyano and nitro; suitable substituents for a ring carbon atom in the pyridine, pyrazole, thiazole and thiadiazole rings in Formulas $Ip^{1-9}$ include fluorine, chlorine, cyano, amino, $(C_1-C_4)$alkyl, $(C_3-C_4)$cycloalkyl, $(C_3-C_4)$cycloalkyl$(C_1-C_2)$alkyl, halo$(C_1-C_4)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl, $(C_3-C_4)$cycloalkylaminocarbonyl, $\{(C_1-C_4)$alkyl$\}\{(C_3-C_4)$cycloalkyl$\}$aminocarbonyl and $(C_1-C_4)$alkylcarbonylamino; the ring nitrogen in the pyridine rings in Formulas $Ip^{1-3}$ is optionally substituted by oxo; and suitable values for $R^1$, $R^2$, $R^3$, $A^1$, $Cy^1$ and E are as defined in any one of the first, second, third or fourth embodiments.

For each of the embodiments described in the previous paragraph, $R^1$ is preferably methyl or ethyl.

For each of the embodiments described in the paragraph immediately following Formulas $Ip^{1-9}$, $R^1$ is preferably methyl or ethyl; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas $Ip^{1-9}$, $R^1$ is preferably methyl or ethyl; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiments described in the paragraph immediately following Formulas $Ip^{1-9}$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas $Ip^{1-9}$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiments described in the paragraph immediately following Formulas $Ip^{1-9}$, $R^1$ is preferably methyl or ethyl; and $R^3$ is 2-hydroxy-2-methylpropyl or 2-cyano-2-methylpropyl.

For each of the embodiments described in the paragraph immediately following Formulas $Ip^{1-9}$, $R^1$ is preferably methyl or ethyl; $R^2$ is phenyl or fluorophenyl; and $R^3$ is 2-hydroxy-2-methylpropyl or 2-cyano-2-methylpropyl.

For each of the embodiments described in the paragraph immediately following Formulas $Ip^{1-9}$, $R^1$ is preferably methyl or ethyl; $R^2$ is phenyl or fluorophenyl; $R^3$ is 2-hydroxy-2-methylpropyl or 2-cyano-2-methylpropyl; one or two ring carbon atoms in the pyridine, pyrazole, thiazole and thiadiazole rings in Formulas $Ip^{1-9}$ are optionally substituted with fluoro, chloro, cyano, $CONH_2$, $CONHMe$, $CONMe_2$, $CONHc$—$Pr$, methoxy, ethoxy, methyl, ethyl or $CF_3$; the ring nitrogen in the pyridine rings in Formulas $Ip^{1-3}$ is optionally substituted by oxo.

Another embodiment of the invention is a compound of any one of Formulas $Iq^{1-9}$, or a pharmaceutically acceptable salt, enantiomer or diastereomer thereof:

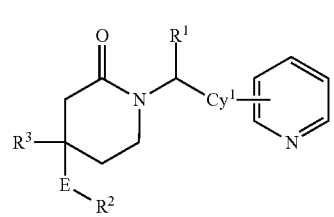

Iq¹

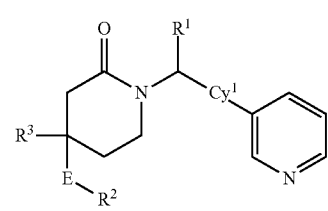

Iq²

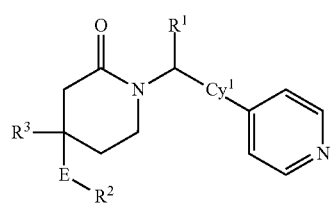

Iq³

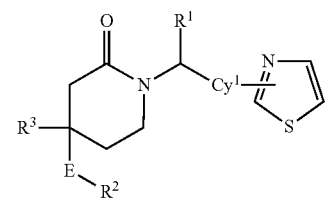

Iq⁴

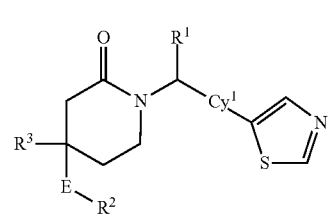

Iq⁵

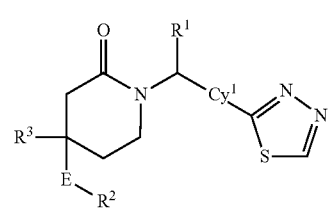

Iq⁶

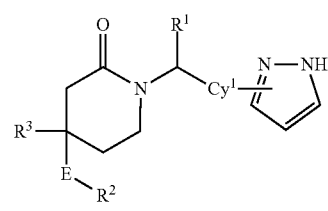

Iq⁷

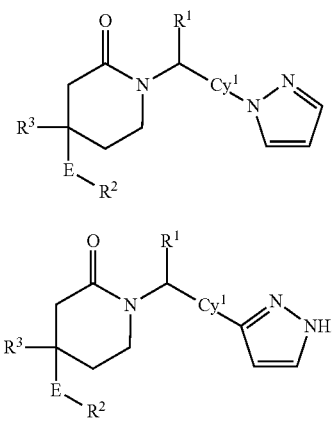

In Formulas Iq$^{1-6}$, the pyridine, pyrazole, thiazole and thiadiazole rings in Formulas Iq$^{1-9}$ are optionally substituted (substitution at ring carbons bonded to hydrogen and ring nitrogen atoms bonded to hydrogen atoms are encompassed, i.e., a "substitutable ring nitrogen atom") with up to four substituents as described above for Cy$^2$. Suitable substituents for Cy$^2$ and suitable values for R$^1$, R$^2$, R$^3$, Cy$^1$ and E are as defined in any one of the first, second, third or fourth embodiments. Alternatively, —CHO, NH$_2$—SO$_2$NH$_2$, —COOH, and —CONH$_2$ are excluded as permissible substituents for the pyridine, pyrazole, thiazole and thiadiazole rings at the position corresponding to Cy$^2$ for all of the specific embodiments described above for Formulas Iq$^{1-9}$. Alternatively, suitable substituents for Cy$^1$ and the pyridine, pyrazole, thiazole and thiadiazole rings in Formulas Iq$^{1-9}$ are as described for G$^1$ and G$^2$, respectively, in Formula If, and values for R$^1$, R$^2$, R$^3$, Cy$^1$ and E are as defined in any one of the first, second, third or fourth embodiments. Alternatively, suitable substituents for Cy$^1$ include (C$_1$-C$_4$)alkyl, (C$_1$-C$_4$)alkoxy, (C$_1$-C$_4$)haloalkyl, (C$_1$-C$_4$)haloalkoxy, halogen, cyano and nitro; suitable substituents for a ring carbon atom in the pyridine, pyrazole, thiazole and thiadiazole rings in Formulas Iq$^{1-9}$ include fluorine, chlorine, cyano, hydroxy, amino, (C$_1$-C$_4$)alkyl, (C$_3$-C$_4$)cycloalkyl, (C$_3$-C$_4$)cycloalkyl(C$_1$-C$_2$)alkyl, halo(C$_1$-C$_4$)alkyl, (C$_1$-C$_4$)alkoxy, (C$_1$-C$_4$)haloalkoxy, CONH$_2$, (C$_1$-C$_4$)alkylaminocarbonyl, di(C$_1$-C$_4$)alkylaminocarbonyl, (C$_3$-C$_4$)cycloalkylaminocarbonyl, {(C$_1$-C$_4$)alkyl}{(C$_3$-C$_4$)cycloalkyl}aminocarbonyl and (C$_1$-C$_4$)alkylcarbonylamino; the ring nitrogen in pyridines Iq$^{1-3}$ is optionally substituted by oxo; and suitable values for R$^1$, R$^2$, R$^3$, Cy$^1$ and E are as defined in any one of the first, second, third or fourth embodiments.

For each of the embodiment described in the previous paragraph, R$^1$ is preferably methyl or ethyl.

For each of the embodiment described in the paragraph immediately following Formulas Iq$^{1-9}$, R$^1$ is preferably methyl or ethyl; and R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiment described in the paragraph immediately following Formulas Iq$^{1-9}$, R$^1$ is preferably methyl or ethyl; and R$^3$ is H$_2$NC(=O)CMe$_2$CH$_2$, 3-hydroxy-3-methylbutyl, 2-hydroxy-2-methylpropyl or 2-cyano-2-methylpropyl.

For each of the embodiment described in the paragraph immediately following Formulas Iq$^{1-9}$, R$^1$ is preferably methyl or ethyl; R$^2$ is phenyl optionally substituted with 1, 2 or 3 substituents selected from halo, cyano, CONH$_2$, (C$_1$-C$_4$) alkyl, (C$_1$-C$_4$)haloalkyl and SO$_2$Me; and R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiment described in the paragraph immediately following Formulas Iq$^{1-9}$, R$^1$ is preferably methyl or ethyl; R$^2$ is phenyl optionally substituted with 1, 2 or 3 substituents selected from halo, cyano, CONH$_2$, (C$_1$-C$_4$) alkyl, (C$_1$-C$_4$)haloalkyl and SO$_2$Me; and R$^3$ is H$_2$NC(=O)CMe$_2$CH$_2$, 3-hydroxy-3-methylbutyl, 2-hydroxy-2-methylpropyl or 2-cyano-2-methylpropyl.

For each of the embodiment described in the paragraph immediately following Formulas Iq$^{1-9}$, R$^1$ is preferably methyl or ethyl; and R$^3$ is 2-hydroxy-2-methylpropyl or 2-cyano-2-methylpropyl.

For each of the embodiment described in the paragraph immediately following Formulas Iq$^{1-9}$, R$^1$ is preferably methyl or ethyl; R$^2$ is phenyl or fluorophenyl; and R$^3$ is 2-hydroxy-2-methylpropyl or 2-cyano-2-methylpropyl.

For each of the embodiment described in the paragraph immediately following Formulas Iq$^{1-9}$, R$^1$ is preferably methyl or ethyl; R$^2$ is phenyl or fluorophenyl; R$^3$ is 2-hydroxy-2-methylpropyl or 2-cyano-2-methylpropyl; one or two ring carbon atoms in the pyrazole, thiazole and thiadiazole rings in Formulas Iq$^{1-9}$ are optionally substituted with fluoro, chloro, cyano, CONH$_2$, CONHMe, CONMe$_2$, CONHc—Pr, methoxy, ethoxy, methyl, ethyl or CF$_3$, the ring nitrogen in the pyridine rings in Formulas Iq$^{1-3}$ is optionally substituted by oxo.

Another embodiment of the invention is a compound of any one of Formulas Ir$^{1-9}$, or a pharmaceutically acceptable salt, enantiomer or diastereomer thereof:

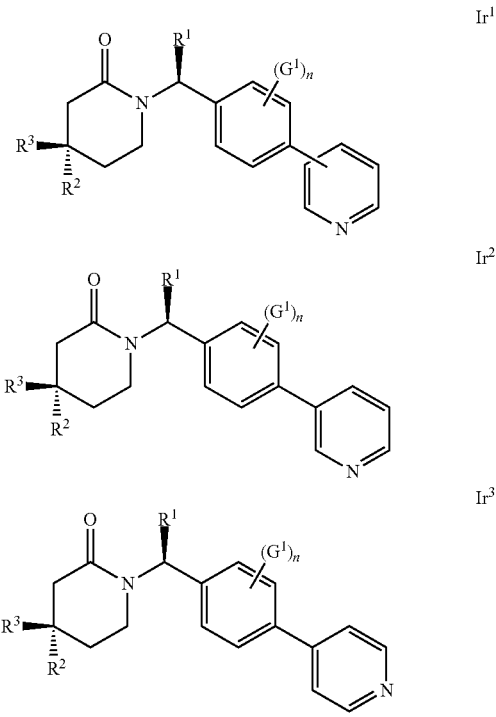

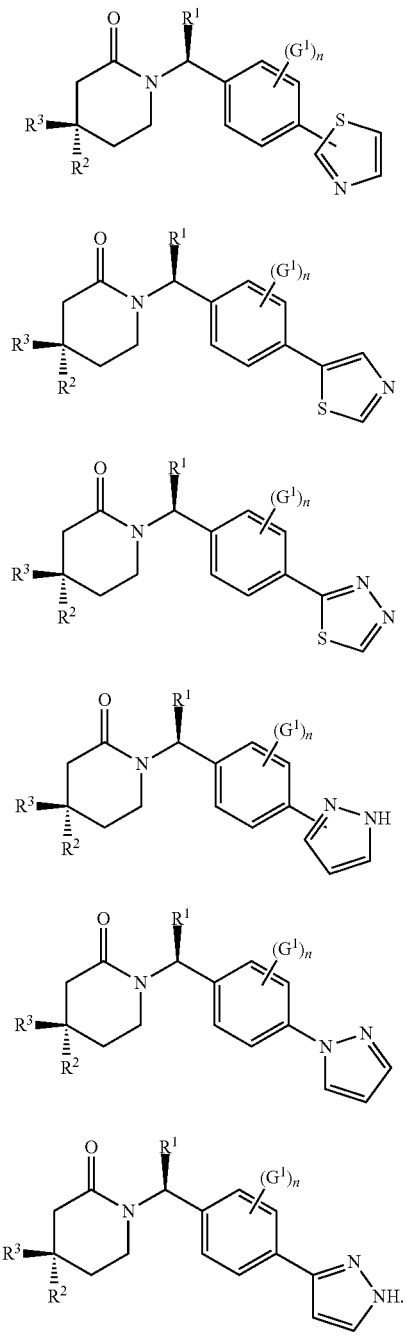

In Formulas Ir$^{1-9}$, the pyridine, pyrazole, thiazole and thiadiazole rings in Formulas Ir$^{1-9}$ are optionally substituted (substitution at ring carbons bonded to hydrogen and ring nitrogen atoms bonded to hydrogen atoms are encompassed, i.e., a "substitutable ring nitrogen atom") with up to four substituents as described above for Cy$^2$. Alternatively, —CHO, NH$_2$—SO$_2$NH$_2$, —COOH, and —CONH$_2$ are excluded as permissible substituents for the pyridine, pyrazole, thiazole and thiadiazole rings at the position corresponding to Cy$^2$ for all of the specific embodiments described above for Formulas Ir$^{1-9}$.

Suitable values for G$^1$ are as described in Formula If; n is 0, 1 or 2; substituents for Cy$^2$ and suitable values for R$^1$, R$^2$ and R$^3$ are as defined in any one of the first, second, third or fourth embodiments. Alternatively, n is 0, 1 or 2, suitable values for G$^1$ in Formulas Ir$^{1-9}$ and suitable substituents for the pyridine, pyrazole, thiazole and thiadiazole rings in Formulas Ir$^{1-9}$ are as described for G$^1$ and G$^2$, respectively, in Formula If, and values for R$^1$, R$^2$ and R$^3$ are as defined in any one of the first, second, third or fourth embodiments. Alternatively, n is 0, 1 or 2; suitable values for G$^1$ include (C$_1$-C$_4$)alkyl, (C$_1$-C$_4$)alkoxy, (C$_1$-C$_4$)haloalkyl, (C$_1$-C$_4$)haloalkoxy, halogen, cyano and nitro; suitable substituents for a ring carbon atom in the pyridine, pyrazole, thiazole and thiadiazole rings in Formulas Ir$^{1-9}$ include fluorine, chlorine, cyano, amino, (C$_1$-C$_4$)alkyl, (C$_3$-C$_4$)cycloalkyl, (C$_3$-C$_4$)cycloalkyl(C$_1$-C$_2$)alkyl, halo(C$_1$-C$_4$)alkyl, (C$_1$-C$_4$)alkoxy, (C$_1$-C$_4$)haloalkoxy, CONH$_2$, (C$_1$-C$_4$)alkylaminocarbonyl, di(C$_1$-C$_4$)alkylaminocarbonyl, (C$_3$-C$_4$)cycloalkylaminocarbonyl, {(C$_1$-C$_4$)alkyl}{(C$_3$-C$_4$)cycloalkyl}aminocarbonyl and (C$_1$-C$_4$)alkylcarbonylamino; the ring nitrogen in pyridines Ir$^{1-3}$ is optionally substituted by oxo; and suitable values for R$^1$, R$^2$ and R$^3$ are as defined in any one of the first, second, third or fourth embodiments.

For each of the embodiment described in the previous paragraph, R$^1$ is preferably methyl or ethyl.

For each of the embodiment described in the paragraph immediately following Formulas Ir$^{1-9}$, R$^1$ is preferably methyl or ethyl; and R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiment described in the paragraph immediately following Formulas Ir$^{1-9}$, R$^1$ is preferably methyl or ethyl; and R$^3$ is H$_2$NC(=O)CMe$_2$CH$_2$, 3-hydroxy-3-methylbutyl, 2-hydroxy-2-methylpropyl or 2-cyano-2-methylpropyl.

For each of the embodiment described in the paragraph immediately following Formulas Ir$^{1-9}$, R$^1$ is preferably methyl or ethyl; R$^2$ is phenyl optionally substituted with 1, 2 or 3 substituents selected from halo, cyano, CONH$_2$, (C$_1$-C$_4$)alkyl, (C$_1$-C$_4$)haloalkyl and SO$_2$Me; and R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiment described in the paragraph immediately following Formulas Ir$^{1-9}$, R$^1$ is preferably methyl or ethyl; R$^2$ is phenyl optionally substituted with 1, 2 or 3 substituents selected from halo, cyano, CONH$_2$, (C$_1$-C$_4$)alkyl, (C$_1$-C$_4$)haloalkyl and SO$_2$Me; and R$^3$ is H$_2$NC(=O)CMe$_2$CH$_2$, 3-hydroxy-3-methylbutyl, 2-hydroxy-2-methylpropyl or 2-cyano-2-methylpropyl.

For each of the embodiment described in the paragraph immediately following Formulas Ir$^{1-9}$, R$^1$ is preferably methyl or ethyl; and R$^3$ is 2-hydroxy-2-methylpropyl or 2-cyano-2-methylpropyl.

For each of the embodiment described in the paragraph immediately following Formulas Ir$^{1-9}$, R$^1$ is preferably methyl or ethyl; R$^2$ is phenyl or fluorophenyl; and R$^3$ is 2-hydroxy-2-methylpropyl or 2-cyano-2-methylpropyl.

For each of the embodiment described in the paragraph immediately following Formulas Ir$^{1-9}$, R$^1$ is preferably methyl or ethyl; R$^2$ is phenyl or fluorophenyl; R$^3$ is 2-hydroxy-2-methylpropyl or 2-cyano-2-methylpropyl; one or two ring carbon atoms in the pyridine, pyrazole, thiazole and thiadiazole rings in Formulas Ir$^{1-9}$ are optionally substituted with fluoro, chloro, cyano, CONH$_2$, CONHMe, CONMe$_2$, CONHc—Pr, methyl, ethyl or CF$_3$; the ring nitrogen in the pyridine rings in Formulas Ir$^{1-3}$ is optionally substituted by oxo.

Another embodiment of the invention is a compound represented by any one of Formulas Is$^{1-3}$, or a pharmaceutically acceptable salt thereof:

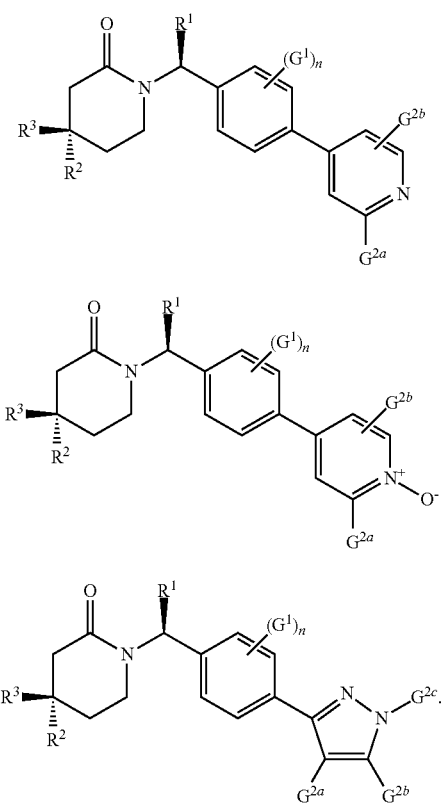

In Formulas Is$^{1-3}$, G$^1$ is (C$_1$-C$_4$)alkyl, (C$_1$-C$_4$)alkoxy, (C$_1$-C$_4$)haloalkyl, (C$_1$-C$_4$)haloalkoxy, halogen, cyano and nitro; n is 0 1 or 2; G$^{2a}$ and G$^{2b}$ are independently selected from hydrogen, fluorine, chlorine, cyano, amino, (C$_1$-C$_4$)alkyl, (C$_3$-C$_4$)cycloalkyl, (C$_3$-C$_4$)cycloalkyl(C$_1$-C$_2$)alkyl, halo(C$_1$-C$_4$)alkyl, (C$_1$-C$_4$)alkoxy, (C$_1$-C$_4$)haloalkoxy, CONH$_2$, (C$_1$-C$_4$)alkylaminocarbonyl, di(C$_1$-C$_4$)alkylaminocarbonyl, (C$_3$-C$_4$)cycloalkylaminocarbonyl, {(C$_1$-C$_4$)alkyl}{(C$_3$-C$_4$)cycloalkyl}aminocarbonyl and (C$_1$-C$_4$)alkylcarbonylamino; G$^{2c}$ is (C$_1$-C$_4$)alkyl, (C$_3$-C$_4$)cycloalkyl or (C$_1$-C$_4$)haloalkyl; and suitable values for R$^1$, R$^2$ and R$^3$ are as defined in any one of the first, second, third or fourth embodiments.

For each of the embodiment described in the previous paragraph, R$^1$ is preferably methyl or ethyl.

For each of the embodiment described in the paragraph immediately following Formulas Is$^{1-3}$, R$^1$ is preferably methyl or ethyl; and R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiment described in the paragraph immediately following Formulas Is$^{1-3}$, R$^1$ is preferably methyl or ethyl; and R$^3$ is H$_2$NC(=O)CMe$_2$CH$_2$, 3-hydroxy-3-methylbutyl, 2-hydroxy-2-methylpropyl or 2-cyano-2-methylpropyl.

For each of the embodiment described in the paragraph immediately following Formulas Is$^{1-3}$, R$^1$ is preferably methyl or ethyl; R$^2$ is phenyl optionally substituted with 1, 2 or 3 substituents selected from halo, cyano, CONH$_2$, (C$_1$-C$_4$) alkyl, (C$_1$-C$_4$)haloalkyl and SO$_2$Me; and R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiment described in the paragraph immediately following Formulas Is$^{1-3}$, R$^1$ is preferably methyl or ethyl; R$^2$ is phenyl optionally substituted with 1, 2 or 3 substituents selected from halo, cyano, CONH$_2$, (C$_1$-C$_4$) alkyl, (C$_1$-C$_4$)haloalkyl and SO$_2$Me; and R$^3$ is H$_2$NC(=O)CMe$_2$CH$_2$, 3-hydroxy-3-methylbutyl, 2-hydroxyethyl, 2-hydroxy-2-methylpropyl or 2-cyano-2-methylpropyl.

For each of the embodiment described in the paragraph immediately following Formulas Is$^{1-3}$, R$^1$ is preferably methyl or ethyl; and R$^3$ is 2-hydroxy-2-methylpropyl or 2-cyano-2-methylpropyl.

For each of the embodiment described in the paragraph immediately following Formulas Is$^{1-3}$, R$^1$ is preferably methyl or ethyl; R$^2$ is phenyl or fluorophenyl; and R$^3$ is 2-hydroxy-2-methylpropyl or 2-cyano-2-methylpropyl.

Alternatively, —CHO, NH$_2$—SO$_2$NH$_2$, —COOH, and —CONH$_2$ are excluded as permissible substituents for the pyridine, pyrazole, thiazole and thiadiazole rings at the position corresponding to Cy$^2$ for all of the specific embodiments described above for Formulas Ip$^{1-9}$, Iq$^{1-9}$, Ir$^{1-9}$, and Is$^{1-3}$.

The present invention further provides methods of inhibiting 11β-HSD1 by contacting 11β-HSD1 with a compound of Formula I, I*, Ia, Ib, Ic, Id, Ie, If, If*, Ig, Ih, Ij, Ik, Il$^{1-3}$, Im$^{1-3}$, In$^{1-3}$, Io$^{1-2}$, Ip$^{1-9}$, Iq$^{1-9}$, Ir$^{1-9}$ or Is$^{1-3}$ of the invention.

The present invention further provides methods of inhibiting or reducing the conversion of cortisone to cortisol in a cell using a compound of Formula I, I*, Ia, Ib, Ic, Id, Ie, If, If*, Ig, Ih, Ij, Ik, Il$^{1-3}$, Im$^{1-3}$, In$^{1-3}$, Io$^{1-2}$, Ip$^{1-9}$, Iq$^{1-9}$, Ir$^{1-9}$ or Is$^{1-3}$ of the invention.

The present invention further provides methods of inhibiting or reducing production of cortisol in a cell using a compound of Formula I, I*, Ia, Ib, Ic, Id, Ie, or If of the invention.

The present invention further provides methods of increasing insulin sensitivity in a subject in need thereof using a compound of Formula I, I*, Ia, Ib, Ic, Id, Ie, If, If*, Ig, Ih, Ij, Ik, Il$^{1-3}$, Im$^{1-3}$, In$^{1-3}$, Io$^{1-2}$, Ip$^{1-9}$, Iq$^{1-9}$, Ir$^{1-9}$ or Is$^{1-3}$ of the invention.

The present invention further provides methods of treating a subject with a disease associated with activity of expression of 11β-HSD1 using a compound of Formula I, I*, Ia, Ib, Ic, Id, Ie, If, If*, Ig, Ih, Ij, Ik, Il$^{1-3}$, Im$^{1-3}$, In$^{1-3}$, Io$^{1-2}$, Ip$^{1-9}$, Iq$^{1-9}$, Ir$^{1-9}$ or Is$^{1-3}$ of the invention.

In certain specific embodiments of the invention, the variables in the above-described structural formulas have the following values:

A$^1$ is a bond. Alternatively, A$^1$ is (C$_1$-C$_3$)alkylene. In another specific embodiment, A$^1$ is methylene. In another specific embodiment, if R$^1$ is present, A$^1$ is CH.

R$^1$ is (a) absent or (b) is selected from (C$_1$-C$_6$)alkyl, (C$_2$-C$_6$)alkenyl, (C$_2$-C$_6$)alkynyl or (C$_1$-C$_3$)alkoxy(C$_1$-C$_3$)alkyl, wherein each is optionally substituted with up to four groups independently selected from fluorine, cyano, oxo, R$^4$, R$^4$O—, (R$^4$)$_2$N—, R$^4$O$_2$C—, R$^4$S, R$^4$S(=O)—, R$^4$S(=O)$_2$—, R$^4$C(=O)NR$^4$—, (R$^4$)$_2$NC(=O)—, (R$^4$)$_2$NC(=O)O—, (R$^4$)$_2$NC(=O)NR$^4$—, R$^4$OC(=O)NR$^4$—, (R$^4$)$_2$NC(=NCN)NR$^4$—, (R$^4$O)$_2$P(=O)O—, (R$^4$O)$_2$P(=O)NR$^4$—, R$^4$OS(=O)$_2$NR$^4$—, (R$^4$)$_2$NS(=O)$_2$O—, (R$^4$)$_2$NS(=O)$_2$NR$^4$—, R$^4$S(=O)$_2$NR$^4$—, R$^4$S(=O)$_2$NHC(=O)—, R$^4$S(=O)$_2$NHC(=O)O—, R$^4$S(=O)$_2$NHC(=O)NR$^4$—, R$^4$OS(=O)$_2$NHC(=O)—, R$^4$OS(=O)$_2$NHC(=O)O—, $R^4OS(=O)_2NHC(=O)NR^4—$, $(R^4)_2NS(=O)_2NHC(=O)—$, $(R^4)_2NS(=O)_2NHC(=O)O—$, $(R^4)_2NS(=O)_2NHC(=O)NR^4—$, $R^4C(=O)NHS(=O)_2—$, $R^4C(=O)NHS(=O)_2O—$, $R^4C(=O)NHS(=O)_2NR^4—$, $R^4OC(=O)NHS(=O)_2—$, $R^4OC(=O)NHS(=O)_2O—$, $R^4OC(=O)NHS(=O)_2NR^4—$, $(R^4)_2NC(=O)NHS(=O)_2—$, $(R^4)_2NC(=O)NHS(=O)_2O—$, $(R^4)_2NC(=O)NHS(=O)_2NR^4—$, aryl, cycloalkyl, heterocyclyl, heteroaryl, arylamino and heteroarylamino. Alternatively, $R^1$ is (a) absent or (b) is selected from $(C_1-C_6)$alkyl, $(C_2-C_6)$alkenyl, $(C_2-C_6)$alkynyl or $(C_1-C_3)$alkoxy$(C_1-C_3)$alkyl, wherein each is optionally substituted with up to four groups independently selected from fluorine, cyano, oxo, $R^4$, $R^4O—$, $(R^4)_2N—$, $R^4O_2C—$, $R^4S$, $R^4S(=O)—$, $R^4S(=O)_2—$, $R^4C(=O)NR^4—$, $(R^4)_2NC(=O)—$, $(R^4)_2NC(=O)O—$, $(R^4)_2NC(=O)NR^4—$, $R^4OC(=O)NR^4—$, $(R^4)_2NC(=NCN)NR^4—$, $(R^4O)_2P(=O)O—$, $(R^4O)_2P(=O)NR^4—$, $R^4OS(=O)_2NR^4—$, $(R^4)_2NS(=O)_2O—$, $(R^4)_2NS(=O)_2NR^4—$, $R^4S(=O)_2NR^4—$, $R^4S(=O)_2NHC(=O)—$, $R^4S(=O)_2NHC(=O)O—$, $R^4S(=O)_2NHC(=O)NR^4—$, $R^4OS(=O)_2NHC(=O)—$, $R^4OS(=O)_2NHC(=O)O—$, $R^4OS(=O)_2NHC(=O)NR^4—$, $(R^4)_2NS(=O)_2NHC(=O)—$, $(R^4)_2NS(=O)_2NHC(=O)O—$, $(R^4)_2NS(=O)_2NHC(=O)NR^4—$, $R^4C(=O)NHS(=O)_2—$, $R^4C(=O)NHS(=O)_2O—$, $R^4C(=O)NHS(=O)_2NR^4—$, $R^4OC(=O)NHS(=O)_2—$, $R^4OC(=O)NHS(=O)_2O—$, $R^4OC(=O)NHS(=O)_2NR^4—$, $(R^4)_2NC(=O)NHS(=O)_2—$, $(R^4)_2NC(=O)NHS(=O)_2O—$, $(R^4)_2NC(=O)NHS(=O)_2NR^4—$, heterocyclyl, heteroaryl, arylamino and heteroarylamino. In another alternative, $R^1$ is $(C_1-C_6)$alkyl. Alternatively, $R^1$ is methyl or ethyl.

$Cy^1$ is optionally substituted aryl or optionally substituted heteroaryl. Alternatively, $Cy^1$ is optionally substituted phenyl or optionally substituted pyridyl. In another alternative, $Cy^1$ is optionally substituted monocyclic cycloalkyl. In another alternative, $Cy^1$ is optionally substituted cyclohexyl. In another alternative, $Cy^1$ is optionally substituted phenyl. In yet another specific embodiment, $Cy^1$ is substituted with fluorine chlorine, bromine, methoxy, methoxycarbonyl, carboxy, methyl, trifluoromethyl or difluoromethoxy. In yet another specific embodiment, $Cy^1$ is substituted with fluorine or bromine. In another embodiment $A^2$ is a bond, $Cy^2$ is H and $Cy^1$ is optionally substituted monocyclic cycloalkyl. In another embodiment $A^2$ is a bond, $Cy^2$ is H and $Cy^1$ is optionally substituted cyclohexyl. In another embodiment $A^2$ is a bond, $Cy^2$ is H and $Cy^1$ is phenyl substituted with fluorine, chlorine, bromine, methyl, methoxy, methoxycarbony, trifluoromethyl, hydroxymethyl or 2-hydroxy-2-propyl.

$A^2$ is a bond and $Cy^2$ is hydrogen. Alternatively, $A^2$ is a bond and $Cy^2$ is cyclopropyl. Alternatively, $A^2$ is a bond and $Cy^2$ is optionally substituted aryl or optionally substituted heteroaryl. In another specific embodiment, $A^2$ is a bond and $Cy^2$ is optionally substituted phenyl or optionally substituted pyridyl. In yet another specific embodiment, $A^2$ is a bond and $Cy^2$ is optionally substituted phenyl. In yet another specific embodiment, $A^2$ is a bond and $Cy^2$ is substituted with 1 to 4 groups independently selected from chlorine or fluorine. In yet another specific embodiment, $A^2$ is a bond and $Cy^2$ is difluorophenyl. In yet another specific embodiment, $A^2$ is a bond and $Cy^2$ is fluorophenyl. In yet another specific embodiment $A^2$ is a bond and $Cy^2$ is optionally substituted 2-thienyl, 1-pyrazolyl, 3-pyrazolyl, 1,2,4-thiadiazol-3-yl, thiazolyl or 2-oxo-1,2-dihydro-5-pyridyl. In yet another specific embodiment, $A^2$ is a bond and $Cy^2$ is phenyl or thienyl substituted with amino$(C_1-C_6)$alkyl.

In a specific embodiment, E is a bond. In another specific embodiment, E is a bond when $R^2$ is optionally substituted aryl, optionally substituted heteroaryl or optionally substituted cycloalkyl. In another specific embodiment, E is a bond when $R^2$ is optionally substituted phenyl, optionally substituted thienyl or optionally substituted pyridyl. In yet another specific embodiment, E is a bond when $R^2$ is optionally substituted phenyl.

$R^3$ is hydroxy$(C_2-C_5)$alkyl. In yet another specific embodiment $R^3$ is 3-hydroxypropyl, 2-hydroxypropyl, 2-hydroxyethyl, 2-hydroxy-2-methylpropyl, 3-hydroxybutyl or 3-hydroxy-3-methylbutyl. Alternatively, $R^3$ is dihydroxy$(C_3-C_5)$alkyl. In yet another specific embodiment $R^3$ is 2,3-dihydroxypropyl. In another specific embodiment, $R^3$ is $\omega$-H$_2$NCO$(C_1-C_3)$alkyl. In yet another specific embodiment $R^3$ is $H_2NC(=O)CH_2CH_2—$.

In yet another specific embodiment, $R^3$ is $(C_1-C_2)$alkoxy$(C_1-C_3)$alkyl. In yet another specific embodiment, $R^3$ is $H_2NSO_2O(C_2-C_4)$alkyl. In yet another specific embodiment, $R^3$ is $H_2NSO_2NH(C_2-C_4)$alkyl. In yet another specific embodiment, $R^3$ is oxo$(C_2-C_4)$alkyl. In yet another specific embodiment, $R^3$ is $MeCOCH_2$. In yet another specific embodiment, $R^3$ is alkenyl. In yet another specific embodiment, $R^3$ is allyl. In yet another specific embodiment, $R^3$ is $MeC(=O)NH(C_2-C_4)$alkyl. In yet another specific embodiment, $R^3$ is $MeOC(=O)NH(C_2-C_4)$alkyl. In yet another specific embodiment, $R^3$ is cyanoalkyl. In yet another specific embodiment, $R^3$ is alkylsulfonylaminoalkyl. In yet another specific embodiment $R^3$ is $MeSO_2NH(C_2-C_4)$alkyl. In yet another specific embodiment $R^3$ is $MeSO_2NHCH_2CH_2CH_2—$. In yet another specific embodiment, $R^3$ is hydroxyalkoxyalkyl. In yet another specific embodiment, $R^3$ is aminocarbonylaminoalkyl. In yet another specific embodiment, $R^3$ is aminocarboxyalkyl. In yet another specific embodiment $R^3$ is 2-(4-morpholino)ethyl. In yet another specific embodiment $R^3$ is 2-(1-imidazolyl)ethyl.

$R^2$ is optionally substituted aryl, optionally substituted heteroaryl or cycloalkyl or alkyl. In one specific embodiment, $R^2$ is optionally substituted phenyl, optionally substituted pyridyl or optionally substituted thienyl. In another embodiment, $R^2$ is optionally substituted alkyl. In one specific embodiment, $R^2$ is optionally substituted isopropyl. In one specific embodiment, $R^2$ is. In another specific embodiment, $R^2$ is optionally substituted phenyl. In yet another specific embodiment, $R^2$ is fluorophenyl.

Another embodiment of the invention is a compound of Formulas I, I*, Ia, Ib, Ic, Id, Ie, If, If*, Ig, Ih, Ij, Ik, Il$^{1-3}$, Im$^{1-3}$, In$^{1-3}$, Io$^{1-2}$, Ip$^{1-9}$, Iq$^{1-9}$, Ir$^{1-9}$ or Is$^{1-3}$ or a pharmaceutically acceptable salt, enantiomer or diastereomer thereof, wherein the following proviso applies to the compounds disclosed herein and methods of use thereof:

If E is a bond or $C_1$alkylene, $R_2$ is aryl, heteroaryl or heterocyclyl, $A^1$ is $(C_1)$alkylene, $R^3$ is optionally fluorinated $(C_1-C_5)$alkyl, $(C_2-C_5)$alkenyl or $(C_2-C_6)$alkynyl and $Cy^2$ is optionally substituted phenyl, then $Cy^1$ is not substituted at the ortho position by optionally substituted aryl, heteroaryl or cycloalkyl.

Another embodiment of the invention is the use of a compound of Formulas I, I*, Ia, Ib, Ic, Id, Ie, If, If*, or Ig, or a pharmaceutically acceptable salt, enantiomer or diastereomer thereof for the manufacture of a medicament for inhibiting 11β-HSD1 activity in a mammal in need of such treatment or for any of the other uses described herein.

Another embodiment of the invention is the use of a compound of Formulas I, I*, Ia, Ib, Ic, Id, Ie, If, If*, or Ig, or a pharmaceutically acceptable salt, enantiomer or diastereomer thereof for the manufacture of a medicament for treating a subject with a disease associated with the activity or expression of 11β-HSD1 or for any of the other uses described herein.

DEFINITIONS

The term "alkyl" means a straight or branched hydrocarbon radical having 1-10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "cycloalkyl" means a monocyclic, bicyclic or tricyclic, saturated hydrocarbon ring having 3-10 carbon atoms and includes, for example, cyclopropyl, cyclobutyl, cyclopentyl, cyclohexyl, cycloheptyl, cyclooctyl, bicyclo[2.2.2]octyl, bicyclo[2.2.1]heptyl, Spiro[4.4]nonane, adamantyl and the like.

The term "aryl" means an aromatic radical which is a phenyl group, a naphthyl group, an indanyl group or a tetrahydronaphthalene group. When substituted, an aryl group can be optionally substituted with 1-4 substituents. Exemplary substituents include alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido.

The term "heteroaryl" means a 5- and 6-membered heteroaromatic radical which may optionally be fused to a saturated or unsaturated ring containing 0-4 heteroatoms selected from N, O, and S and includes, for example, a heteroaromatic radical which is 2- or 3-thienyl, 2- or 3-furanyl, 2- or 3-pyrrolyl, 2-,3-, or 4-pyridyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, 5-, 6-, 7- or 8-quinazolinyl, 2-, 3-, 5-, 6-, 7- or 8-quinoxalinyl, 2-, 3-, 4-, 5-, 6-, 7- or 8-quinolinyl, 1-, 3-, 4-, 5-, 6-, 7- or 8-isoquinolinyl, 2-, 4-, or 5-thiazolyl, 2-, 3-, 4-, or 5-pyrazolyl, 2-, 3-, 4-, or 5-imidazolyl. When substituted, a heteroaryl can be optionally substituted with 1 to 4 substitutents. Exemplary substituents include alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido, or by oxo to form an N-oxide.

The term "heterocyclyl" means a 4-, 5-, 6- and 7-membered saturated or partially unsaturated heterocyclic ring containing 1 to 4 heteroatoms independently selected from N, O, and S. Exemplary heterocyclyls include pyrrolidine, pyrrolidin-2-one, 1-methylpyrrolidin-2-one, piperidine, piperidin-2-one, 2-pyridone, 4-pyridone, piperazine, 1-(2,2,2-trifluoroethyl)piperazine, piperazin-2-one, 5,6-dihydropyrimidin-4-one, pyrimidin-4-one, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide and isothiazolidine 1,1-dioxide. When substituted, a heterocyclyl can be optionally substituted with 1-4 substituents. Exemplary substituents include alkyl, haloalkyl and oxo.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms.

"Racemate" or "racemic mixture" means a compound of equimolar quantities of two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration.

"R," "S," "S*," "R*," "E," "Z," "cis," and "trans," indicate configurations relative to the core molecule.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When a disclosed compound is named or depicted by structure without indicating the stereochemistry, and the compound has at least one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable acidic/anionic salts include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphospate, polygalacturonate, salicylate, stearate, subacetate, succinate, sulfate, hydrogensulfate, tannate, tartrate, teoclate, tosylate, and triethiodide salts.

Pharmaceutically acceptable basic/cationic salts include, the sodium, potassium, calcium, magnesium, diethanolamine, n-methyl-D-glucamine, L-lysine, L-arginine, ammonium, ethanolamine, piperazine and triethanolamine salts.

The following abbreviations have the indicated meanings:

| Abbreviation | Meaning |
|---|---|
| Boc | tert-butoxy carbonyl or t-butoxy carbonyl |
| (Boc)$_2$O | di-tert-butyl dicarbonate |
| Cbz | Benzyloxycarbonyl |
| CbzCl | Benzyl chloroformate |
| DAST | diethylaminosulfur trifluoride |
| DBU | 1,8-diazabicyclo[5.4.0]undec-7-ene |
| DCC | N,N'-dicyclohexylcarbodiimide |
| DCM | dichloromethane |
| DCU | N,N'-dicyclohexylurea |
| DIAD | diisopropyl azodicarboxylate |
| DIEA | N,N-diisopropylethylamine |
| DMAP | 4-(dimethylamino)pyridine |
| DMF | N,N-dimethylformamide |
| DMPU | 1,3-dimethyl-3,4,5,6-tetrahydro-2(1H)-pyrimidinone |
| 2,4-DNP | 2,4-dinitrophenylhydrazine |
| DPTBS | Diphenyl-t-butylsilyl |
| EDC•HCl, EDCl | 1-[3-(dimethylamino)propyl]-3-ethylcarbodiimide hydrochloride |
| EDTA | ethylenediaminetetraacetic acid |
| Equiv | equivalents |
| Fmoc | 1-[[(9H-fluoren-9-ylmethoxy)carbonyl]oxy]- |
| Fmoc—OSu | 1-[[(9H-fluoren-9-ylmethoxy)carbonyl]oxy]-2,5-pyrrolidinedione |
| h, hr | hour(s) |
| HOBt | 1-hydroxybenzotriazole |
| HATU | 2-(7-Aza-1H-benzotriazole-1-yl)-1,1,3,3-tetramethyluronium hexafluorophosphate |
| HBTU | 2-(1H-Benzotriazol-1-yl)-1,1,3,3-tetramethyluronium hexafluorophosphate |
| KHMDS | potassium hexamethyldisilazane |
| LAH or LiAlH$_4$ | lithium aluminum hydride |
| LC-MS | liquid chromatography-mass spectroscopy |
| LHMDS | lithium hexamethyldisilazane |
| Me | methyl |
| MsCl | methanesulfonyl chloride |
| Min | minute |
| MS | mass spectrum |
| NaH | sodium hydride |
| NaHCO$_3$ | sodium bicarbonate |
| NaN$_3$ | sodium azide |
| NaOH | sodium hydroxide |
| Na$_2$SO$_4$ | sodium sulfate |
| NMM | N-methylmorpholine |
| NMP | N-methylpyrrolidinone |
| Pd$_2$(dba)$_3$ | tris(dibenzylideneacetone)dipalladium(0) |
| PE | petroleum ether |
| PCC | pyridinium chlorochromate |
| Quant | quantitative yield |
| Satd | saturated |
| SOCl$_2$ | thionyl chloride |
| SFC | supercritical fluid chromatography |
| SPA | scintillation proximity assay |
| SPE | solid phase extraction |
| TBAF | tetrabutylammonium fluoride |
| TBS | t-butyldimethylsilyl |
| TBDPS | t-butyldiphenylsilyl |
| TBSCl | t-butyldimethylsilyl chloride |
| TBDPSCl | t-butyldiphenylsilyl chloride |
| TEA | triethylamine or Et$_3$N |
| TEMPO | 2,2,6,6-tetramethyl-1-piperidinyloxy free radical |
| Teoc | 1-[2-(trimethylsilyl)ethoxycarbonyloxy]- |
| Teoc-OSu | 1-[2-(trimethylsilyl)ethoxycarbonyloxy]pyrrolidin-2,5-dione |
| TFA | trifluoroacetic acid |
| Tlc, TLC | thin layer chromatography |
| TMS | trimethylsilyl |
| TMSCl | chlorotrimethylsilane or trimethylsilyl chloride |
| $t_R$ | retention time |
| TsOH | p-toluenesulfonic acid |

General Description of Synthetic Methods

Compounds of Formula I can be prepared by several processes. In the discussion below, $A^1$, $A^2$, $Cy^1$, $Cy^2$, E, $R^1$, $R^2$, $R^3$, Y and n have the meanings indicated above unless otherwise noted. In cases where the synthetic intermediates and final products of Formulas I described below contain potentially reactive functional groups, for example amino, hydroxyl, thiol and carboxylic acid groups, that may interfere with the desired reaction, it may be advantageous to employ protected forms of the intermediate. Methods for the selection, introduction and subsequent removal of protecting groups are well known to those skilled in the art. (T. W. Greene and P. G. M. Wuts "Protective Groups in Organic Synthesis" John Wiley & Sons, Inc., New York 1999). Such protecting group manipulations are assumed in the discussion below and not described explicitly. Generally, reagents in the reaction schemes are used in equimolar amounts; however, in certain cases it may be desirable to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

In a first process compounds of Formula I, wherein $R^3$ is allyl, can be prepared from compounds of Formula II by reaction with allyltrimethylsilane in the presence of TiCl$_4$:

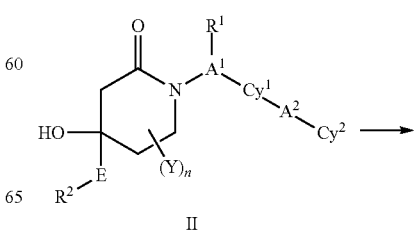

II

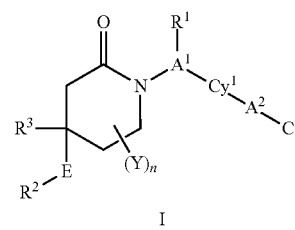

I

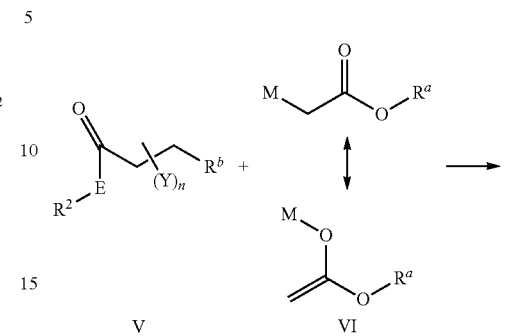

V    VI

VI, wherein M is for example ZnBr (reformatsky reaction). Acetate ester enolates of Formula VI, wherein M is ZnBr, are prepared from esters of bromoacetic acid and zinc metal.

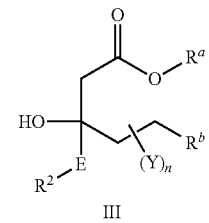

III

Compounds of Formula II can be prepared by reaction of compounds of Formula III, wherein $R^a$ is a lower alkyl group such as methyl or ethyl and $R^b$ is a leaving group such as chloride, bromide, alkanesulfonate, arylsulfonate or haloalkanesulfonate, with amines of Formula IV.

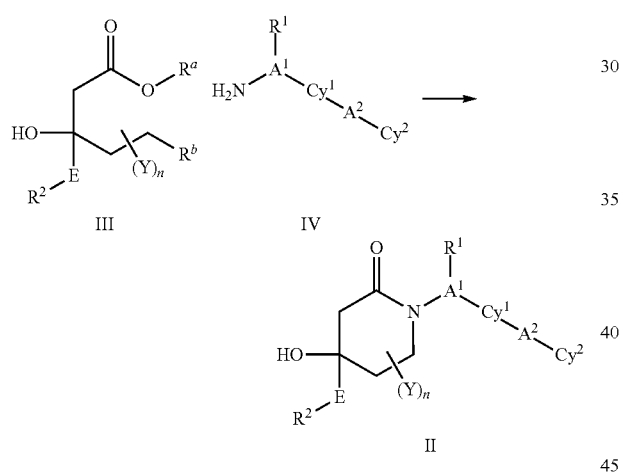

III    IV

II

Amine intermediates of Formula IV, wherein $A^1$=$CH_2$ and $R^1$ is absent, can be prepared by reduction of amides of Formula VII using a hydride reagent such as $BH_3$.THF solution, $BH_3$.$Me_2$S or $LiAlH_4$ in an inert solvent ethereal such as THF or DME at 20° C. to 100° C. for between 1 h and 48 h:

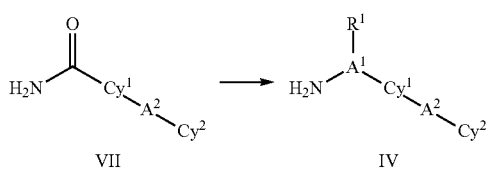

VII    IV

Compounds of Formula III can be prepared by reaction of ketones of Formula V with acetate ester enolates of Formula Amine intermediates of Formula IV, wherein $A^1$ is a bond, $R^1$ is absent and $Cy^1$ is not an aromatic or heteroaromatic ring, can be prepared from ketones of formula VIII via oximes of Formula IX or by reductive amination of a ketone of Formula VIII with ammonia:

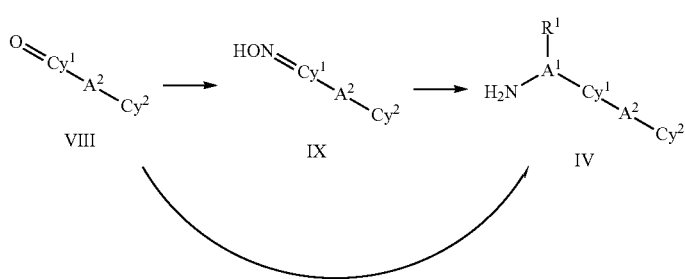

VIII    IX    IV

Methods for the conversion of ketones to oximes are described in Smith, M. B. and March, J. "March's Advanced Organic Chemistry" pp 1194-1195, 5th Edition, Wiley, New York, N.Y., 2001. Methods for the reduction of oximes to primary amines are described in Smith, M. B. and March, J. "March's Advanced Organic Chemistry" p 1555, 5th Edition, Wiley, New York, N.Y., 2001. Methods for the reductive amination of ketones are described in Baxter, E. W. and Reitz, A. B. "Organic Reactions" Volume 59, Ed. Overman, L. E., Wiley Interscience, 2002.

Amine intermediates of Formula IV, wherein $A^1$ is CH, can be prepared from ketones of Formula X by reductive amination with ammonia.

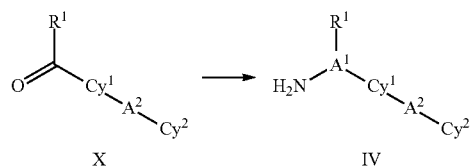

Amine intermediates of Formula IV, wherein $A^1$ is CH, can be prepared from alcohols of Formula XI via azides of Formula XII. The conversion of alcohols of Formula XI to an azide of Formula XII can be accomplished with, for example, diphenylphosphoryl azide. Reduction of azides of Formula XII to amines of Formula IV can be effected, for example, by hydrogenation in the presence of a palladium catalyst or by triphenylphosphine in wet THF.

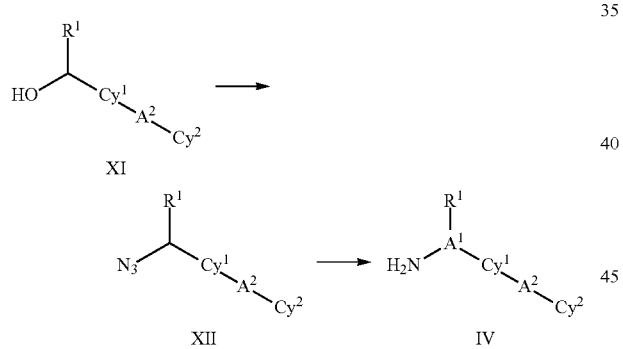

Amine intermediates of Formula IV, wherein $A^1$ is CH, can be prepared by reaction of sulfimine intermediates of Formula XIII with organometallic reagents of Formula XIV, wherein M is Li, MgCl, MgBr or MgI, followed by treatment with acid to remove the t-butylsulfinyl group.

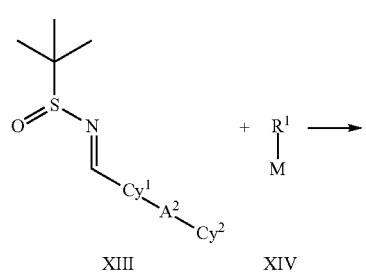

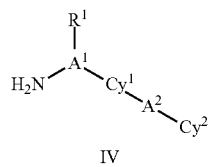

Sulfimines of Formula XIII can be prepared by treatment of aldehyde intermediates of Formula XV with t-butylsulfinamide.

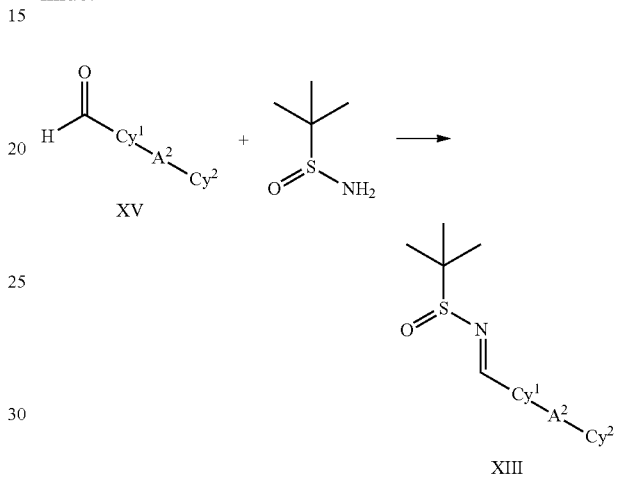

In a second process, compounds of Formula I, wherein $A^1$ is CH and $R^1$ is H, can be prepared by reaction of lactam intermediates of Formula XIV with alkylating agents of Formula XVII, wherein $R^b$ is a leaving group such as chloride, bromide, alkanesulfonate, arylsulfonate or haloalkanesulfonate, using a base such as sodium hydride.

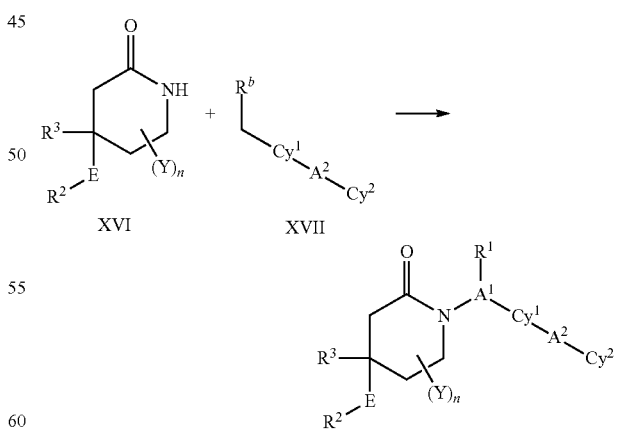

Lactam intermediates of Formula XVI can be prepared from aminoester intermediates of Formula XVII.

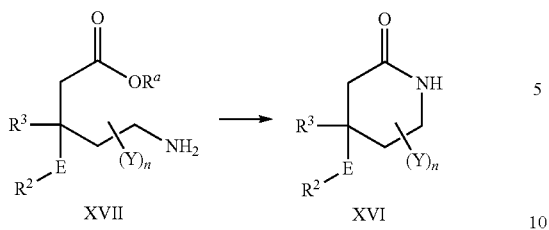

Aminoester intermediates of Formula XVII, wherein n=0, can be prepared by reduction of cyanoesters of Formula XVIII using, for example, hydrogen gas and PtO$_2$ catalyst.

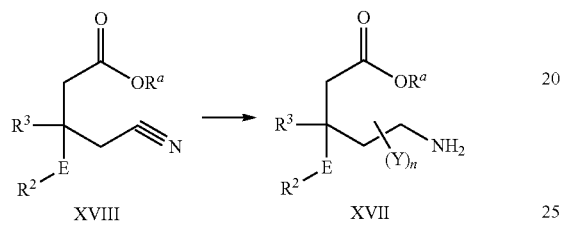

Cyanoester intermediates of Formula XVIII can be prepared by addition of acetate ester enolates of Formula VI, wherein M=Li, to enoates of Formula XIX, followed by decarboalkoxylation.

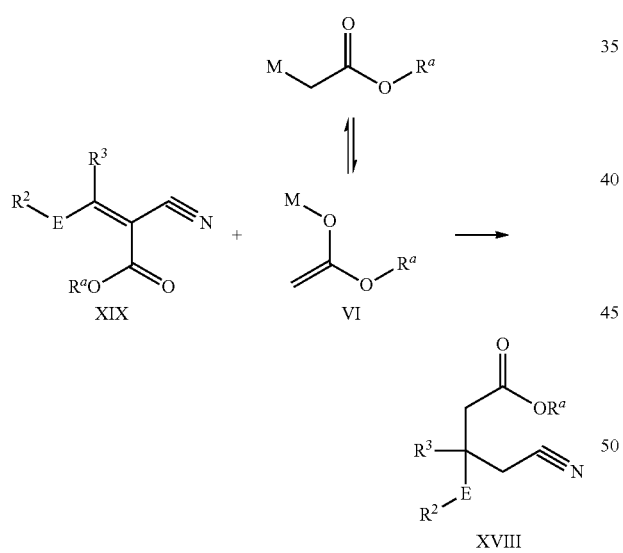

Enoate intermediates of Formula XIX can be prepared by Knoevenagel reaction of ketones of Formula XX and cyanoacetate esters of Formula XXI.

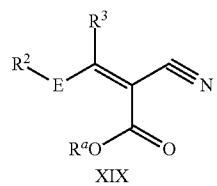

Lactam intermediates of Formula XVI can also be prepared by Beckman rearrangement of cyclopentanones of Formula XXII by treatment with hydroxylamine to form the corresponding oximes followed by acid catalyst, for example polyphosphoric acid:

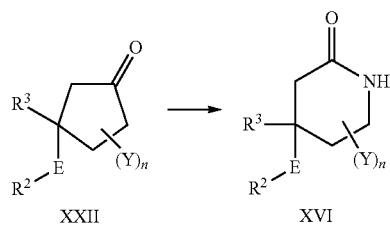

3-methyl-3-phenylcyclopentanones (XXII wherein R$^2$=Ph, E=bond and R$^3$=Me) and various other 3-alkyl-3-(optionally substituted phenyl)cyclopentanones have been reported in the literature.

In a third process, compounds of Formula I, wherein n=0, can be prepared by oxidation of a piperidines of Formula XXIII. Oxidation may be effected using, for example, Hg(OAc)$_2$ in the presence of EDTA or bromine in acetic acid.

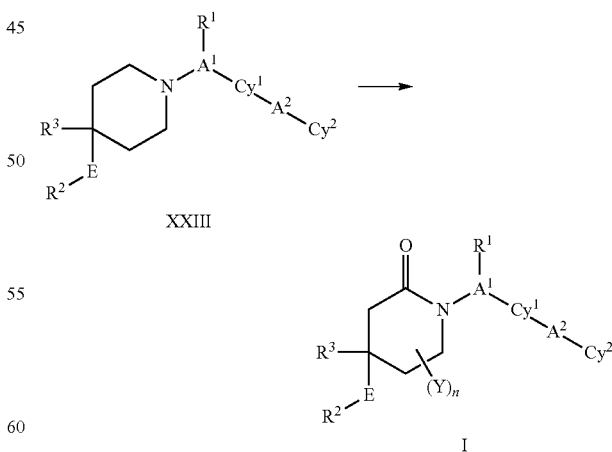

Piperidines of Formula XXIII can be prepared by reaction of intermediates of Formula XXIV, wherein the two instances of $R^b$ are independently selected from leaving groups such as chloride, bromide, alkanesulfonate, arylsulfonate or haloalkanesulfonate, and amine intermediates of Formula IV.

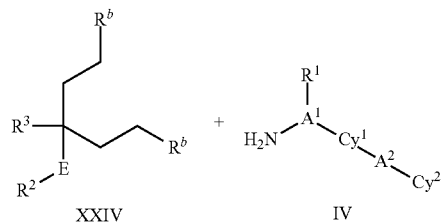

Intermediates of Formula XXIV, wherein $R^b$ is alkanesulfonate, arylsulfonate or haloalkanesulfonate, can be prepared from diols of Formula XXV by treatment with an alkylsulfonyl halide e.g. methanesulfonyl chloride, an arylsulfonyl halide e.g. p-toluenesulfonyl chloride or a haloalkanesulfonic anhydride e.g. triflic anhydride. Intermediates of Formula XXIV, wherein $R^b$ is bromide can be prepared by treatment of diols of Formula XXV with HBr in HOAc, with $Ph_3P/CBr_4$ or with $PBr_3$.

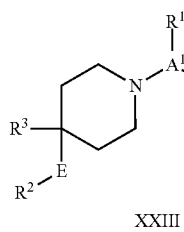

Diols of Formula XXV, wherein $R^3$ is allyl, E is a bond and $R^2$ is optionally substituted phenyl, can be prepared by reaction of triols of Formula XXVI with allyltrimethylsilane in the presence of a Lewis acid.

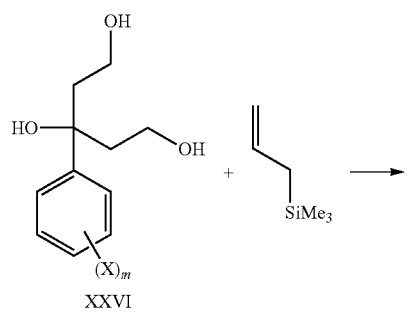

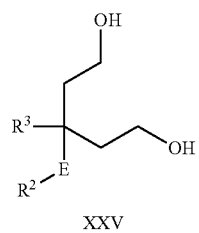

Triols of Formula XXVI can be prepared by ozonolysis and reduction of dienes of Formula XXVII.

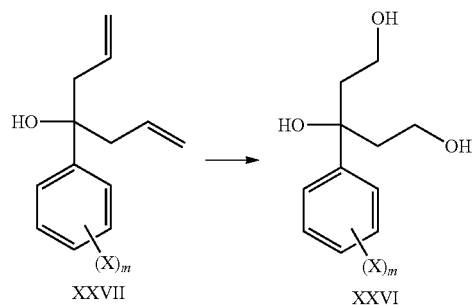

Dienes of Formula XXVII can be prepared by addition of at least 2 equivalents of allyl Grignard to benzoic acid esters of Formula XXVIII.

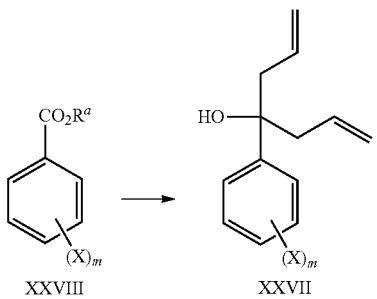

Diols of Formula XXV, wherein $R^3$ is an alkyl group, can be prepared by ozonolysis and reduction of dienes of Formula XXIX.

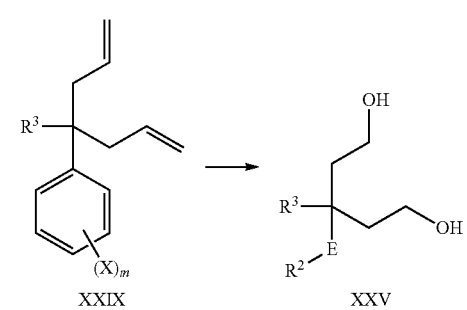

Dienes of Formula XXIX can be prepared from ketones of Formula XXX by treatment with allyltrimethylsilane in the presence of a Lewis acid such as $InCl_3$ or $TiCl_4$.

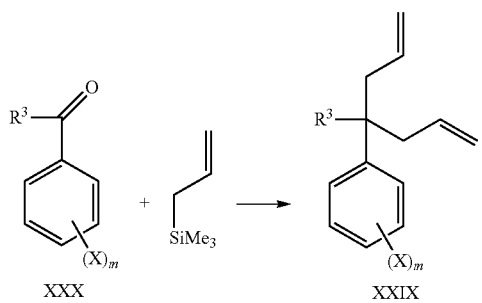

In a fourth process, compounds of Formula I, wherein n is 0, can be prepared by conjugate addition of organometallic reagents of Formula XXXI, especially organocuprates, wherein M is $CuLiR^3$ or CuLiCN, to α,β-unsaturated lactams of Formula XXXII.

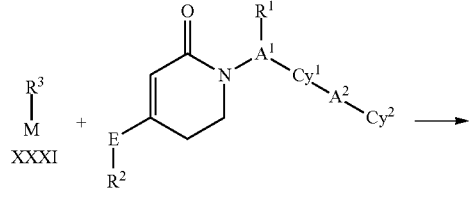

α,β-unsaturated lactams of Formula XXXII can be prepared by oxidation of tetrahydropyridines of Formula XXXIII, with for example $KMnO_4$.

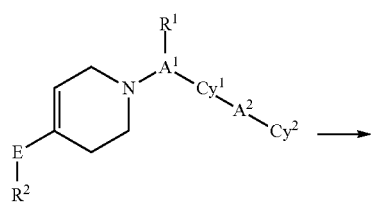

Tetrahydropyridines of Formula XXXIII, wherein E is a bond and $R^2$ is optionally substituted phenyl, can be prepared by addition of organometallic reagents of Formula XXXIV, wherein M is Li, MgCl, MgBr or MgI, to 4-oxopiperidines of Formula XXXV, followed by dehydration.

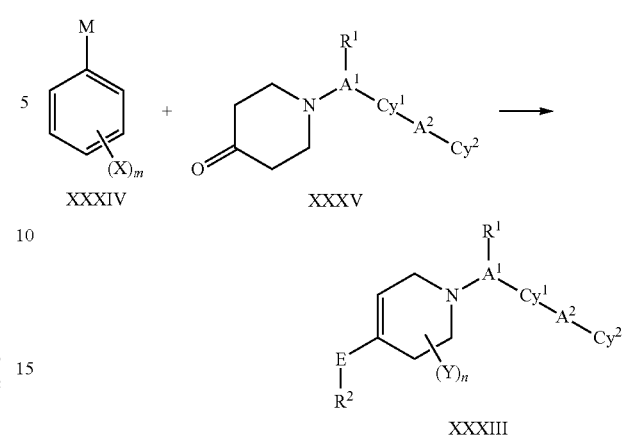

In a fifth process, compounds of Formula I, wherein n is 0, can be prepared by conjugate addition of organometallic reagents of Formula XXXVI, especially organocuprates wherein M is $CuLiER^2$ or CuLiCN, to α,β-unsaturated lactams of Formula XXXVII.

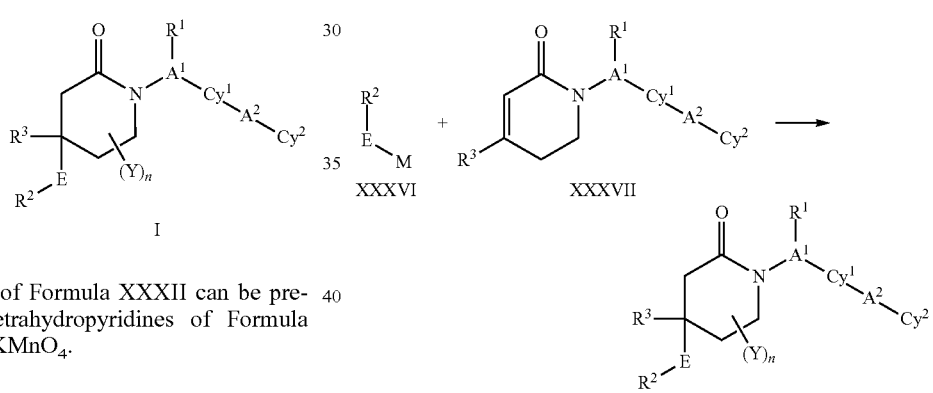

α,β-unsaturated lactams of Formula XXXVII can be prepared following procedures similar to those described for XXXII.

α,β-unsaturated lactams of Formula XXXII, wherein $A^1$ is $CH_2$ and $R^1$ is absent, can be prepared by reaction of α,β-unsaturated lactams of Formula XXXVIII with alkylating agents of Formula XVII, wherein $R^b$ is a leaving group such as chloride, bromide, alkanesulfonate, arylsulfonate or haloalkanesulfonate, using a base such as sodium hydride.

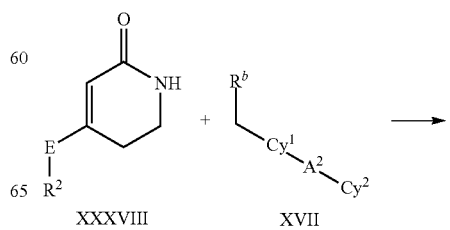

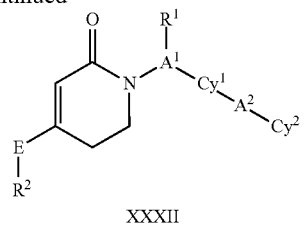

XXXII

In a sixth process, compounds of Formula I, wherein n is 0, can be prepared from imides of Formula XXXIX by reduction with hydride reducing agents, for example LiAlH₄.

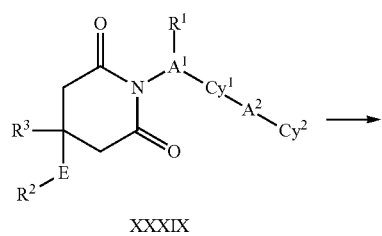

XXXIX

↓

I

Imides of Formula XXXIX can be prepared from anhydrides of Formula XL and amines of Formula IV.

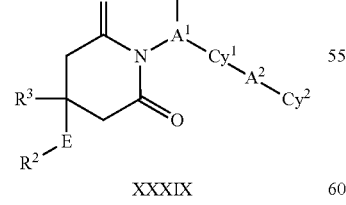

XL     IV

↓

XXXIX

In a seventh process, compounds of Formula I, wherein R³ is 2-hydroxyethyl, can be prepared by intramolecular rearrangement of aminolactones of Formula XLI.

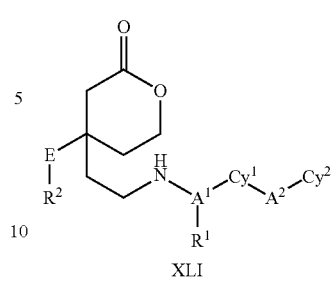

XLI

↓

I

Aminolactones of Formula XLI can be prepared by reductive amination of aldehydes of Formula XLII with amines of Formula IV using, for example, hydride reducing agents such as NaCNBH₃ or NaB(OAC)₃H.

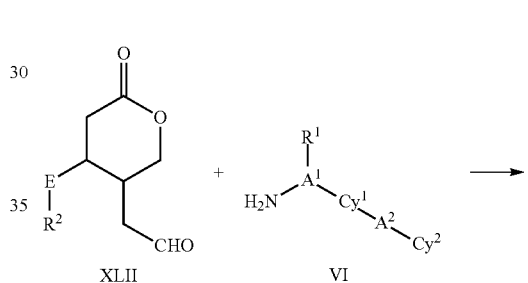

XLII     VI

↓

XLI

Aldehydes of Formula XLII can be prepared by oxidation of hydroxylactols of Formula XLIII with, for example, PCC.

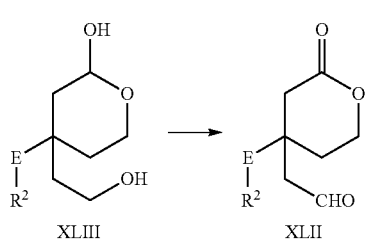

XLIII     XLII

Hydroxylactols of Formula XLIII can be prepared by ozonolysis of trienes of Formula XLIV.

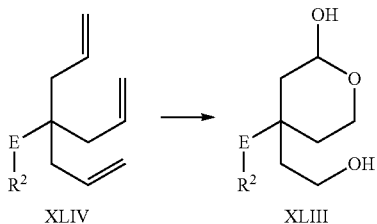

The triene of Formula XLIV, wherein E is a bond and $R^2$ is phenyl, can be prepared by diazotization of a triene of Formula XLV and reduction with hypophosphorus acid.

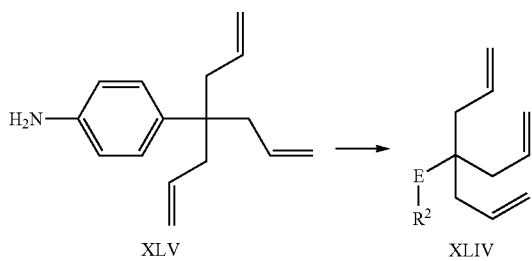

The preparation of XLV has been described in *J. Org. Chem.* 2005, 70, 7972-7978.

In a ninth process, a compound of Formula I, wherein $A^1$ is a bond, $R^1$ is absent and $Cy^1$ is aryl or heteroaryl, is prepared by reaction of a lactam of Formula XVI with a halide of Formula XLVI, wherein $R^b$ is a halogen, preferably bromine or iodine, and $Cy^1$ is aryl or heteroaryl, in the presence of a copper or palladium catalyst.

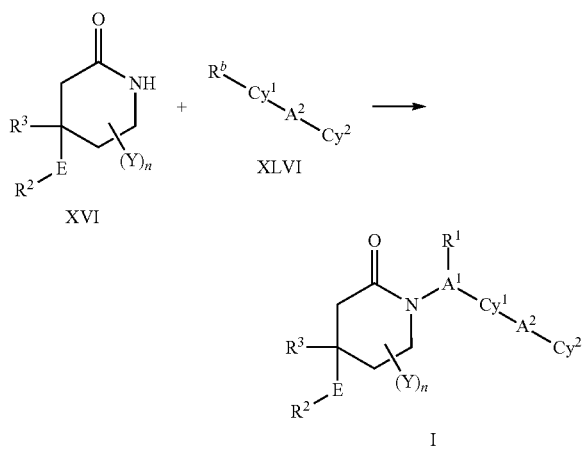

In a tenth process a compound of Formula I can be prepared from another compound of Formula I. For example:

(1) a compound of Formula I wherein $Cy^1$ is substituted with bromine or iodine, $A^2$ is a bond and $Cy^2$ is hydrogen can be reacted with an optionally substituted aryl or heteroarylboronic acid or ester in the presence of a palladium catalyst to give a compound of Formula I wherein $A^2$ is a bond and $Cy^2$ is optionally substituted aryl or heteroaryl.

(2) a compound of Formula I wherein $R^1$ or $R^3$ is ω-hydroxy($C_2$-$C_6$)alkyl can be oxidized to a compound of Formula I wherein $R^1$ or $R^3$ is ω-carboxy($C_1$-$C_6$)alkyl using Jones reagent.

(3) a compound of Formula I wherein $R^1$ or $R^3$ is ω-carboxy($C_1$-$C_6$)alkyl can be coupled with ammonia or a ($C_1$-$C_6$) alkylamine using a standard peptide coupling reagent such as EDC to afford a compound of Formula I wherein $R^1$ or $R^3$ is ω-$H_2NC(=O)$($C_1$-$C_6$)alkyl or ω-{($C_1$-$C_6$)alkylNHC(=O)} ($C_1$-$C_6$)alkyl (4) a compound of Formula I wherein $R^1$ or $R^3$ is ω-hydroxy($C_1$-$C_6$)alkyl can be converted to its methanesulfonate or trifluoromethanesulfonate, treated with sodium azide and reduced to give a compound of Formula I, wherein $R^1$ or $R^3$ is ω-amino($C_1$-$C_6$)alkyl.

(5) a compound of Formula I wherein $R^1$ or $R^3$ is amino ($C_1$-$C_6$)alkyl can be reacted with acetic anhydride or acetyl chloride to give a compound of Formula I wherein $R^1$ or $R^3$ is {acetylamino}($C_1$-$C_6$)alkyl.

(6) a compound of Formula I wherein $R^1$ or $R^3$ is amino ($C_1$-$C_6$)alkyl can be reacted with methanesulfonyl chloride to give a compound of Formula I wherein $R^1$ or $R^3$ is {methanesulfonylamino}($C_1$-$C_6$)alkyl.

(7) a compound of Formula I, wherein $R^1$ or $R^3$ is ($C_2$-$C_6$) alkenyl is hydroborated to afford a compound of Formula I wherein $R^1$ or $R^3$ is hydroxy($C_2$-$C_6$)alkyl. When the alkene is at the terminus of the ($C_2$-$C_6$)alkenyl group, the major product is generally the primary ω-hydroxy($C_2$-$C_6$)alkenyl i and the minor product is the secondary alcohol ii.

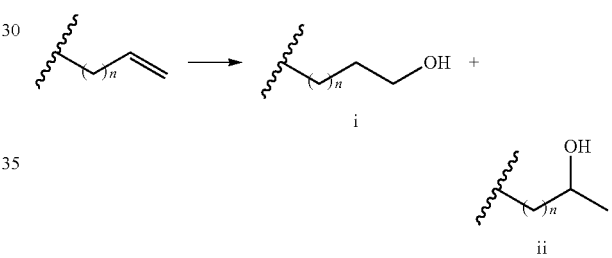

$n$ = 0-4

(8) a compound of Formula I, wherein $R^1$ is ($C_2$-$C_6$)alkenyl, can be reacted with osmium tetroxide and N-methylmorpholine-N-oxide to afford a compound of Formula I wherein $R^1$ is vicinal dihydroxy($C_2$-$C_6$)alkyl, (9) a compound of Formula I wherein $R^3$ is ($C_2$-$C_6$)alkenyl, can be reacted with osmium tetroxide and N-methylmorpholine-N-oxide to afford a vicinal diol compound of Formula I wherein $R^3$ is vicinal dihydroxy($C_2$-$C_6$)alkyl,

(10) a compound of Formula I, wherein $R^1$ is ($C_2$-$C_6$) alkenyl, can be reacted with ozone followed by $NaBH_4$ to give a compound of Formula I wherein $R^1$ is ω-hydroxy($C_1$-$C_5$) alkyl.

(11) a compound of Formula I, wherein $R^3$ is ($C_2$-$C_6$) alkenyl, can be reacted with ozone followed by $NaBH_4$ to give a compound of Formula I wherein $R^3$ is ω-hydroxy($C_1$-$C_5$) alkyl.

(12) a compound of Formula I wherein $R^1$ or $R^3$ is amino ($C_1$-$C_6$)alkyl can be reacted with an ($C_1$-$C_6$)alkyl isocyanate to give a compound of Formula I wherein $R^1$ or $R^3$ is ($C_1$-$C_6$) alkylaminocarbonylamino($C_1$-$C_6$)alkyl.

(13) a compound of Formula I wherein $R^1$ or $R^3$ is amino ($C_1$-$C_6$)alkyl can be reacted with an ($C_1$-$C_6$)alkyl chloroformate to give a compound of Formula I wherein $R^1$ or $R^3$ is ($C_1$-$C_6$)alkoxycarbonylamino($C_1$-$C_6$)alkyl.

(14) a compound of Formula I wherein $R^1$ or $R^3$ is amino $(C_1-C_6)$alkyl can be reacted with chlorosulfonyl isocyanate or sulfamide to give a compound of Formula I wherein $R^1$ or $R^3$ is aminosulfonylamino$(C_1-C_6)$alkyl.

(15) a compound of Formula I wherein $R^1$ or $R^3$ is amino $(C_1-C_6)$alkyl can be reacted with a $(C_1-C_6)$alkylsulfamoyl chloride to give a compound of Formula I wherein $R^1$ or $R^3$ is $(C_1-C_6)$alkylaminosulfonylamino$(C_1-C_6)$alkyl.

(16) a compound of Formula I wherein $R^1$ or $R^3$ is hydroxy $(C_1-C_6)$alkyl can be reacted with chlorosulfonyl isocyanate to give a compound of Formula I wherein $R^1$ or $R^3$ is aminosulfonyloxy$(C_1-C_6)$alkyl.

(17) a compound of Formula I wherein $R^1$ or $R^3$ is hydroxy $(C_1-C_6)$alkyl can be reacted with p-nitrophenyl chloroformate, pentafluorophenyl chloroformate or carbonyl diimidazole, followed by ammonia, a $(C_1-C_6)$alkylamine or a di$(C_1-C_6)$alkylamine to give a compound of Formula I wherein $R^1$ or $R^3$ is aminocarboxy$(C_1-C_6)$alkyl, $(C_1-C_6)$alkyl aminocarboxy$(C_1-C_6)$alkyl or di$(C_1-C_6)$alkylaminocarboxy$(C_1-C_6)$alkyl.

(18) a compound of Formula I wherein $R^1$ or $R^3$ is hydroxy $(C_1-C_6)$alkyl can be reacted with $POCl_3$ to give a compound of Formula I wherein $R^1$ or $R^3$ is $(HO)_2P(=O)O(C_1-C_6)$alkyl.

(19) a compound of Formula I wherein $Cy^1$ is substituted with bromine or iodine, $A^2$ is a bond and $Cy^2$ is hydrogen can be reacted with a cyclic amine in the presence of a palladium catalyst to give a compound of Formula I wherein $A^2$ is a bond and $Cy^2$ is a cyclic amino moiety attached through its nitrogen atom.

(20) a compound of Formula I wherein $R^3$ is $MeO_2C(C_1-C_6)$alkyl can be treated with MeMgBr to afford a compound of Formula I wherein $R^3$ is $Me_2(HO)C(C_1-C_6)$alkyl.

(21) a compound of Formula I wherein $R^1$ or $R^3$ is $\omega$-$H_2NCO(C_1-C_6)$alkyl can be reacted with TFAA in the presence of pyridine to afford a compound of Formula I wherein $R^1$ or $R^3$ is $\omega$-cyano$(C_1-C_6)$alkyl.

(22) a compound of Formula I wherein $R^3$ is amino$(C_1-C_6)$alkyl can be reacted with a 2-fluoropyridine to give a compound of Formula I wherein $R^3$ is 2-pyridylamino$(C_1-C_6)$alkyl.

(23) a compound of Formula I wherein $R^3$ is $\omega$-hydroxy $(C_1-C_6)$alkyl can be converted to its methanesulfonate or trifluoromethanesulfonate, treated with a $(C_1-C_6)$alkylthiol followed by oxidation with m-CPBA to give a compound of Formula I wherein $R^3$ is $(C_1-C_6)$alkylsulfonyl$(C_1-C_6)$alkyl.

(24) a compound of Formula I wherein $Cy^1$ is aryl or heteroaryl substituted with bromine or iodine, $A^2$ is a bond and $Cy^2$ is hydrogen can be reacted with bis(pinacolato)diboron in the presence of a palladium catalyst to give a boronate ester which can be further reacted with (a) an aryl, heteroaryl or heterocyclyl halide again in the presence of a palladium catalyst to give a compound of Formula I wherein $A^2$ is a bond and $Cy^2$ is aryl, heteroaryl or heterocyclyl.

(25) a compound of Formula I, wherein $R^3$ is allyl or homoallyl can be reacted with oxygen in the presence of $PdCl_2$ and CuCl to afford a compound of Formula I, wherein $R^3$ is 2-oxopropyl or 3-oxobutyl respectively.

(26) a compound of Formula I, wherein $R^3$ is 2-oxopropyl or 3-oxobutyl can be reacted with MeMgX, wherein X is Cl, Br or I, to give a compound of Formula I, wherein $R^3$ is 2-hydroxy-2-methylpropyl or 3-hydroxy-3-methylpropyl respectively.

(27) a compound of Formula I, wherein $R^3$ is $-CH_2CO_2Me$ can be treated with MeMgX, wherein X is Cl, Br or I, to give a compound of Formula I, wherein $R^3$ is 2-hydroxy-2-methylpropyl.

(28) a compound of Formula I, wherein $R^3$ is allyl or $-CH_2C(Me)=CH_2$ can be hydrocyanated with TsCN in the presence of triphenylsilane and various cobalt catalysts to afford compounds of Formula I, wherein $R^3$ is $-CH_2CH(CN)Me$ or $-CH_2CMe_2CN$ respectively.

(29) a compound of Formula I, wherein $R^3$ is $CH_2C(Me)_2CN$, can be treated with acetamide in the presence of $PdCl_2$ to give a compound of Formula I, wherein $R^3$ is $CH_2CMe_2CONH_2$.

(30) a compound of Formula I, wherein $R^3$ is $-CH_2C(Me)=CH_2$ can be treated with m-CPBA followed by lithium triethylborohydride to afford a compound of Formula I, wherein $R^3$ is 2-hydroxy-2-methylpropyl.

In an eleventh process a compound of Formula I can be prepared from a compound of Formula XLVII, wherein $R^a$ is a lower alkyl group such as methyl or ethyl and $R^b$ is a leaving group such as chloride, bromide, alkanesulfonate, arylsulfonate or haloalkanesulfonate, and an amine of Formula IV

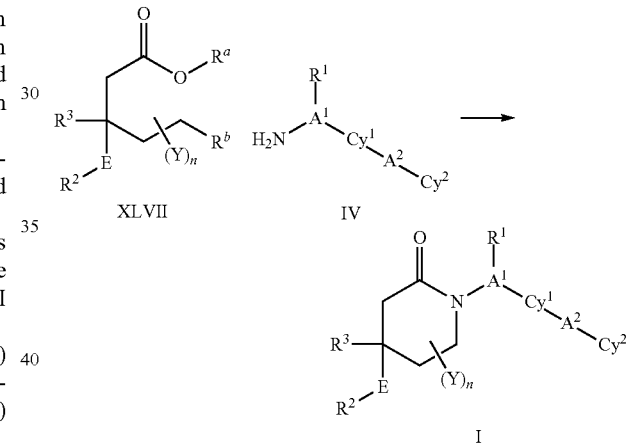

Intermediates of Formula XLVII, wherein $R^b$ is chloro, n is 0 and $R^3$ is allyl, can be prepared from alcohols of Formula XLVIII by treatment with allyltrimethylsilane in the presence of $TiCl_4$.

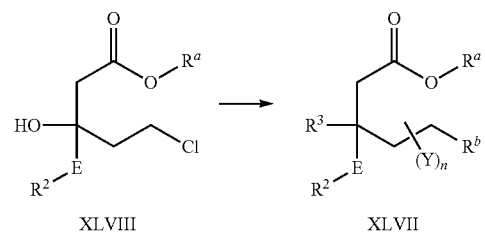

Alcohols of Formula XLVIII can be prepared by Reformatsky reaction of alkyl bromoacetates of Formula L with β-chloroketones of Formula XLIX.

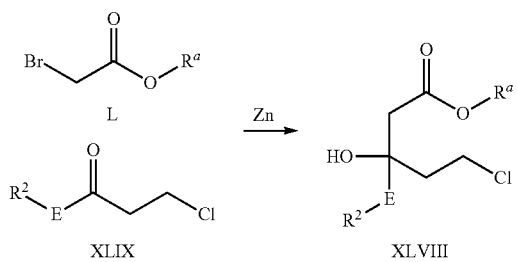

In a twelfth process a compound of Formula I can be prepared from an aminoester of Formula LI by heating,

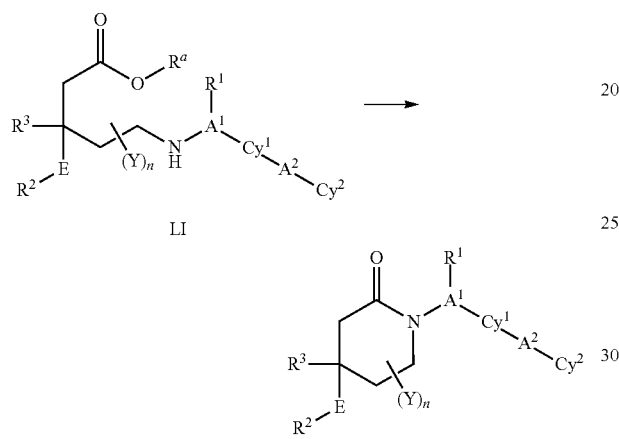

Aminoesters of Formula LI, wherein $R^3$ is allyl can be prepared from optionally N-protected aminoalcohols of Formula LII by treatment with allytrimethylsilane in the presence of $TiCl_4$.

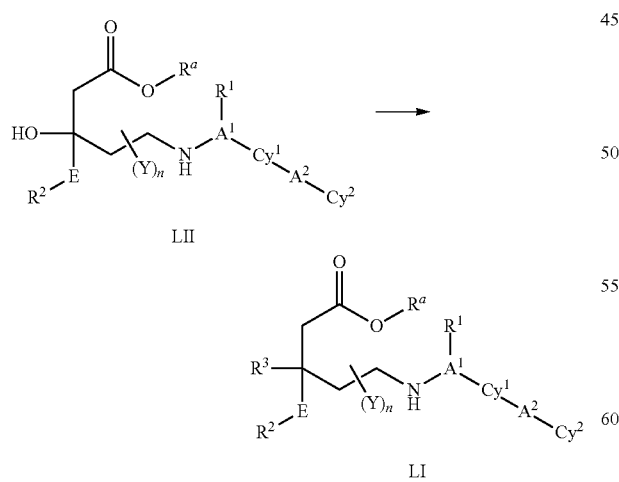

Optionally N-protected aminoalcohols of Formula LII can by Reformatsky reaction of alkyl bromoacetates of Formula L with optionally N-protected aminoalcohols of Formula LIII.

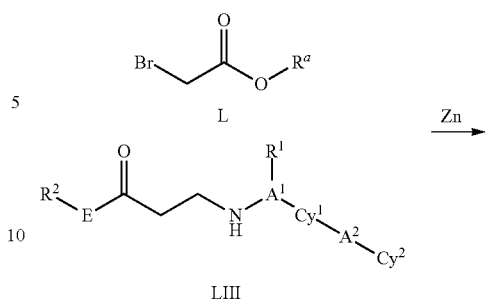

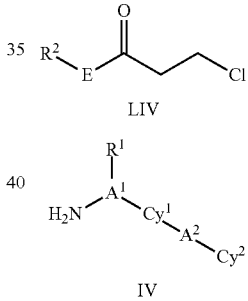

Optionally N-protected aminoalcohols of Formula LIII can be prepared by reaction of optionally N-protected amines of Formula IV with β-chloroketones of Formula LIV.

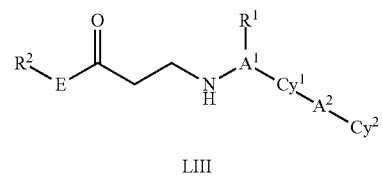

Purification Methods

Compounds of the invention can be purified by high pressure liquid chromatography (prep HPLC). Unless otherwise specified, prep HPLC refers to preparative reverse phase HPLC on a C-18 column eluted with a water/acetonitrile gradient containing 0.01% TFA run on a Gilson 215 system.

LC-MS Methods

Method 1 (30-90)

| Column | YMC-PACK ODS-AQ, 50 × 2.0 mm 5 μm | | |
|---|---|---|---|
| Mobile Phase | A: water (4 L) + TFA (1.5 mL)) B: acetonitrile (4 L) + TFA (0.75 mL)) | | |
| | TIME (min) | A % | B % |
| | 0 | 70 | 30 |
| | 2.2 | 10 | 90 |
| | 2.5 | 10 | 90 |
| Flow Rate | 1 mL/min | | |
| Wavelength | UV220 | | |
| Oven Temp | 50° C. | | |
| MS ionization | ESI | | |

Method 2 (10-80)

| Column | YMC-PACK ODS-AQ, 50 × 2.0 mm 5 μm | | |
|---|---|---|---|
| Mobile Phase | A: water (4 L) + TFA (1.5 mL)) B: acetonitrile (4 L) + TFA (0.75 mL)) | | |
| | TIME (min) | A % | B % |
| | 0 | 90 | 10 |
| | 2.2 | 20 | 80 |
| | 2.5 | 20 | 80 |
| Flow Rate | 1 mL/min | | |
| Wavelength | UV 220 nm | | |
| Oven Temp | 50° C. | | |
| MS ionization | ESI | | |

Method 3 (3 min)

Column: Chromolith SpeedRod, RP-18e, 50×4.6 mm; Mobil phase: A: 0.01% TFA/water, B: 0.01% TFA/CH$_3$CN; Flow rate: 1 mL/min; Gradient:

| Time (min) | A % | B % |
|---|---|---|
| 0.0 | 90 | 10 |
| 2.0 | 10 | 90 |
| 2.4 | 10 | 90 |
| 2.5 | 90 | 10 |
| 3.0 | 90 | 10 |

EXAMPLE 1

4-allyl-1-((1S)-1-(4-bromophenyl)ethyl)-4-phenylpiperidin-2-one

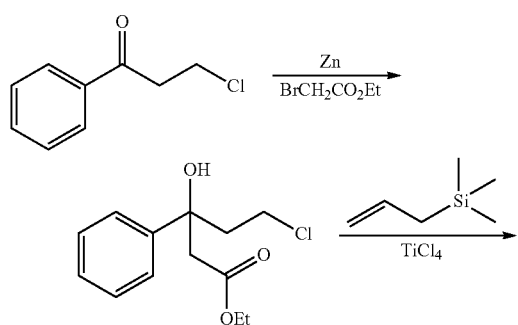

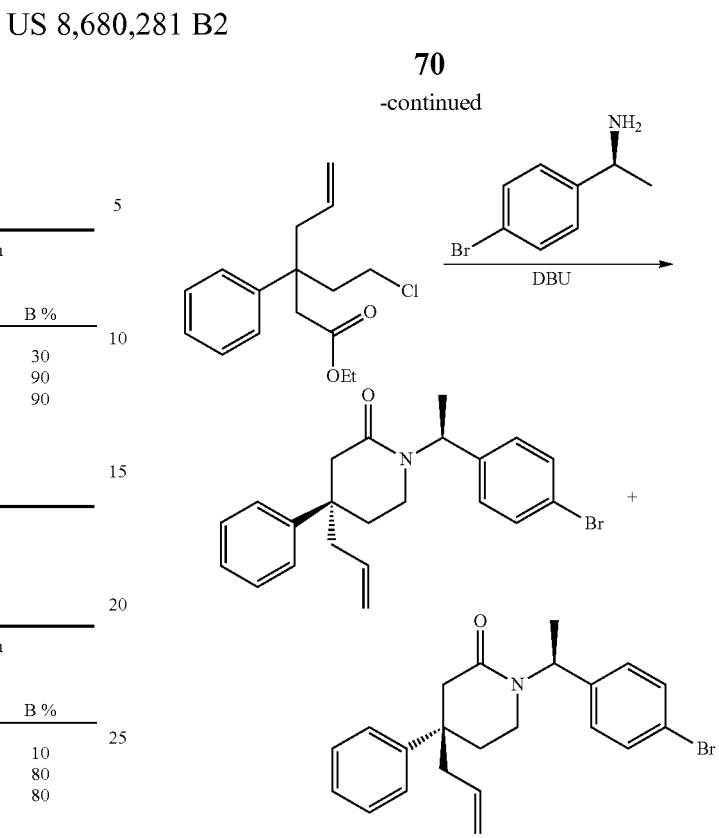

Step 1

To a stirred suspension of 3-chloro-1-phenylpropan-1-one (10 g, 0.059 mol) and active Zinc power (19 g, 0.295 mol) in THF (200 mL) was added iodine (9 g, 0.035 mol), then ethyl bromoacetate (20 g, 0.118 mol) was added dropwise at rt. The formed mixture was heated to reflux for 30 min. The reaction was quenched with water, and the mixture was filtered through a celite pad. The filtrate was extracted with EtOAc. The organic phase was dried over Na$_2$SO$_4$, and concentrated to give the crude product, which was purified by column chromatography to afford ethyl 5-chloro-3-hydroxy-3-phenylpentanoate (8.0 g, 53%). $^1$H NMR (CDCl$_3$): δ=1.02 (t, 3H), 2.13-2.28 (m, 2H), 2.73 (d, 1H), 2.90 (d, 1H), 3.11 (1, 2H), 3.54 (m, 1H), 3.94 (q, 2H), 7.18 (m, 1H), 7.29 (m, 4H).

Step 2

To a solution of ethyl 5-chloro-3-hydroxy-3-phenylpentanoate (1.0 g, 3.9 mmol) in anhydrous CH$_2$Cl$_2$ (20 mL) cooled to −78° C. under nitrogen was added allyltrimethylsilane (4.5 g, 39 mmol) followed by a solution of TiCl$_4$ in CH$_2$Cl$_2$ (16 mL, 1 mol/L) dropwise. The solution was stirred at −78° C. for 30 min, and then was heated to reflux overnight. The reaction was quenched with aqueous Na$_2$CO$_3$ solution. The organic phase was separated and concentrated to give the crude product, which was purified by column chromatography to afford the ethyl 3-(2-chloroethyl)-3-phenylhex-5-enoate (0.5 g, 45%). $^1$H NMR (CDCl$_3$): δ=1.08 (t, 3H), 2.24 (m, 2H), 2.54 (m, 2H), 2.68 (d, 2H), 3.19 (m, 1H), 3.26 (m, 1H), 3.96 (q, 2H), 5.01 (m, 2H), 5.51 (m, 1H), 7.14 (m, 1H), 7.19 (m, 2H), 7.29 (m, 2H).

Step 3

A mixture of ethyl 3-(2-chloroethyl)-3-phenylhex-5-enoate (200 mg, 0.712 mmol), (S)-1-(4-bromophenyl)ethanamine (160 mg, 0.784 mmol), and DBU (220 mg, 1.45 mmol) in CH$_3$CN (3 mL) was heated to reflux for 72 h. The mixture was washed with 1N aq HCl, and the organic phase was concentrated to give the crude product, which was purified by TLC to give two isomers.

Isomer 1: (S)-4-allyl-1-(S)-1-(4-bromophenyl)ethyl)-4-phenylpiperidin-2-one (20 mg, 7%) ¹H NMR (CDCl₃): δ=1.38 (d, 3H), 1.89 (m, 1H), 2.04 (m, 1H), 2.23 (m, 2H), 2.40 (m, 2H), 2.92 (m, 2H), 4.90 (m, 2H), 5.36 (m, 1H), 5.92 (m, 1H), 6.68 (d, 2H), 7.18 (m, 5H), 7.24 (m, 2H).

Isomer 2: (R)-4-allyl-1-((S)-1-(4-bromophenyl)ethyl)-4-phenylpiperidin-2-one (20 mg, 7%). ¹H NMR (CDCl₃): δ=1.12 (d, 3H), 1.78 (m, 1H), 1.98 (m, 1H), 2.22 (m, 1H), 2.43 (m, 2H), 2.56 (m, 2H), 2.90 (dd, 1H), 4.88 (m, 2H), 5.33 (m, 1H), 5.92 (m, 1H), 7.02 (d, 2H), 7.18 (m, 2H), 7.26 (m, 2H), 7.34 (d, 2H).

EXAMPLE 2

1-((1S)-1-(4-bromophenyl)ethyl)-4-(2-hydroxyethyl)-4-phenylpiperidin-2-one

Isomer 1

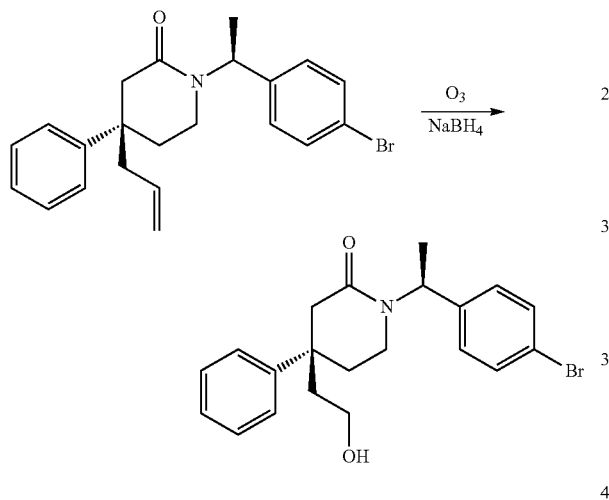

A solution of (S)-4-allyl-1-((S)-1-(4-bromophenyl)ethyl)-4-phenylpiperidin-2-one (20 mg, 0.05 mmol) in methylene chloride (20 mL) was cooled to −78° C. and ozone was bubbled in until a blue color appeared. Then NaBH₄ (20 mg, 0.5 mmol) was added to the above solution at 0° C., and the mixture was stirred overnight. The reaction was quenched with water. The organic phase was separated, and concentrated to give the crude product which was purified by preparative TLC to afford (R)-1-((S)-1-(4-bromophenyl)ethyl)-4-(2-hydroxyethyl)-4-phenylpiperidin-2-one (2 mg, 10%). ¹H NMR: (400 MHz, CDCl₃): δ=1.38 (d, 3H), 1.81 (m, 1H), 1.96 (m, 2H), 2.06 (m, 1H), 2.23 (m, 2H), 2.50 (m, 2H), 2.91 (m, 1H), 3.08 (m, 1H), 3.31 (m, 1H), 3.49 (m, 1H), 5.91 (m, 1H), 6.69 (m, 2H), 7.16 (m, 5H), 7.26 (m, 3H).

Isomer 2

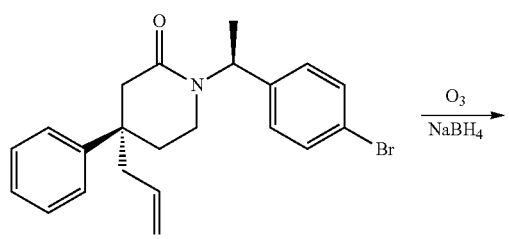

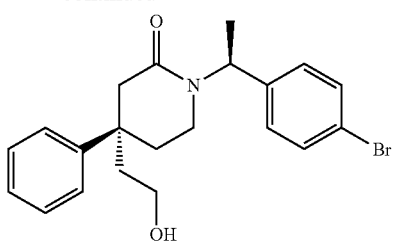

Application of the procedure described above to (R)-4-allyl-1-((S)-1-(4-bromophenyl)ethyl)-4-phenylpiperidin-2-one (20 mg, 0.05 mmol) afforded (S)-1-((S)-1-(4-bromophenyl)ethyl)-4-(2-hydroxyethyl)-4-phenylpiperidin-2-one (2.2 mg, 11%). ¹H NMR: (400 MHz, CDCl₃): δ=1.11 (d, 3H), 1.79 (m, 2H), 2.03 (m, 2H), 2.52 (m, 3H), 3.08 (dd, 1H), 3.29 (m, 1H), 3.46 (m, 1H), 5.96 (m, 1H), 7.02 (d, 1H), 7.19 (m, 2H), 7.28 (m, 2H), 7.34 (m, 2H).

EXAMPLE 3

1-((S)-1-(4'-fluorobiphenyl-4-yl)ethyl)-4-(2-hydroxyethyl)-4-phenylpiperidin-2-one

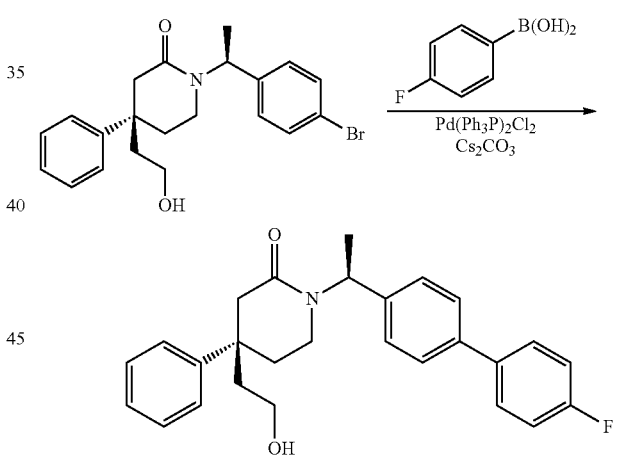

Isomer 1:

A mixture of (R)-1-((S)-1-(4-bromophenyl)ethyl)-4-(2-hydroxyethyl)-4-phenyl piperidin-2-one (30 mg, 0.072 mmol), 4-fluorophenylboronic acid (15 mg, 0.11 mmol), Pd(Ph₃P)₂Cl₂ (5 mg), and aqueous Cs₂CO₃ (0.1 mL, 2M) in 1,4-dioxane (2 mL) was stirred and heated at reflux for 2 h. The organic phase was separated, and concentrated to give the crude product, which was purified by preparative TLC to give (R)-1-((S)-1-(4'-fluorobiphenyl-4-yl)ethyl)-4-(2-hydroxyethyl)-4-phenylpiperidin-2-one (3.0 mg, 10%). LC-MS Method 2, t_R=2.103 min, m/z=440.1. ¹H NMR (CDCl₃): δ 1.46 (d, 3H), 1.83 (m, 1H), 2.01 (m, 3H), 2.32 (m, 1H), 2.59 (dd, 1H), 2.96 (m, 1H), 3.11 (dd, 1H), 3.34 (m, 1H), 3.49 (m, 1H), 6.02 (q, 1H), 6.89 (m, 2H), 7.06 (m, 2H), 7.22 (m, 2H), 7.31 (m, 4H), 7.40 (m, 2H).

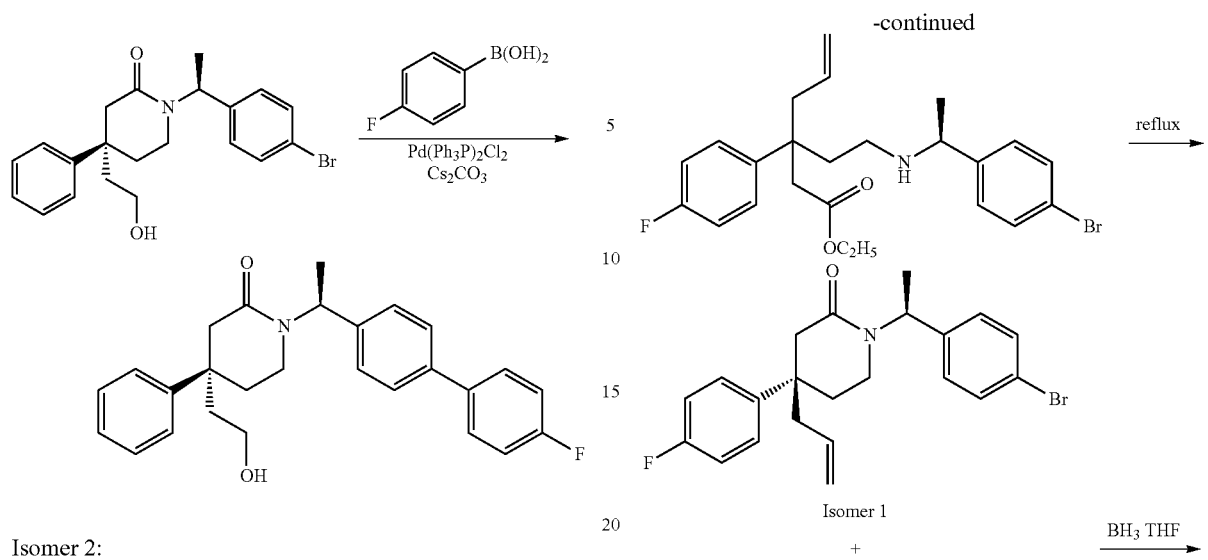

Isomer 2:

A mixture of (S)-1-((S)-1-(4-bromophenyl)ethyl)-4-(2-hydroxyethyl)-4-phenyl piperidin-2-one (25 mg, 0.062 mmol), 4-fluorophenylboronic acid (15 mg, 0.093 mmol), Pd(Ph$_3$P)$_2$Cl$_2$ (5 mg), and aqueous Cs$_2$CO$_3$ (0.1 mL, 2M) in 1,4-dioxane (2 mL) was stirred and heated at reflux for 2 hours. The organic phase was separated, and concentrated to give the crude product, which was purified by preparative TLC to give (S)-1-((S)-1-(4'-fluorobiphenyl-4-yl)ethyl)-4-(2-hydroxyethyl)-4-phenylpiperidin-2-one (3.0 mg, 12%). LC-MS Method 2, t$_R$=2.167 min, m/z=440.1. $^1$H NMR (CDCl$_3$): δ 1.18 (d, 3H), 1.86 (m, 2H), 2.06 (m, 2H), 2.54 (m, 2H), 2.64 (m, 1H), 3.10 (dd, 1H), 3.31 (m, 1H), 3.46 (m, 1H), 6.04 (q, 1H), 7.02 (m, 2H), 7.20 (m, 4H), 7.32 (m, 2H), 7.46 (m, 4H).

EXAMPLE 4

3-(1-((S)-1-(4-bromophenyl)ethyl)-4-(4-fluorophenyl)-2-oxopiperidin-4-yl)propanamide Isomer 1

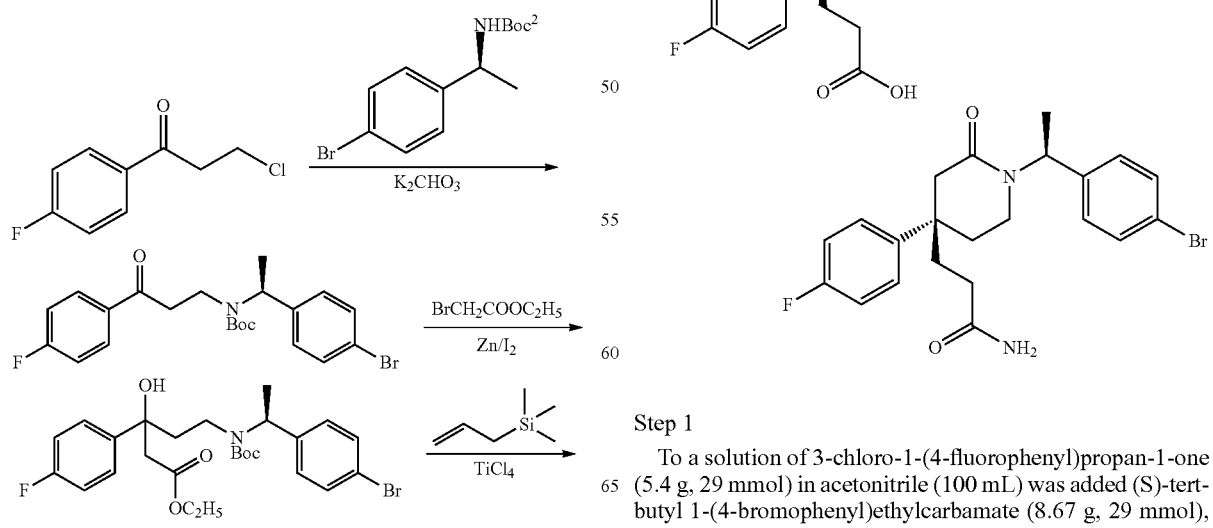

Step 1

To a solution of 3-chloro-1-(4-fluorophenyl)propan-1-one (5.4 g, 29 mmol) in acetonitrile (100 mL) was added (S)-tert-butyl 1-(4-bromophenyl)ethylcarbamate (8.67 g, 29 mmol), K$_2$CO$_3$ (12.4 g, 90 mmol) and KI (14.9 g, 90 mmol). The mixture was refluxed overnight. The reaction mixture was filtered through a celite pad, and the filtrate was concentrated to give the crude (S)-tert-butyl 1-(4-bromophenyl)ethyl (3-(4-fluorophenyl)-3-oxopropyl)carbamate (13 g), which was used to the next step without purification.

Step 2

To a stirred suspension of (S)-tert-butyl 1-(4-bromophenyl)ethyl(3-(4-fluorophenyl)-3-oxopropyl)carbamate (13 g, 28.9 mmol) and zinc powder (9.4 g, 0.144 mol) in THF (200 mL) at rt was added iodine (4.40 g, 0.173 mol) and ethyl bromoacetate (9.7 g, 57.7 mmol). The mixture was heated at reflux for 2 h, and quenched by addition of water. The mixture was filtered through a celite pad, the filtrate was extracted with EtOAc. The organic phase was concentrated to give the crude product, which was purified by column chromatography to afford ethyl 5-(((S)-1-(4-bromophenyl)ethyl)(tert-butoxycarbonyl)amino)-3-(4-fluorophenyl)-3-hydroxypentanoate (4.8 g, 31%). $^1$H NMR (CDCl$_3$): δ 1.02 (t, 3H), 1.29-1.41 (m, 12H), 1.88 (m, 1H), 2.51-2.73 (m, 3H), 2.99 (m, 1H), 3.96 (q, 2H), 4.03 (m, 1H), 4.36 (m, 1H), 4.77 (m, 1H), 5.33 (m, 1H), 6.88-6.96 (m, 4H), 7.11 (m, 2H), 7.24 (m, 1H), 7.36 (m, 3H).

Step 3

To a solution of ethyl 5-(tert-butoxycarbonyl((S)-1-(4-fluorophenyl)ethyl)amino)-3-(4-fluorophenyl)-3-hydroxypentanoate (2.0 g, 3.72 mmol) in anhydrous CH$_2$Cl$_2$ (40 mL) -78° C. under nitrogen was added allyltrimethylsilane (4.40 g, 37.2 mmol) and a solution of TiCl$_4$ in CH$_2$Cl$_2$ (19 mL, 1 M). The solution was stirred at −78° C. for 30 min, warmed to rt, and heated at reflux overnight. The reaction was quenched with aqueous Na$_2$CO$_3$ solution, and the organic phase was separated and concentrated to give the crude product, which was purified by column chromatography to afford ethyl 3-(2-((S)-1-(4-bromophenyl)ethylamino)ethyl)-3-(4-fluorophenyl)hex-5-enoate (500 mg, 29%). $^1$H NMR (CDCl$_3$): δ 0.99 (t, 3H), 1.99 (m, 2H), 2.24 (m, 2H), 2.39 (m, 1H), 2.46 (m, 1H), 2.53 (m, 2H), 3.62 (m, 1H), 3.89 (q, 2H), 4.93 (m, 2H), 5.46 (m, 1H), 6.89 (m, 2H), 7.19 (m, 4H), 7.41 (m, 2H).

Step 4

A mixture of ethyl 3-(2-((S)-1-(4-bromophenyl)ethylamino)ethyl)-3-(4-fluorophenyl)hex-5-enoate (500 mg, 1.08 mmol) and ethanol (20 mL) was heated at reflux overnight. The mixture was concentrated to give the crude product, which was purified by preparative TLC to give the two diastereomeric products.

Isomer 1: (S)-4-allyl-1-((S)-1-(4-bromophenyl)ethyl)-4-(4-fluorophenyl)piperidin-2-one (150 mg, 33%). $^1$H NMR (CDCl$_3$): δ 1.41 (t, 3H), 1.91-2.09 (m, 2H), 2.26 (m, 2H), 2.39 (m, 1H), 2.52 (m, 1H), 2.99 (m, 2H), 3.49 (m, 1H), 4.96 (m, 2H), 5.46 (m, 1H), 5.94 (m, 2H), 6.76 (m, 2H), 6.98 (m, 2H), 7.14 (m, 2H), 7.22 (m, 2H).

Isomer 2: (R)-4-allyl-1-((S)-1-(4-bromophenyl)ethyl)-4-(4-fluorophenyl)piperidin-2-one (170 mg, 38%). $^1$H NMR (CDCl$_3$): δ1.21 (t, 3H), 1.79 (m, 1H), 2.01 (m, 1H), 2.26 (m, 1H), 2.41 (m, 1H), 2.51 (m, 1H), 2.62 (m, 2H), 2.91 (d, 2H), 4.92 (m, 2H), 5.39 (m, 1H), 6.01 (q, 1H), 6.99 (m, 2H), 7.14 (m, 2H), 7.26 (m, 2H), 7.42 (m, 2H);

Step 5

To a solution of (S)-4-allyl-1-((S)-1-(4-bromophenyl)ethyl)-4-(4-fluorophenyl)piperidin-2-one (70 mg, 0.169 mmol) in THF (5 mL) was added BH$_3$/THF (0.6 mL, 1 M) at 0° C. under nitrogen atmosphere. The mixture was stirred for 2 h, and the reaction was quenched with water. Aqueous NaOH solution (1 M, 2 mL) and H$_2$O$_2$ (1 mL 30%) were added to the above mixture, and the resulting mixture was stirred for 1 h. The mixture was extracted with EtOAc, and the combined organic phase was concentrated to give the crude product, which was purified by preparative HPLC to give (S)-1-((S)-1-(4-bromophenyl)ethyl)-4-(4-fluorophenyl)-4-(3-hydroxypropyl)piperidin-2-one (30 mg, 41%). $^1$H NMR (CDCl$_3$): δ 1.36 (m, 1H), 1.52 (m, 1H), 1.72 (m, 2H), 1.89 (m, 1H), 1.98 (m, 1H), 2.21 (m, 1H), 2.44 (m, 1H), 2.92 (m, 1H), 3.01 (m, 1H), 3.44 (m, 2H), 5.92 (m, 2H), 6.73 (m, 2H), 6.91 (m, 2H), 7.14 (m, 4H).

Step 6

To a solution of (S)-1-((S)-1-(4-bromophenyl)ethyl)-4-(4-fluorophenyl)-4-(3-hydroxypropyl)piperidin-2-one (30 mg, 0.069 mmol) in acetone (2 mL) was added Jones reagent (0.3 mL, 2.5 M) at 0° C. The mixture was stirred for 0.5 h, diluted with EtOAc, and washed with water. The organic phase was concentrated to give the crude 3-((S)-1-((S)-1-(4-bromophenyl)ethyl)-4-(4-fluorophenyl)-2-oxopiperidin-4-yl)propanoic acid (28 mg, 90%), which was used for the next step without further purification.

Step 7

The solution of 3-((S)-1-((S)-1-(4-bromophenyl)ethyl)-4-(4-fluorophenyl)-2-oxopiperidin-4-yl)propanoic acid (28 mg, 0.063 mmol), EDCI (38 mg, 0.189 mmol), HOBt (26 mg, 0.189 mmol), and DIEA (82 mg, 0.63 mmol) in CH$_2$Cl$_2$ was filled with NH$_3$ at 0° C. The mixture was stirred overnight, and washed with water. The organic phase was separated and concentrated to give the crude product, which was purified by preparative HPLC to afford 3-((S)-1-((S)-1-(4-bromophenyl)ethyl)-4-(4-fluorophenyl)-2-oxopiperidin-4-yl)propanamide (6 mg, 21%). LC-MS Method 2, t$_R$=1.869 min, m/z=447. $^1$H NMR (CDCl$_3$): δ 1.46 (d, 3H), 1.77 (m, 1H), 1.92 (m, 1H), 1.96 (m, 1H), 2.08 (m, 1H), 2.14 (m, 3H), 2.24 (m, 1H), 2.51 (d, 1H), 3.02 (m, 1H), 3.12 (m, 1H), 5.32 (m, 1H), 5.71 (m, 1H), 5.94 (q, 1H), 6.76 (m, 2H), 6.99 (m, 2H), 7.16 (m, 2H), 7.24 (m, 2H).

Isomer 2

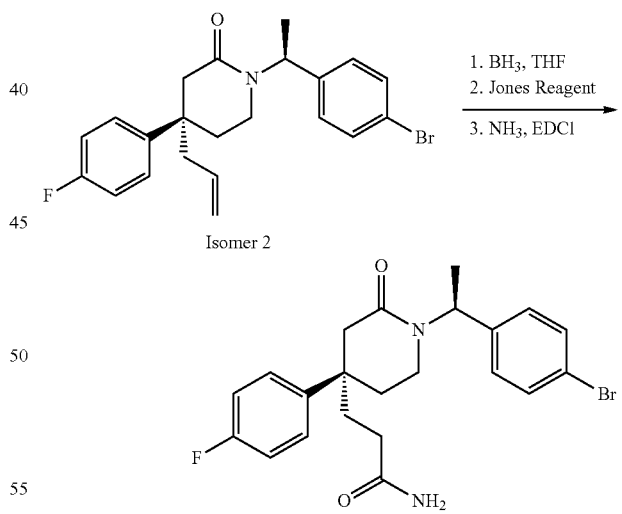

3-((R)-1-((S)-1-(4-bromophenyl)ethyl)-4-(4-fluorophenyl)-2-oxopiperidin-4-yl)propanamide was prepared from (R)-4-allyl-1-((S)-1-(4-bromophenyl)ethyl)-4-(4-fluorophenyl)piperidin-2-one following procedures analogous to those described in Steps 5-7 immediately above. LC-MS Method 2, t$_R$=1.922 min, m/z=448.7. 1H NMR (CDCl3) δ 1.24 (d, 3H), 1.71-1.84 (m, 3H), 1.99 (m, 2H), 2.14 (m, 1H), 2.46 (m, 1H), 2.52 (m, 1H), 2.67 (m, 1H), 3.11 (d, 2H), 5.44 (br, 1H), 5.89 (q, 1H), 6.11 (m, 1H), 7.01 (m, 4H), 7.14 (m, 2H), 7.39 (m, 2H).

EXAMPLE 5

5-(4-((1S)-1-(4-(4-fluorophenyl)-4-(3-hydroxypropyl)-2-oxopiperidin-1-yl)ethyl)phenyl)-1-methylpyridin-2(1H)-one Isomer 1

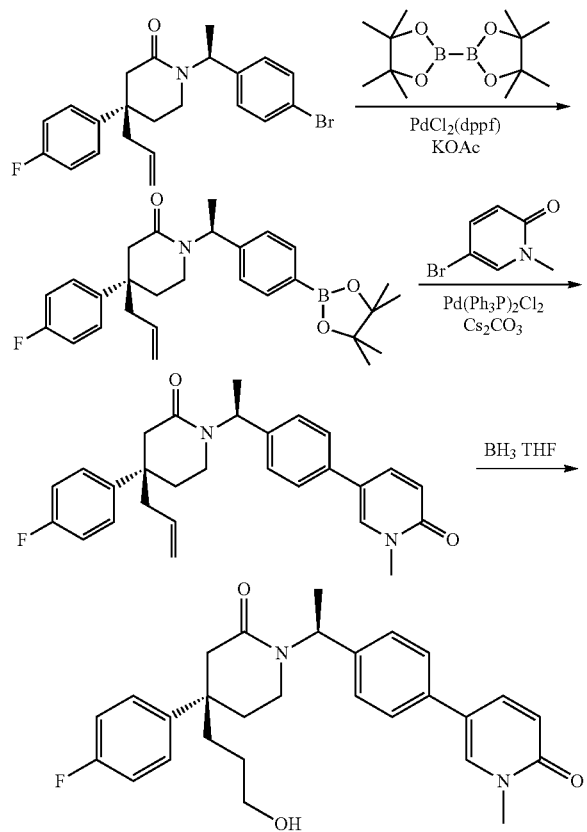

Step 1

A mixture of (S)-4-allyl-1-((S)-1-(4-bromophenyl)ethyl)-4-(4-fluorophenyl)piperidin-2-one (170 mg, 0.410 mmol), 4,4,4',4',5,5,5',5'-octamethyl-2,2'-bi(1,3,2-dioxaborolane) (138 mg, 0.54 mmol), PdCl$_2$dppf (12 mg, 0.014 mmol KOAc (141 mg, 1.435 mmol) in DMSO (2 mL) was heated at 90° C. for 20 h. The mixture was diluted with EtOAc, and washed with water. The organic phase was separated, and concentrated to give the crude product, which was purified by TLC to afford (S)-4-allyl-4-(4-fluorophenyl)-1-((S)-1-(4-(4,4,5,5-tetramethyl-1,3,2-dioxaborolan-2-yl)phenyl)ethyl)piperidin-2-one (120 mg, 63%). $^1$H NMR (CDCl$_3$): δ 1.29 (s, 12H), 1.48 (d, 3H), 1.96 (m, 2H), 2.26 (m, 3H), 2.43 (m, 2H), 2.52 (d, 1H), 2.92 (m, 2H), 4.93 (m, 2H), 5.42 (m, 1H), 6.04 (q, 1H), 6.92 (m, 4H), 7.12 (m, 2H) □ 7.59 (m, 2H).

Step 2

A mixture of (S)-4-allyl-4-(4-fluorophenyl)-1-((S)-1-(4-(4,4,5,5-tetramethyl-1,3,2-dioxaborolan-2-yl)phenyl)ethyl)piperidin-2-one (120 mg, 0.260 mmol), 5-bromo-1-methylpyridin-2(1H)-one (80 mg, 0.31 mmol), PdCl$_2$(Ph$_3$P)$_2$ (12 mg) □ Cs$_2$CO$_3$ (0.4 mL, 0.8 mmol □ in 1,4-dioxane (3 mL) was heated to reflux for 2 h. The mixture was diluted with EtOAc, and washed with water. The organic phase was separated, and concentrated to give the product, which was purified by TLC to afford 5-(4-((S)-1-((S)-4-allyl-4-(4-fluorophenyl)-2-oxopiperidin-1-yl)ethyl)phenyl)-1-methylpyridin-2(1H)-one (45 mg, 39%). $^1$H NMR (CDCl$_3$): δ 1.42 (t, 3H), 1.91 (m, 1H), 2.03 (m, 1H), 2.24 (m, 2H), 2.39 (m, 1H), 2.49 (d, 1H), 2.96 (m, 2H), 3.49 (s, 3H), 4.92 (m, 2H), 5.38 (m, 1H), 5.99 (m, 1H), 6.11 (m, 1H) □ 6.52 (m, 1H) □ 6.62 (m, 1H), 6.89 (m, 4H), 7.11 (m, 3H), 7.23 (m, 2H), 7.32 (m, 1H), 7.49 (m, 1H).

Step 3

To a solution of 5-(4-((S)-1-((S)-4-allyl-4-(4-fluorophenyl)-2-oxopiperidin-1-yl)ethyl)phenyl)-1-methylpyridin-2(1H)-one (45 mg, 0.10 mmol) in THF (3 mL) was added BH$_3$/THF (0.3 mL, 1 M) at 0° C. under nitrogen atmosphere. The mixture was stirred for 2 h. The reaction was quenched with water. Aqueous NaOH solution (1 M, 0.6 mL) and H$_2$O$_2$ (0.3 mL □ 30%) were added to the above mixture. The resulting mixture was stirred for 1 h. The mixture was extracted with EtOAc and the combined organic phase was concentrated to give the crude product, which was purified by preparative HPLC to give 5-(4-((S)-1-((S)-4-(4-fluorophenyl)-4-(3-hydroxypropyl)-2-oxopiperidin-1-yl)ethyl)phenyl)-1-methylpyridin-2(1H)-one (1.0 mg, 2%). LC-MS Method 2, t$_R$=1.63 min, m/z=463.1. $^1$H NMR (CDCl$_3$): δ1.42 (t, 3H), 1.69 (m, 2H), 1.92 (m, 1H), 2.01 (m, 1H), 2.22 (m, 2H), 2.44 (d, 2H), 2.99 (m, 3H), 3.36 (m, 1H), 3.42 (t, 2H), 3.59 (s, 3H), 3.60 (m, 1H), 3.84 (m, 1H), 6.01 (q, 1H), 6.61 (d, 1H) □ 6.89 (m, 4H), 7.14 (m, 4H), 7.33 (d, 1H), 7.49 (m, 1H).

Isomer 2

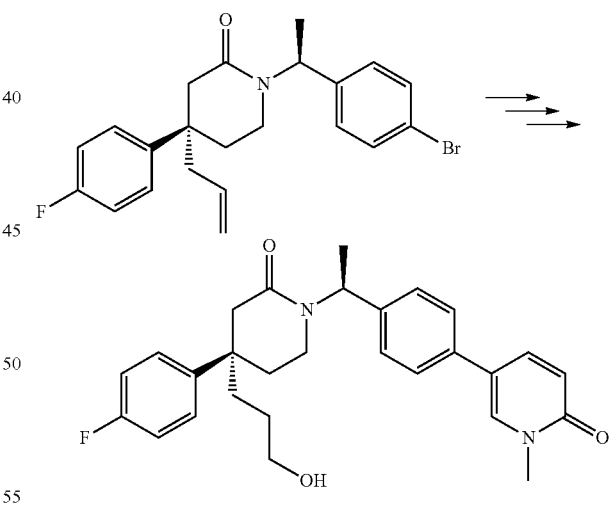

5-(4-((S)-1-((R)-4-(4-fluorophenyl)-4-(3-hydroxypropyl)-2-oxopiperidin-1-yl)ethyl)phenyl)-1-methylpyridin-2(1H)-one was prepared from (R)-4-allyl-1-((S)-1-(4-bromophenyl)ethyl)-4-(4-fluorophenyl)piperidin-2-one following procedures analogous to those described in Steps 1-3 immediately above. LC-MS Method 2, t$_R$=1.725 min, m/z=463.1. 1H NMR (CDCl3) δ 1.12 (d, 3H), 1.76 (m, 2H), 1.92 (m, 3H), 2.51 (d, 1H), 2.61 (m, 3H), 3.04 (d, 1H), 3.36 (m, 2H), 3.4236 (m, 2H), 3.61 (s, 3H), 3.89 (m, 1H), 5.93 (q, 1H), 6.73 (m, 1H), 6.98 (m, 3H), 7.16 (m, 3H), 7.21 (m, 2H), 7.31 (m, 2H), 7.51 (d, 1H), 7.68 (m, 1H)

EXAMPLE 6

1-((S)-1-(4-bromophenyl)propyl)-4-(2-hydroxy-2-methylpropyl)-4-phenylpiperidin-2-one

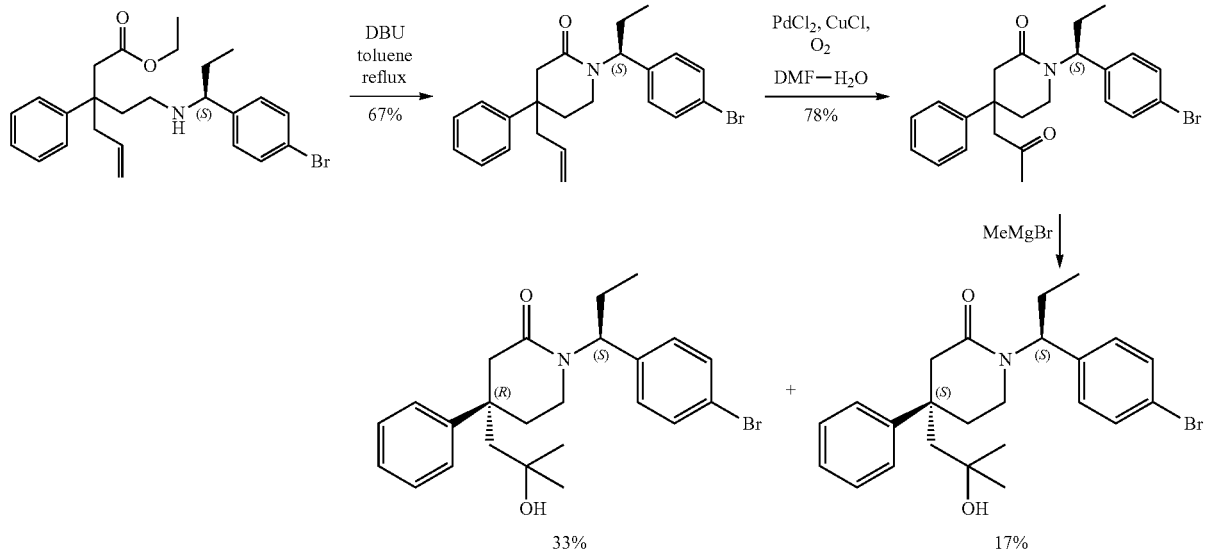

Step 1. 4-allyl-1-((S)-1-(4-bromophenyl)propyl)-4-phenylpiperidin-2-one

A mixture of ethyl 3-(2-((S)-1-(4-bromophenyl)propylamino)ethyl)-3-phenylhex-5-enoate (0.5028 g, 1.10 mmol) and DBU (1.30 g, 8.54 mmol) in toluene (10 mL) was heated to reflux under nitrogen for 2 d. The reaction mixture was cooled to rt, quenched with 2 N aq HCl, extracted with EtOAc, and dried over $Na_2SO_4$. After the solvents were evaporated, the residue was purified by chromatography on silica gel eluted with hexanes/EtOAc to afford 0.3045 g (67%) of 4-allyl-1-((S)-1-(4-bromophenyl)propyl)-4-phenylpiperidin-2-one. LC-MS Method 3 $t_R$=2.18, 2.22 min, m/z 412, 414 (MH$^+$).

Step 2. 1-((S)-1-(4-bromophenyl)propyl)-4-(2-oxopropyl)-4-phenylpiperidin-2-one A round-bottom flask was charged with copper(I) chloride (0.3100 g, 3.13 mmol), and a solution of 4-allyl-1-((S)-1-(4-bromophenyl)propyl)-4-phenylpiperidin-2-one (0.3045 g, 0.74 mmol) in DMF (7.5 mL) was added, followed by $H_2O$ (2 mL) and palladium(II) chloride (0.0670 g, 0.38 mmol). The reaction mixture was vigorously stirred under a balloon of oxygen for 20 h at rt and diluted with EtOAc, dried over $Na_2SO_4$. After the solvents were evaporated, the residue was purified by chromatography on silica gel eluted with hexanes/EtOAc to afford 0.2475 g (78%) of 1-((S)-1-(4-bromophenyl)propyl)-4-(2-oxopropyl)-4-phenylpiperidin-2-one. LC-MS Method 3 $t_R$=1.87, 1.93 min, m/z 428, 430 (MH$^+$).

Step 3. (R)-1-((S)-1-(4-bromophenyl)propyl)-4-(2-hydroxy-2-methylpropyl)-4-phenylpiperidin-2-one and (S)-1-((S)-1-(4-bromophenyl)propyl)-4-(2-hydroxy-2-methylpropyl)-4-phenylpiperidin-2-one To a solution of 1-((S)-1-(4-bromophenyl)propyl)-4-(2-oxopropyl)-4-phenylpiperidin-2-one (0.2475 g, 0.58 mmol) in THF (5 mL) was added a solution of methylmagnesium bromide in $Et_2O$ (3.0 M, 1.0 mL, 3.0 mmol) at −78° C. under nitrogen. After 2 h at −78° C., the reaction mixture was allowed to stir at rt for additional 1.5 h. The reaction was then cooled with dry ice-acetone bath and quenched with satd aq $NH_4Cl$ (3 mL), extracted with $CH_2Cl_2$, and dried over $Na_2SO_4$. After the solvents were evaporated, the residue was purified by reversed-phase HPLC (SunFire™ Prep $C_{18}$ OBD™ 5 µm 19×250 mm column, 10%→90% $CH_3CN/H_2O$, 0.1% $CF_3COOH$ over 13 min and then 90% $CH_3CN/H_2O$, 0.1% $CF_3COOH$ over 4 min, flow rate 25 mL/min) to give two diastereomeric products.

Isomer 1: (R)-1-((S)-1-(4-bromophenyl)propyl)-4-(2-hydroxy-2-methylpropyl)-4-phenylpiperidin-2-one (0.0837 g, 33%) as a solid. LC-MS Method 3 $t_R$=1.93 min, m/z=444, 446 (MH$^+$); $^1$H NMR (400 MHz, $CD_3OD$) δ 7.16-7.07 (m, 7H), 6.81 (d, J=8.5 Hz, 2H), 5.60-5.56 (m, 1H), 3.36 (dd, J=17.7, 3.1 Hz, 1H), 2.88-2.85 (m, 1H), 2.65 (d, J=17.6 Hz, 1H), 2.08-1.76 (m, 7H), 0.89 (s, 3H), 0.84 (t, J=7.2 Hz, 3H), 0.64 (s, 3H).

Isomer 2: (S)-1-((S)-1-(4-bromophenyl)propyl)-4-(2-hydroxy-2-methylpropyl)-4-phenylpiperidin-2-one (0.0440 g, 17%), LC-MS Method 3 $t_R$=1.98 min, m/z=444, 446 (MH$^+$); $^1$H NMR (400 MHz, $CD_3OD$) δ 7.37 (d, J=8.5 Hz, 2H), 7.29-7.23 (m, 4H), 7.17-7.13 (m, 1H), 7.08 (d, J=8.5 Hz, 2H), 5.57-5.53 (m, 1H), 3.43 (dd, J=17.9, 2.9 Hz, 1H), 2.67-2.58

(m, 2H), 2.42-2.35 (m, 1H), 2.08-2.03 (m, 2H), 1.77-1.63 (m, 3H), 1.52-1.44 (m, 1H), 0.89 (s, 3H), 0.63 (s, 3H), 0.47 (t, J=7.3 Hz, 3H).

EXAMPLE 7

(R)-1-((S)-1-(4-bromophenyl)ethyl)-4-(2-hydroxy-2-methylpropyl)-4-phenylpiperidin-2-one

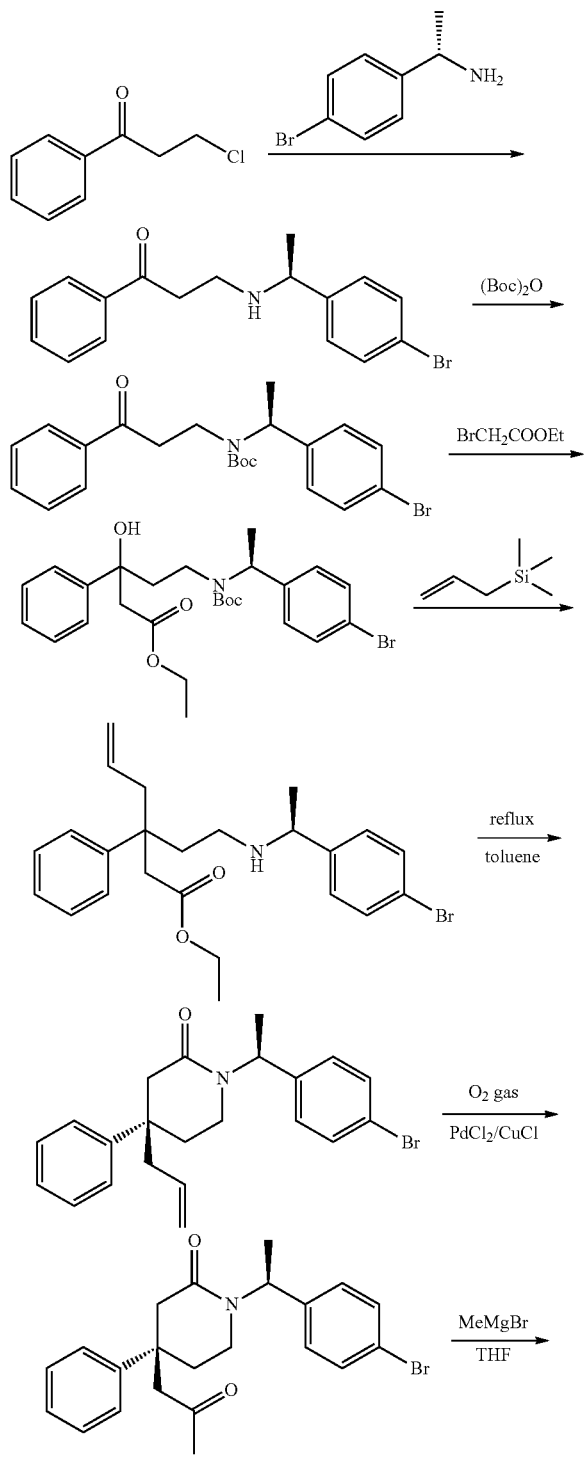

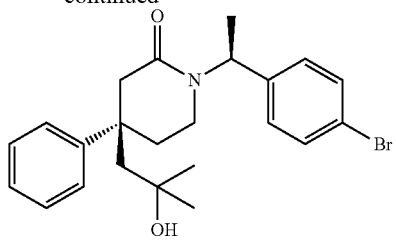

Step 1

To a solution of 3-chloro-1-phenylpropan-1-one (36 g, 214 mmol) in acetonitrile (400 mL) were added (S)-1-(4-bromophenyl)ethanamine (51 g, 256 mmol), $K_2CO_3$ (59 g, 428 mmol) and KI (71 g, 428 mmoL), and the mixture was refluxed overnight. The reaction mixture was filtered, and the filtrate was concentrated to give the crude (S)-3-(1-(4-bromophenyl)ethylamino)-1-phenylpropan-1-one (68 g), which was used to the next step without purification.

Step 2

To a solution of (S)-3-(1-(4-bromophenyl)ethylamino)-1-phenylpropan-1-one (50 g, 151 mmol) in $CH_2Cl_2$ (500 mL) was added triethylamine (46 g, 453 mmol) and di-tert-butyl dicarbonate (49 g, 226 mmol). The mixture was stirred at rt overnight. The reaction mixture was adjusted pH=6-7 with 1 N aq HCl, and extracted with $CH_2Cl_2$. The combined organic phase was washed with brine, dried over $Na_2SO_4$ and concentrated to give crude product, which was purified by column chromatography to give (S)-tert-butyl 1-(4-bromophenyl)ethyl(3-oxo-3-phenylpropyl)carbamate. (55 g, 85%).

Step 3

To a solution of give (S)-tert-butyl 1-(4-bromophenyl)ethyl(3-oxo-3-phenylpropyl)carbamate (50 g, 116 mmoL) and zinc powder (38 g, 232 mmoL) in THF (500 mL) was added iodine (71 g, 278 mmoL) and ethyl 2-bromoacetate (38.7 g, 232 mmoL) in THF dropwise. The mixture was heated to reflux for 2 h. The reaction mixture was quenched with water, and filtered. The filtrate was extracted with EtOAc. The organic phase was concentrated to give the crude product, which was purified by column chromatography to give ethyl 5-(((S)-1-(4-bromophenyl)ethyl)(tert-butoxycarbonyl)amino)-3-hydroxy-3-phenyl pentanoate. (25 g, 38%).
$^1$H NMR (CDCl$_3$): δ 1.03 (m, 3H), 1.08-1.23 (m, 3H), 1.33 (m, 9H), 1.75 (m, 1H), 1.89 (m, 1H), 2.52 (m, 2H), 2.75 (m, 1H), 2.99 (m, 1H), 3.92 (m, 2H), 4.05 (m, 1H), 4.78 (m, 1H), 6.96 (m, 2H), 7.15 (m, 3H), 7.26 (m, 2H), 7.32 (m, 2H), 7.39 (m, 1H).

Step 4

To a solution of ethyl 5-(((S)-1-(4-bromophenyl)ethyl)(tert-butoxycarbonyl)amino)-3-hydroxy-3-phenylpentanoate (24 g, 46.2 mmoL) in anhydrous $CH_2Cl_2$ (240 mL), cooled to –78° C. under nitrogen was added allyltrimethylsilane (53 g, 462 mmoL), followed by the dropwise addition of a solution of titanium(IV) chloride (44 g, 236 mmoL) in $CH_2Cl_2$ (236 mL). The solution was stirred at –78° C. for 0.5 h, and then allowed to warm to rt, and heated to reflux overnight. The reaction mixture was quenched with aqueous $NaSO_4$ solution, the organic phase was separated and concentrated to give the crude product, which was purified by column chromatography to give ethyl 3-(2-((S)-1-(4-bromophenyl)ethylamino)ethyl)-3-phenylhex-5-enoate (4.67 g, 22%).
$^1$H NMR (CDCl$_3$): δ 1.03 (m, 3H), 1.15 (m, 3H), 1.20 (m, 2H), 1.91 (m, 2H), 2.20 (m, 2H), 2.52 (m, 2H), 3.91 (m, 2H), 3.99 (m, 1H), 4.89 (m, 1H), 4.94 (m, 1H), 5.48 (m, 1H), 7.01 (m, 2H), 7.14 (m, 1H), 7.18 (m, 2H), 7.25 (m, 2H), 7.31 (m, 2H).

83

Step 5

To a solution of ethyl 3-(2-((S)-1-(4-bromophenyl)ethylamino)ethyl)-3-phenylhex-5-enoate (4.6 g, 9.1 mmol) in anhydrous toluene (80 mL) was heated to reflux for 2 days. The reaction was concentrated to give the crude (S)-4-allyl-1-((S)-1-(4-bromophenyl)ethyl)-4-phenylpiperidin-2-one. The residue was purified by column chromatography to give the final product (1.2 g, 33%). ¹H NMR (CDCl₃): δ 1.13 (m, 3H), 1.76 (m, 1H), 1.97 (m, 1H), 2.24 (m, 1H), 2.43 (m, 2H), 2.57 (m, 2H), 2.94 (m, 1H), 4.89 (m, 2H), 5.35 (m, 1H), 6.01 (m, 1H), 7.03 (m, 2H), 7.21 (m, 3H), 7.30 (m, 2H), 7.42 (m, 2H).

Step 6

In a three-necked flask, a mixture of PdCl₂ (180 mg, 1 mmol) and CuCl (500 mg, 5 mmol) in aqueous DMF (15 mL of DMF and 5 mL of water) was stirred under an oxygen atmosphere for 1 h at rt, and (S)-4-allyl-1-((S)-1-(4-bromophenyl)ethyl)-4-phenylpiperidin-2-one (2 g, purity=65%, 3.3 mmol) was added. The mixture was stirred vigorously under an oxygen atmosphere for 24 h at rt. The reaction mixture was quenched with aq NaHCO₃ solution. The organic phase was washed with brine, and dried over NaSO₄. After evaporation of the solvent, the residue was purified by prep TLC to give (R)-1-((S)-1-(4-bromophenyl)ethyl)-4-(2-oxopropyl)-4-phenylpiperidin-2-one (400 mg, 29.6%))

Step 7

To a solution of (R)-1-((S)-1-(4-bromophenyl)ethyl)-4-(2-oxopropyl)-4-phenyl piperidin-2-one (82 mg, 0.2 mmol) in anhydrous THF (20 mL) was added dropwise methylmagnesium bromide (0.4 mL, 3M) at -78° C. under nitrogen. The formed mixture was stirred at rt for 1 h. The reaction mixture was quenched with aq NaHCO₃ solution (5 mL). The layers were separated. The aqueous layer was extracted with EtOAc (3×8 mL). The combined organic phase was washed with a satd aq NaCl (5 mL), dried over Na₂SO₄ and concentrated in vacuo to give the crude product, which was purified by preparative HPLC to afford (R)-1-((S)-1-(4-bromophenyl)ethyl)-4-(2-hydroxy-2-methylpropyl)-4-phenylpiperidin-2-one (60 mg, 70.5%). LC-MS Method 2, $t_R$=2.131 min, m/z=454. ¹H NMR (CDCl₃): δ 0.85 (s, 3H), 1.05 (s, 3H), 1.46 (m, 3H), 1.85-1.89 (m, 1H), 1.96-2.18 (m, 4H), 2.73-2.76 (m, 1H), 2.89-2.94 (m, 1H), 3.58-3.63 (m, 1H), 5.91-5.96 (m, 1H), 6.95-6.97 (m, 1H), 7.21-7.34 (m, 7H).

EXAMPLE 8

4-(4-((S)-1-((R)-4-(2-hydroxy-2-methylpropyl)-2-oxo-4-phenylpiperidin-1-yl)ethyl)phenyl)-1-methylpyridin-2(1H)-one

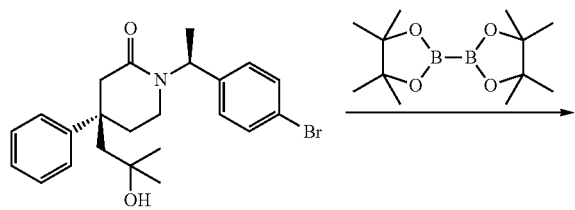

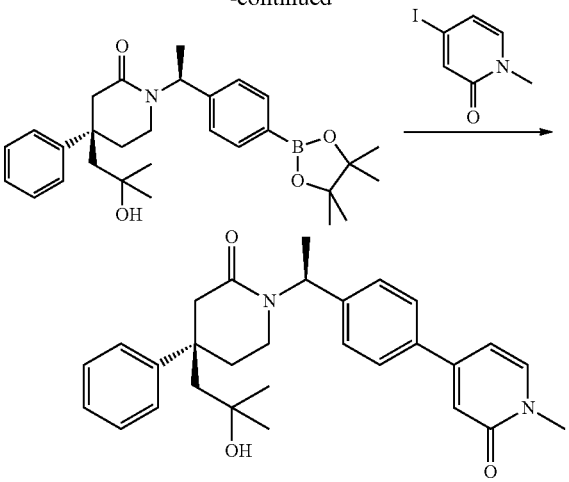

Step 1

To a solution of (R)-1-((S)-1-(4-bromophenyl)ethyl)-4-(2-hydroxy-2-methylpropyl)-4-phenylpiperidin-2-one (150 mg, 0.35 mmol) and 4,4,4',4',5,5,5',5'-octamethyl-2,2'-bi(1,3,2-dioxaborolane) (133 mg, 0.52 mmol) in dry DMSO (5 mL) were added KOAc (86 mg, 0.875 mmol) and Pd(dppf)Cl₂ (80 mg, 0.875 mmol). After addition, the mixture was warmed to 100° C. for 2 h. After TLC showed the starting material had disappeared, the solid was filtered off. Water (8 mL) and EtOAc (10 mL) were added, the organic layer was separated and the aqueous layer was extracted with EtOAc (3×5 mL). The combined organic layer was washed with brine, dried over Na₂SO₄, filtered, and concentrated to give (R)-4-(2-hydroxy-2-methylpropyl)-4-phenyl-1-((S)-1-(4-(4,4,5,5-tetramethyl-1,3,2-dioxaborolan-2-yl)phenyl)ethyl)piperidin-2-one (40 mg, 24%), which was purified by column chromatography.

Step 2

To a solution of (R)-4-(2-hydroxy-2-methylpropyl)-4-phenyl-1-((S)-1-(4-(4,4,5,5-tetramethyl-1,3,2-dioxaborolan-2-yl)phenyl)ethyl)piperidin-2-one (20 mg, 0.042 mmol) and 4-iodo-1-methylpyridin-2(1H)-one (7.8 mg, 0.084 mmol) in dry 1,4-dioxane (5 mL) was added Cs₂CO₃ (0.042 mL, 0.084 mmol) and Pd(PPh₃)₂Cl₂ (10 mg). After addition, the mixture was warmed at 110° C. for 2 h under nitrogen. After TLC showed the starting material had disappeared, the solid was filtered off. Water (20 mL) and EtOAc (10 mL) were added, the organic layer was separated, and the aqueous layer was extracted with EtOAc (3×10 mL). The combined organic layers were washed with brine, dried over Na₂SO₄, filtered, and concentrated to give 4-(4-((S)-1-((R)-4-(2-hydroxy-2-methylpropyl)-2-oxo-4-phenylpiperidin-1-yl)ethyl)phenyl)-1-methylpyridin-2(1H)-one (2.63 mg, 14%), which was purified by preparative HPLC. LC-MS Method 2, $t_R$=1.163 min, m/z=459.2. ¹H NMR (CDCl₃): δ 0.81 (s, 3H), 0.98 (s, 3H), 1.41 (d, 3H), 1.80 (m, 1H), 1.96 (m, 1H), 1.99-2.18 (m, 4H), 2.58 (m, 1H), 2.87 (m, 1H), 3.47 (m, 1H), 3.57 (s, 3H), 5.95 (m, 1H), 6.41 (m, 1H), 6.80 (s, 1H), 6.91 (m, 2H), 7.18 (m, 1H), 7.24 (m, 6H), 7.32 (d, 1H).

EXAMPLE 9

5-(4-((S)-1-((R)-4-(2-hydroxy-2-methylpropyl)-2-oxo-4-phenylpiperidin-1-yl)ethyl)phenyl)-1-methylpyridin-2(1H)-one

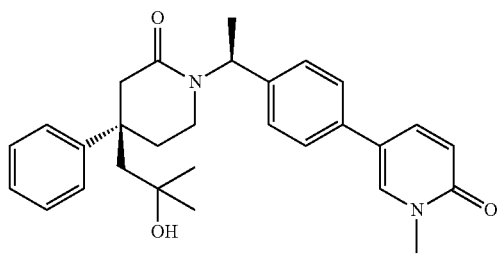 [SMILES: C[C@@H](c1ccc(-c2ccc(=O)n(C)c2)cc1)N1CC[C@](CC(C)(C)O)(c2ccccc2)CC1=O]

The title compound was prepared from (R)-4-(2-hydroxy-2-methylpropyl)-4-phenyl-1-((S)-1-(4-(4,4,5,5-tetramethyl-1,3,2-dioxaborolan-2-yl)phenyl)ethyl)piperidin-2-one and 5-bromo-1-methylpyridin-2(1H)-one following a procedure analogous to that described in Example 8 Step 2. LC-MS Method 2, $t_R$=1.171 min, m/z=459.2. $^1$H NMR (CDCl$_3$) d 0.88 (s, 3H), 1.16 (s, 3H), 1.49 (d, 3H), 1.88 (m, 1H), 1.98-2.19 (m, 2H), 2.19-2.23 (m, 2H), 2.79 (m, 1H), 2.94 (m, 1H), 3.53 (m, 1H), 3.69 (s, 3H), 6.00 (m, 1H), 6.83 (m, 1H), 6.94 (m, 2H), 7.10 (m, 2H), 7.21 (m, 1H), 7.30 (m, 4H), 7.47 (s, 1H), 7.62 (d, 1H).

EXAMPLE 10

3-((S)-1-((S)-1-(4-bromophenyl)ethyl)-2-oxo-4-phenylpiperidin-4-yl)-2,2-dimethylpropanenitrile

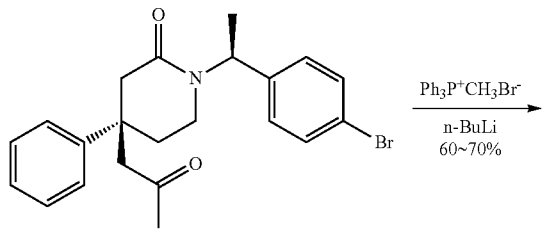

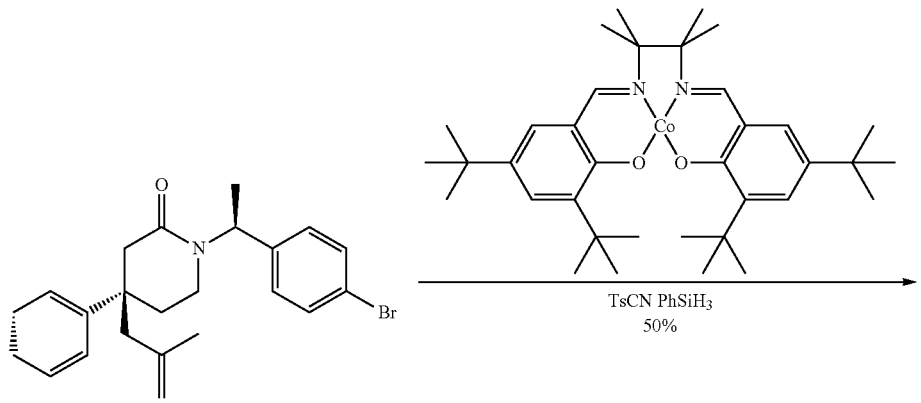

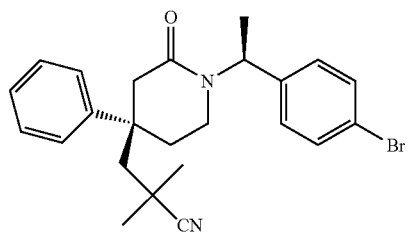

Step 1

To a solution of CH₃PPh₃Br (863.9 mg 2.42 mmol) in THF (8 mL) was added n-BuLi (0.678 ml, 1.69 mmol) at −78° C. under N₂. The mixture was stirred at rt for 1 h, a solution of (R)-1-((S)-1-(4-bromophenyl)ethyl)-4-(2-oxopropyl)-4-phenylpiperidin-2-one (100 mg 0.24 mmol) in THF (5 mL) was added, and the mixture was stirred at reflux overnight. The reaction was quenched by satd aq NH₄Cl and extracted with EtOAc. The combined organic phase was dried and concentrated to give the crude product, which was purified by preparative TLC to give (S)-1-((S)-1-(4-bromophenyl)ethyl)-4-(2-methylallyl)-4-phenylpiperidin-2-one (60 mg, 60%).

Step 2

A solution of (S)-1-((S)-1-(4-bromophenyl)ethyl)-4-(2-methylallyl)-4-phenylpiperidin-2-one (30 mg, 0.07 mmol), the cobalt(II) complex whose preparation is described below (0.46 mg, 0.0007 mmol), TsCN (19.8 mg, 0.11 mmol) and PhSiH₃ (8.4 mg, 0.08 mmol) in anhydrous EtOH (5 mL) was stirred at rt for 4 h. After the solvent was removed under reduced pressure, the residue was purified by preparative TLC to give 3-((S)-1-((S)-1-(4-bromophenyl)ethyl)-2-oxo-4-phenyl piperidin-4-yl)-2,2-di methylpropanenitrile (15 mg, 50%). LC-MS Method Preparation of Cobalt(II) Complex Used in Step 2

A 50 mL flask was charged with N,N'-bis(3,5-di-tert-butylsalicylidene)-1,1,2,2-tetramethylethenediamine (0.4302 g, 0.78 mmol, 1.0 equiv), EtOH (17 mL), and Co(OAc)₂ (0.1385 g, 0.78 mmol, 1.0 equiv). The mixture was degassed and then heated to reflux under nitrogen for 3 h, cooled to room temperature. The precipitate was filtered and the purple solid was washed with EtOH (10 mL) and dried under high vacuum to give 0.3533 g (75%) of the cobalt(II) complex.

EXAMPLE 11

3-((S)-1-((S)-1-(4-bromophenyl)ethyl)-2-oxo-4-phenylpiperidin-4-yl)-2,2-dimethylpropanamide

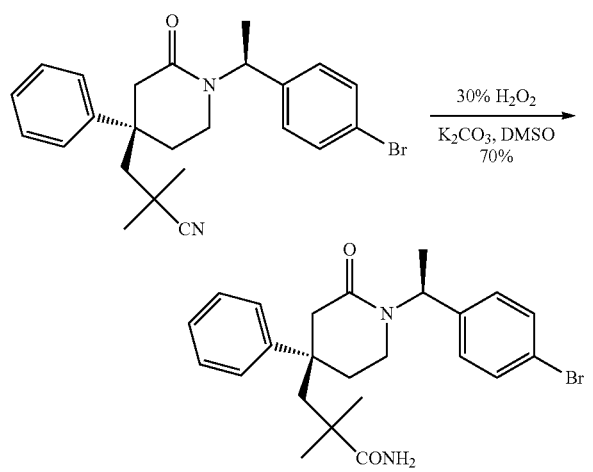

To a solution of 3-((S)-1-((S)-1-(4-bromophenyl)ethyl)-2-oxo-4-phenylpiperidin-4-yl)-2,2-dimethylpropanenitrile (11 mg, 0.025 mmol) in DMSO (3 mL) were added K₂CO₃ (6.9 mg 0.05 mmol) and 30% H₂O₂ (5.7 mg 0.05 mmol). The mixture was stirred at rt overnight. After being diluted with water (2 mL), the mixture was washed with EtOAc (3×2 mL). The aqueous layer was acidified to pH=3-4, and extracted with EtOAc (3×2 mL). The combined organic layers were washed with brine (3×2 mL), dried over anhydrous Na₂SO₄, filtered, and concentrated under vacuum. The crude product was dried under vacuum and purified by TLC and preparative HPLC to give 3-((S)-1-((S)-1-(4-bromophenyl)ethyl)-2-oxo-4-phenylpiperidin-4-yl)-2,2-dimethylpropanamide (8 mg, 70%). LC-MS Method 2 t_R=1.36 min, m/z=481, 479, 459, 457; ¹H NMR (CDCl₃): δ 0.78 (s, 3H), 1.08 (s, 3H), 1.40 (d, 3H), 2.0 (m, 4H), 2.18 (m, 1H), 2.66 (m, 1H), 2.81 (m, 1H), 3.32 (m, 1H), 5.58 (m, 1H), 5.84 (m, 1H), 6.18 (m, 1H), 6.68 (m, 2H), 7.16 (m, 2H), 7.20 (m, 5H).

EXAMPLE 12

4-(4-((S)-1-((R)-4-(2-hydroxy-2-methylpropyl)-2-oxo-4-phenylpiperidin-1-yl)ethyl)phenyl)pyridin-2 (1H)-one

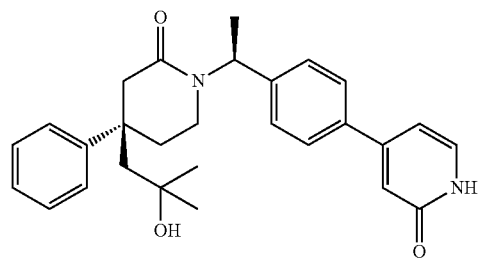 [SMILES: C[C@@H](c1ccc(-c2cc[nH]c(=O)c2)cc1)N1CC[C@](CC(C)(C)O)(c2ccccc2)CC1=O]

The title compound was prepared from (R)-4-(2-hydroxy-2-methylpropyl)-4-phenyl-1-((S)-1-(4-(4,4,5,5-tetramethyl-1,3,2-dioxaborolan-2-yl)phenyl)ethyl)piperidin-2-one and 4-iodopyridin-2(1H)-one following a procedure analogous to that described in Example 8 Step 2. LC-MS Method 2 t_R=0.9 min, m/z=444.9; ¹H NMR (CDCl₃) δ 0.87 (s, 3H), 1.00 (s, 3H), 1.42 (d, 3H), 1.81 (d, 2H), 2.00 (m, 4H), 2.65 (d, 1H), 2.85 (m, 1H), 3.42 (m, 1H), 6.0 (m, 1H), 6.40 (m, 1H), 6.62 (s, 1H), 6.92 (d, 2H), 7.17 (m, 1H), 7.25 (m, 6H), 7.33 (m, 1H).

EXAMPLE 13

5-(4-((S)-1-((R)-4-(2-hydroxy-2-methylpropyl)-2-oxo-4-phenylpiperidin-1-yl)ethyl)phenyl)pyridin-2 (1H)-one

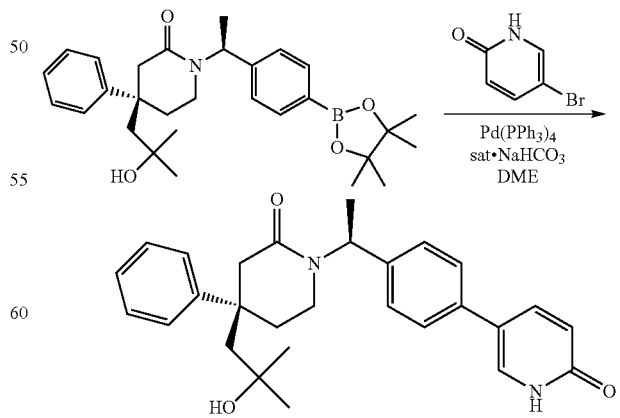

To a solution of 5-bromopyridin-2(1H)-one (30 mg, 0.17 mmol) in DME (6 mL) was added Pd(PPh₃)₄ (10 mg, 0.01 mmol) under N$_2$. The mixture was stirred at rt for 1 h. (R)-4-(2-hydroxy-2-methylpropyl)-4-phenyl-1-((S)-1-(4-(4,4,5,5-tetramethyl-1,3,2-dioxaborolan-2-yl)phenyl)ethyl)piperidin-2-one (25 mg, 0.05 mmol) in EtOH (2 mL) was added, followed by satd aq NaHCO$_3$ (2 mL). The mixture was stirred at 100° C. for another 2 h under N$_2$. The reaction was quenched with H$_2$O, and extracted with EtOAc (3×). The combined organic phase was dried and concentrated to give the crude final product, which was purified by preparative TLC to give 5-(4-((S)-1-((R)-4-(2-hydroxy-2-methylpropyl)-2-oxo-4-phenylpiperidinyl)ethyl)phenyl)pyridin-2 (1H)-one (4.5 mg, 20%). LC-MS Method 2 $t_R$=1.034 min, m/z=445.2; $^1$H NMR (CDCl$_3$): δ 0.86 (s, 3H), 1.02 (s, 3H), 1.41 (d, 3H), 1.82 (d, 2H), 2.00 (m, 2H), 2.11 (m, 2H), 2.62 (d, 1H), 2.85 (m, 1H), 3.42 (d, 1H), 6.0 (m, 1H), 6.69 (m, 1H), 6.88 (m, 2H), 7.09 (m, 2H), 7.17 (m, 1H), 7.25 (m, 4H), 7.51 (m, 1H), 7.78 (m, 1H).

BIOLOGICAL TEST EXAMPLE 1

The inhibition of a microsomal preparation of 11β-HSD1 by compounds of the invention was measured essentially as previously described (K. Solly, S. S. Mundt, H. J. Zokian, G. J. Ding, A. Hermanowski-Vosatka, B. Strulovici, and W. Zheng, High-Throughput Screening of 11-Beta-Hydroxyseroid Dehydrogenase Type 1 in Scintillation Proximity Assay Format. Assay Drug Dev Technol 3 (2005) 377-384). All reactions were carried out at rt in 96 well clear flexible PET Microbeta plates (PerkinElmer). The assay begins by dispensing 49 μl of substrate solution (50 mM HEPES, pH 7.4, 100 mM KCl, 5 mM NaCl, 2 mM MgCl$_2$, 2 mM NADPH and 160 nM [$^3$H]cortisone (1 Ci/mmol)) and mixing in 1 μL of the test compounds in DMSO previously diluted in half-log increments (8 points) starting at 0.1 mM. After a 10 minute pre-incubation, 50 μL of enzyme solution containing microsomes isolated from CHO cells overexpressing human 11β-HSD1 (10-20 μg/ml of total protein) was added, and the plates were incubated for 90 minutes at rt. The reaction was stopped by adding 50 μl of the SPA beads suspension containing 10 μM 18β-glycyrrhetinic acid, 5 mg/ml protein A coated YSi SPA beads (GE Healthcare) and 3.3 μg/ml of anti-cortisol antibody (East Coast Biologics) in Superblock buffer (Bio-Rad). The plates were shaken for 120 minutes at rt, and the SPA signal corresponding to [$^3$H]cortisol was measured on a Microbeta plate reader.

BIOLOGICAL TEST EXAMPLE 2

The inhibition of 11β-HSD1 by compounds of this invention was measured in whole cells as follows. Cells for the assay were obtained from two sources: fully differentiated human omental adipocytes from Zen-Bio, Inc.; and human omental pre-adipocytes from Lonza Group Ltd. Pre-differentiated omental adipocytes from Zen-Bio Inc. were purchased in 96-well plates and were used in the assay at least two weeks after differentiation from precursor preadipocytes. Zen-Bio induced differentiation of pre-adipocytes by supplementing medium with adipogenic and lipogenic hormones (human insulin, dexamethasone, isobutylmethylxanthine and PPAR-gamma agonist). The cells were maintained in full adipocyte medium (DMEM/Ham's F-12 (1:1, v/v), HEPES pH 7.4, fetal bovine serum, penicillin, streptomycin and Amphotericin B, supplied by Zen-Bio, Inc.) at 37° C., 5% CO$_2$.

Pre-adipocytes were purchased from Lonza Group Ltd. and placed in culture in Preadipocyte Growth Medium-2 supplemented with fetal bovine serum, penicillin, and streptomycin (supplied by Lonza) at 37° C., 5% CO$_2$. Pre-adipocytes were differentiated by the addition of insulin, dexamethasone, indomethacin and isobutyl-methylxanthine (supplied by Lonza) to the Preadipocyte Growth Medium-2. Cells were exposed to the differentiating factors for 7 days, at which point the cells were differentiated and ready for the assay. One day before running the assay, the differentiated omental adipocytes were transferred into serum- and phenol-red-free medium for overnight incubation. The assay was performed in a total volume of 200 μL. The cells were pre-incubated with serum-free, phenol-red-free medium containing 0.1% (v/v) of DMSO and various concentrations of the test compounds at least 1 h before [$^3$H] cortisone in ethanol (50 Ci/mmol, ARC, Inc.) was added to achieve a final concentration of cortisone of 100 nM. The cells were incubated for 3-4 hrs at 37° C., 5% CO$_2$. Negative controls were incubated without radioactive substrate and received the same amount of [$^3$H] cortisone at the end of the incubation. Formation of [$^3$H] cortisol was monitored by analyzing 25 μL of each supernatant in a scintillation proximity assay (SPA). (Solly, K.; Mundt, S. S.; Zokian, H. J.; Ding, G. J.; Hermanowski-Vosatka, A.; Strulovici, B.; Zheng, W. Assay Drug Dev. Technol. 2005, 3, 377-384). Many compounds of the invention showed significant activity in this assay.

| TABLE OF BIOLOGICAL ASSAY RESULTS | | |
|---|---|---|
| | Biological Test Example 1 | |
| Compound | IC$_{50}$ Range$^a$ | Average % inhibition at 100 nM |
| EXAMPLE 1 Isomer 1 | nt | nt |
| EXAMPLE 1 Isomer 2 | nt | nt |
| EXAMPLE 2 Isomer 1 | ++ | 100.7 |
| EXAMPLE 2 Isomer 2 | ++ | 73.8 |
| EXAMPLE 3 Isomer 1 | ++ | 97.9 |
| EXAMPLE 3 Isomer 2 | ++ | 61.3 |
| EXAMPLE 4 Isomer 1 | ++ | 96.8 |
| EXAMPLE 4 Isomer 2 | # | 27.8 |
| EXAMPLE 5 Isomer 1 | ++ | 94.0 |
| EXAMPLE 5 Isomer 2 | # | 10.7 |
| EXAMPLE 6 Isomer 1 | ++ | 98.3 |
| EXAMPLE 6 Isomer 2 | ++ | 82.6 |
| EXAMPLE 7 | ++ | 98.0 |
| EXAMPLE 8 | ++ | 93.0 |
| EXAMPLE 9 | ++ | 92.7 |
| EXAMPLE 10 | ++ | 96.0 |
| EXAMPLE 11 | ++ | 95.5 |
| EXAMPLE 12 | ++ | 95.9 |
| EXAMPLE 13 | ++ | 94.3 |

$^a$++ means IC$_{50}$ = <100 nM,
# means IC$_{50}$ >100 nM, nt means not tested.

| PROPHETIC COMPOUNDS | |
|---|---|
| Number | Compound Name |
| 1 | 4-methyl-4-phenyl-1-m-tolylpiperidin-2-one |
| 2 | 1-(3-bromophenyl)-4-methyl-4-phenylpiperidin-2-one |
| 3 | 1-(biphenyl-3-yl)-4-methyl-4-phenylpiperidin-2-one |
| 4 | 1-(2'-chlorobiphenyl-3-yl)-4-methyl-4-phenylpiperidin-2-one |
| 5 | 3'-(4-methyl-2-oxo-4-phenylpiperidin-1-yl)biphenyl-2-carbonitrile |
| 6 | 1-(2'-methoxybiphenyl-3-yl)-4-methyl-4-phenylpiperidin-2-one |
| 7 | 1-(2',6'-dichlorobiphenyl-3-yl)-4-methyl-4-phenylpiperidin-2-one |
| 8 | 1-(2',4'-difluorobiphenyl-3-yl)-4-methyl-4-phenylpiperidin-2-one |
| 9 | 1-(3'-chlorobiphenyl-3-yl)-4-methyl-4-phenylpiperidin-2-one |
| 10 | 1-(3'-fluorobiphenyl-3-yl)-4-methyl-4-phenylpiperidin-2-one |

| Number | Compound Name |
|---|---|
| 11 | 1-(2',5'-difluorobiphenyl-3-yl)-4-methyl-4-phenylpiperidin-2-one |
| 12 | 1-(3',5'-difluorobiphenyl-3-yl)-4-methyl-4-phenylpiperidin-2-one |
| 13 | 1-(4'-fluorobiphenyl-3-yl)-4-methyl-4-phenylpiperidin-2-one |
| 14 | (S)-1-(4'-fluorobiphenyl-3-yl)-4-methyl-4-phenylpiperidin-2-one |
| 15 | 1-(2'-fluorobiphenyl-3-yl)-4-methyl-4-phenylpiperidin-2-one |
| 16 | 1-(4'-hydroxybiphenyl-3-yl)-4-methyl-4-phenylpiperidin-2-one |
| 17 | 1-(6-(2-chloro-4-fluorophenyl)pyridin-2-yl)-4-(2-fluorophenyl)-4-(2-hydroxyethyl)piperidin-2-one |
| 18 | 2-((R)-1-((S)-1-(2',4'-difluorobiphenyl-4-yl)ethyl)-4-(4-fluorophenyl)-2-oxopiperidin-4-yl)acetamide |
| 19 | (4R)-1-((S)-1-(2',4'-difluorobiphenyl-4-yl)ethyl)-4-(2,3-dihydroxypropyl)-4-(4-fluorophenyl)piperidin-2-one |
| 19 Isomer 1 | (R)-1-((S)-1-(2',4'-difluorobiphenyl-4-yl)ethyl)-4-((R)-2,3-dihydroxypropyl)-4-(4-fluorophenyl)piperidin-2-one |
| 19 Isomer 2 | (R)-1-((S)-1-(2',4'-difluorobiphenyl-4-yl)ethyl)-4-((S)-2,3-dihydroxypropyl)-4-(4-fluorophenyl)piperidin-2-one |
| 20 | 4-allyl-1-(2',4'-difluorobiphenyl-3-yl)-4-phenylpiperidin-2-one |
| 21 | 1-(2',4'-difluorobiphenyl-3-yl)-4-(2-hydroxyethyl)-4-phenylpiperidin-2-one |
| 22 | (R)-1-(2',4'-difluorobiphenyl-3-yl)-4-(2-hydroxyethyl)-4-phenylpiperidin-2-one |
| 23 | 1-(4',6-difluorobiphenyl-3-yl)-4-(4-fluorophenyl)-4-(2-hydroxyethyl)piperidin-2-one |
| 24 | 1-(4',6-difluorobiphenyl-3-yl)-4-(2-fluorophenyl)-4-(2-hydroxyethyl)piperidin-2-one |
| 25 | 1-(2'-chloro-4'-fluorobiphenyl-3-yl)-4-(2-hydroxyethyl)-4-phenylpiperidin-2-one |
| 26 | 1-(2',6'-dichlorobiphenyl-3-yl)-4-(2-hydroxyethyl)-4-phenylpiperidin-2-one |
| 27 | 2-(1-(2',4'-difluorobiphenyl-3-yl)-2-oxo-4-phenylpiperidin-4-yl)acetamide |
| 28 | 1-(2',4'-difluorobiphenyl-3-yl)-4-(2,3-dihydroxypropyl)-4-phenylpiperidin-2-one |
| 29 | 1-(2',4'-difluorobiphenyl-3-yl)-4-(3-hydroxypropyl)-4-phenylpiperidin-2-one |
| 30 | 1-(biphenyl-3-yl)-4-(3-chlorophenyl)-4-methylpiperidin-2-one |
| 31 | 1-(2',4'-difluorobiphenyl-3-yl)-4-methyl-4-(pyridin-2-yl)piperidin-2-one |
| 32 | 4-methyl-4-phenyl-1-((1S)-1-phenylethyl)piperidin-2-one |
| 33 | 1-((1S)-1-(3-methoxyphenyl)ethyl)-4-methyl-4-phenylpiperidin-2-one |
| 34 | 1-((1S)-1-(4-methoxyphenyl)ethyl)-4-methyl-4-phenylpiperidin-2-one |
| 35 | 4-methyl-1-((1S)-1-phenylethyl)-4-o-tolylpiperidin-2-one |
| 36 | 4-methyl-1-((1S)-1-phenylethyl)-4-m-tolylpiperidin-2-one |
| 37 | 4-methyl-1-((1S)-1-phenylethyl)-4-p-tolylpiperidin-2-one |
| 38 | 4-methyl-4-(4-(methylthio)phenyl)-1-((1S)-1-phenylethyl)piperidin-2-one |
| 39 | 4-allyl-4-(4-fluorophenyl)-1-((1S)-1-phenylethyl)piperidin-2-one |
| 40 | 1-(4',6-difluorobiphenyl-3-yl)-4-(2-hydroxyethyl)-4-phenylpiperidin-2-one |
| 41 | (R)-1-(4',6-difluorobiphenyl-3-yl)-4-(2-hydroxyethyl)-4-phenylpiperidin-2-one |
| 42 | (R)-4-(4-fluorophenyl)-4-(2-hydroxyethyl)-1-((S)-1-phenylethyl)piperidin-2-one |
| 43 | N-(2-(1-(2',4'-difluorobiphenyl-3-yl)-2-oxo-4-phenylpiperidin-4-yl)ethyl)acetamide |
| 44 | N-(2-(1-(2',4'-difluorobiphenyl-3-yl)-2-oxo-4-phenylpiperidin-4-yl)ethyl)methanesulfonamide |
| 45 | 1-(2'-chloro-4',6-difluorobiphenyl-3-yl)-4-(4-fluorophenyl)-4-(2-hydroxyethyl)piperidin-2-one |
| 46 | 1-(2'-chloro-4',6-difluorobiphenyl-3-yl)-4-(2-hydroxyethyl)-4-phenylpiperidin-2-one |
| 47 | 1-(6-(4-fluorophenyl)pyridin-2-yl)-4-(2-hydroxyethyl)-4-phenylpiperidin-2-one |
| 48 | (R)-1-(6-(4-fluorophenyl)pyridin-2-yl)-4-(2-hydroxyethyl)-4-phenylpiperidin-2-one |
| 49 | 4-(4-fluorophenyl)-1-(6-(4-fluorophenyl)pyridin-2-yl)-4-(2-hydroxyethyl)piperidin-2-one |
| 50 | 4-(2-fluorophenyl)-1-(6-(4-fluorophenyl)pyridin-2-yl)-4-(2-hydroxyethyl)piperidin-2-one |
| 51 | (R)-4-(2-fluorophenyl)-1-(6-(4-fluorophenyl)pyridin-2-yl)-4-(2-hydroxyethyl)piperidin-2-one |
| 52 | 4-(4-fluorophenyl)-4-(2-hydroxyethyl)-1-(2',4',6-trifluorobiphenyl-3-yl)piperidin-2-one |
| 53 | 4-(2-fluorophenyl)-4-(2-hydroxyethyl)-1-(2',4',6-trifluorobiphenyl-3-yl)piperidin-2-one |
| 54 | 1-(6-(2,4-difluorophenyl)pyridin-2-yl)-4-(2-hydroxyethyl)-4-phenylpiperidin-2-one |
| 55 | 1-(6-(2,4-difluorophenyl)pyridin-2-yl)-4-(4-fluorophenyl)-4-(2-hydroxyethyl)piperidin-2-one |
| 56 | 1-(6-(2,4-difluorophenyl)pyridin-2-yl)-4-(2-fluorophenyl)-4-(2-hydroxyethyl)piperidin-2-one |
| 57 | (R)-1-(6-(2,4-difluorophenyl)pyridin-2-yl)-4-(2-fluorophenyl)-4-(2-hydroxyethyl)piperidin-2-one |
| 58 | (R)-4-allyl-1-((S)-1-(4-bromophenyl)ethyl)-4-(4-fluorophenyl)piperidin-2-one |
| 59 | (R)-4-allyl-1-((S)-1-(4-bromophenyl)ethyl)-4-(4-fluorophenyl)piperidin-2-one |
| 60 | (R)-4-allyl-1-((S)-1-(2',4'-difluorobiphenyl-4-yl)ethyl)-4-(4-fluorophenyl)piperidin-2-one |
| 61 | (S)-4-allyl-1-((S)-1-(2',4'-difluorobiphenyl-4-yl)ethyl)-4-(4-fluorophenyl)piperidin-2-one |
| 62 | (R)-1-((S)-1-(2',4'-difluorobiphenyl-4-yl)ethyl)-4-(4-fluorophenyl)-4-(2-hydroxyethyl)piperidin-2-one |
| 63 | (R)-4-(4-fluorophenyl)-1-((S)-1-phenylethyl)-4-vinylpiperidin-2-one |
| 64 | (S)-4-(4-fluorophenyl)-1-((S)-1-phenylethyl)-4-vinylpiperidin-2-one |
| 65 | (R)-1-((S)-1-(4-bromophenyl)ethyl)-4-(4-fluorophenyl)-4-(2-hydroxyethyl)piperidin-2-one |
| 66 | 1-(6-(2-chloro-4-fluorophenyl)pyridin-2-yl)-4-(2-hydroxyethyl)-4-phenylpiperidin-2-one |
| 67 | 1-(6-(2-chloro-4-fluorophenyl)pyridin-2-yl)-4-(4-fluorophenyl)-4-(2-hydroxyethyl)piperidin-2-one |
| 68 | (R)-1-((S)-1-(4'-fluorobiphenyl-4-yl)ethyl)-4-(4-fluorophenyl)-4-(2-hydroxyethyl)piperidin-2-one |
| 69 | (S)-4-allyl-1-((S)-1-cyclohexylethyl)-4-(4-fluorophenyl)piperidin-2-one |
| 70 | (R)-4-allyl-1-((S)-1-cyclohexylethyl)-4-(4-fluorophenyl)piperidin-2-one |
| 71 | (S)-1-((S)-1-cyclohexylethyl)-4-(4-fluorophenyl)-4-(3-hydroxypropyl)piperidin-2-one |
| 72 | (S)-4-allyl-1-((S)-1-(4-cyclopropylphenyl)ethyl)-4-(4-fluorophenyl)piperidin-2-one |
| 73 | methyl 4-((S)-1-((S)-4-allyl-4-(4-fluorophenyl)-2-oxopiperidin-1-yl)ethyl)benzoate |
| 74 | (S)-1-((S)-1-(4-cyclopropylphenyl)ethyl)-4-(4-fluorophenyl)-4-(3-hydroxypropyl)piperidin-2-one |
| 75 | methyl 4-((S)-1-((S)-4-(4-fluorophenyl)-4-(3-hydroxypropyl)-2-oxopiperidin-1-yl)ethyl)benzoate |
| 76 | (S)-4-allyl-1-((S)-1-(4-bromophenyl)propyl)-4-(4-fluorophenyl)piperidin-2-one |
| 77 | (R)-4-allyl-1-((S)-1-(4-bromophenyl)propyl)-4-(4-fluorophenyl)piperidin-2-one |
| 78 | 1-(5-chloro-6-(4-fluorophenyl)pyridin-2-yl)-4-(2-fluorophenyl)-4-(2-hydroxyethyl)piperidin-2-one |
| 79 | (S)-4-(2-aminoethyl)-1-((S)-1-(2',4'-difluorobiphenyl-4-yl)ethyl)-4-(4-fluorophenyl)piperidin-2-one |
| 80 | 1-(4-chloro-6-(2,4-difluorophenyl)pyridin-2-yl)-4-(2-fluorophenyl)-4-(2-hydroxyethyl)piperidin-2-one |
| 81 | (S)-1-((S)-1-(2',4'-difluorobiphenyl-4-yl)ethyl)-4-(4-fluorophenyl)-4-(3-hydroxypropyl)piperidin-2-one |
| 82 | (R)-1-((S)-1-(2',4'-difluorobiphenyl-4-yl)ethyl)-4-(4-fluorophenyl)-4-((S)-2-hydroxypropyl)piperidin-2-one |
| 83 | (R)-1-((S)-1-(2',4'-difluorobiphenyl-4-yl)ethyl)-4-(4-fluorophenyl)-4-((R)-2-hydroxypropyl)piperidin-2-one |
| 84 | (R)-1-((S)-1-(2',4'-difluorobiphenyl-4-yl)ethyl)-4-(4-fluorophenyl)-4-(2-oxopropyl)piperidin-2-one |
| 85 | (R)-1-((S)-1-(2',4'-difluorobiphenyl-4-yl)ethyl)-4-(4-fluorophenyl)-4-(2-hydroxy-2-methylpropyl)piperidin-2-one |
| 86 | (R)-1-((S)-1-(2',4'-difluorobiphenyl-4-yl)ethyl)-4-(4-fluorophenyl)-4-(2-methoxyethyl)piperidin-2-one |
| 87 | 1-(2-((S)-1-((S)-1-(2',4'-difluorobiphenyl-4-yl)ethyl)-4-(4-fluorophenyl)-2-oxopiperidin-4-yl)ethyl)-3-methylurea |
| 88 | (R)-1-((S)-1-(4-bromophenyl)propyl)-4-(4-fluorophenyl)-4-(2-hydroxyethyl)piperidin-2-one |

| PROPHETIC COMPOUNDS | |
|---|---|
| Number | Compound Name |
| 89 | (R)-1-((S)-1-(4-bromophenyl)ethyl)-4-((S)-2,3-dihydroxypropyl)-4-(4-fluorophenyl)piperidin-2-one |
| 90 | (R)-1-((S)-1-(4-bromophenyl)ethyl)-4-((R)-2,3-dihydroxypropyl)-4-(4-fluorophenyl)piperidin-2-one |
| 91 | 3-((S)-1-((S)-1-(2',4'-difluorobiphenyl-4-yl)ethyl)-4-(4-fluorophenyl)-2-oxopiperidin-4-yl)propanamide |
| 92 | 3-((S)-1-((S)-1-(2',4'-difluorobiphenyl-4-yl)ethyl)-4-(4-fluorophenyl)-2-oxopiperidin-4-yl)-N-methylpropanamide |
| 93 | N-(2-((S)-1-((S)-1-(2',4'-difluorobiphenyl-4-yl)ethyl)-4-(4-fluorophenyl)-2-oxopiperidin-4-yl)ethyl)acetamide |
| 94 | 2-((R)-1-((S)-1-(2',4'-difluorobiphenyl-4-yl)ethyl)-4-(4-fluorophenyl)-2-oxopiperidin-4-yl)ethyl methylcarbamate |
| 95 | (S)-4-(2-(aminosulfonylamino)ethyl)-1-((S)-1-(2',4'-difluorobiphenyl-4-yl)ethyl)-4-(4-fluorophenyl)piperidin-2-one |
| 96 | (R)-1-((S)-1-(2',4'-difluorobiphenyl-4-yl)ethyl)-4-(4-fluorophenyl)-4-(2-(aminosulfonyloxy)ethyl)piperidin-2-one |
| 97 | 2-((R)-1-((S)-1-(2',4'-difluorobiphenyl-4-yl)ethyl)-4-(4-fluorophenyl)-2-oxopiperidin-4-yl)ethyl dihydrogen phosphate |
| 98 | 2-amino-N-(2-((S)-1-((S)-1-(2',4'-difluorobiphenyl-4-yl)ethyl)-4-(4-fluorophenyl)-2-oxopiperidin-4-yl)ethyl)acetamide |
| 99 | (S)-4-(4-fluorophenyl)-1-((S)-1-(4-(hydroxymethyl)phenyl)ethyl)-4-(3-hydroxypropyl)piperidin-2-one |
| 100 | (S)-4-allyl-4-(4-fluorophenyl)-1-((S)-1-(4-(2-hydroxypropan-2-yl)phenyl)ethyl)piperidin-2-one |
| 101 | (S)-4-allyl-1-((S)-1-(4-bromophenyl)ethyl)-4-(thiophen-2-yl)piperidin-2-one |
| 102 | (R)-4-allyl-1-((S)-1-(4-bromophenyl)ethyl)-4-(thiophen-2-yl)piperidin-2-one |
| 103 | (R)-1-((S)-1-(4'-fluorobiphenyl-4-yl)ethyl)-4-(2-hydroxyethyl)-4-phenylpiperidin-2-one |
| 104 | (R)-4-allyl-1-((S)-1-(4'-fluorobiphenyl-4-yl)ethyl)-4-(thiophen-2-yl)piperidin-2-one |
| 105 | (S)-4-allyl-1-((S)-1-(4'-fluorobiphenyl-4-yl)ethyl)-4-(thiophen-2-yl)piperidin-2-one |
| 106 | 4-allyl-1-((1S)-1-(4-bromophenyl)ethyl)-4-(4-fluorophenyl)-6-methylpiperidin-2-one |
| 107 | (S)-1-((S)-1-(4'-fluorobiphenyl-4-yl)ethyl)-4-(3-hydroxypropyl)-4-phenylpiperidin-2-one |
| 108 | 1-((1S)-1-(4-bromophenyl)ethyl)-4-(4-fluorophenyl)-4-(2-hydroxyethyl)-6-methylpiperidin-2-one |
| 109 | (R)-1-((1S)-1-(2',4'-difluorobiphenyl-4-yl)ethyl)-4-(2-hydroxyethyl)-4-phenylpiperidin-2-one |
| 110 | 4-allyl-1-((1S)-1-(2',4'-difluorobiphenyl-4-yl)ethyl)-4-(thiophen-2-yl)piperidin-2-one |
| 111 | 1-((1S)-1-(4'-fluorobiphenyl-4-yl)ethyl)-4-(3-hydroxypropyl)-4-(thiophen-2-yl)piperidin-2-one |
| 112 | 1-((1S)-1-(4'-fluorobiphenyl-4-yl)ethyl)-4-(2-hydroxyethyl)-4-(thiophen-2-yl)piperidin-2-one |
| 113 | (R)-4-((S)-2,3-dihydroxypropyl)-1-((S)-1-(4'-fluorobiphenyl-4-yl)ethyl)-4-phenylpiperidin-2-one |
| 114 | (R)-4-((R)-2,3-dihydroxypropyl)-1-((S)-1-(4'-fluorobiphenyl-4-yl)ethyl)-4-phenylpiperidin-2-one |
| 115 | (S)-1-((S)-1-(2',4'-difluorobiphenyl-4-yl)ethyl)-4-(3-hydroxypropyl)-4-phenylpiperidin-2-one |
| 116 | (4R)-1-((S)-1-(2',4'-difluorobiphenyl-4-yl)ethyl)-4-(2-hydroxypropyl)-4-phenylpiperidin-2-one |
| 117 | (S)-1-((S)-1-(2',4'-difluorobiphenyl-4-yl)ethyl)-4-(3-hydroxypropyl)-4-(thiophen-2-yl)piperidin-2-one |
| 118 | 3-((S)-1-((S)-1-(2',4'-difluorobiphenyl-4-yl)ethyl)-4-(4-fluorophenyl)-2-oxopiperidin-4-yl)propanenitrile |
| 119 | (R)-1-((S)-1-(2',4'-difluorobiphenyl-4-yl)ethyl)-4-((S)-2,3-dihydroxypropyl)-4-phenylpiperidin-2-one |
| 120 | (R)-1-((S)-1-(2',4'-difluorobiphenyl-4-yl)ethyl)-4-((R)-2,3-dihydroxypropyl)-4-phenylpiperidin-2-one |
| 121 | (R)-1-((S)-1-(2',4'-difluorobiphenyl-4-yl)propyl)-4-(4-fluorophenyl)-4-(2-hydroxyethyl)piperidin-2-one |
| 122 | 3-((S)-1-((S)-1-(2',4'-difluorobiphenyl-4-yl)ethyl)-4-(4-fluorophenyl)-2-oxopiperidin-4-yl)propanoic acid |
| 123 | (S)-1-((S)-1-(2',4'-difluorobiphenyl-4-yl)ethyl)-4-(4-fluorophenyl)-4-(2-(2-hydroxyethylamino)ethyl)piperidin-2-one |
| 124 | N-(2-((S)-1-((S)-1-(2',4'-difluorobiphenyl-4-yl)ethyl)-4-(4-fluorophenyl)-2-oxopiperidin-4-yl)ethyl)-2-hydroxyacetamide |
| 125 | methyl 2-((S)-1-((S)-1-(2',4'-difluorobiphenyl-4-yl)ethyl)-4-(4-fluorophenyl)-2-oxopiperidin-4-yl)ethylcarbamate |
| 126 | (S)-1-((S)-1-(2',4'-difluorobiphenyl-4-yl)ethyl)-4-(4-fluorophenyl)-4-(2-morpholinoethyl)piperidin-2-one |
| 127 | 1-(2-((S)-1-((S)-1-(2',4'-difluorobiphenyl-4-yl)ethyl)-4-(4-fluorophenyl)-2-oxopiperidin-4-yl)ethyl)-3-ethylurea |
| 128 | (Z)-2-cyano-1-(2-((S)-1-((S)-1-(2',4'-difluorobiphenyl-4-yl)ethyl)-4-(4-fluorophenyl)-2-oxopiperidin-4-yl)ethyl)-3-methylguanidine |
| 129 | N-(3-((S)-1-((S)-1-(2',4'-difluorobiphenyl-4-yl)ethyl)-4-(4-fluorophenyl)-2-oxopiperidin-4-yl)propyl)methanesulfonamide |
| 130 | 1-((1S)-1-(4-chlorophenyl)ethyl)-4-(3-hydroxypropyl)-4-isopropylpiperidin-2-one |
| 131 | (S)-4-allyl-4-(4-fluorophenyl)-1-((S)-1-p-tolylethyl)piperidin-2-one |
| 132 | (R)-4-allyl-4-(4-fluorophenyl)-1-((S)-1-p-tolylethyl)piperidin-2-one |
| 133 | (R)-4-(2-hydroxyethyl)-1-((S)-1-(4-methoxyphenyl)ethyl)-4-phenylpiperidin-2-one |
| 134 | (R)-6-allyl-6-(4-fluorophenyl)-3-((S)-1-(4-methoxyphenyl)ethyl)-1,3-oxazinan-2-one |
| 135 | (R)-4-allyl-4-(4-fluorophenyl)-1-((S)-1-(4-methoxyphenyl)ethyl)piperidin-2-one |
| 136 | (S)-1-((S)-1-(4-(hydroxymethyl)phenyl)ethyl)-4-(3-hydroxypropyl)-4-phenylpiperidin-2-one |
| 137 | (R)-4-(4-fluorophenyl)-4-(2-hydroxyethyl)-1-((S)-1-(4-methoxyphenyl)ethyl)piperidin-2-one |
| 138 | (S)-4-allyl-1-((S)-1-(4-chlorophenyl)ethyl)-4-(4-fluorophenyl)piperidin-2-one |
| 139 | (R)-4-allyl-1-((S)-1-(4-chlorophenyl)ethyl)-4-(4-fluorophenyl)piperidin-2-one |
| 140 | (R)-1-((S)-1-cyclohexylethyl)-4-((R)-2,3-dihydroxypropyl)-4-(4-fluorophenyl)piperidin-2-one |
| 141 | (R)-1-((S)-1-cyclohexylethyl)-4-((S)-2,3-dihydroxypropyl)-4-(4-fluorophenyl)piperidin-2-one |
| 142 | (S)-1-((S)-1-(4-(2-hydroxyethyl)phenyl)ethyl)-4-(3-hydroxypropyl)-4-phenylpiperidin-2-one |
| 143 | (S)-4-(3-hydroxypropyl)-1-((S)-1-(4-(methoxymethyl)phenyl)ethyl)-4-phenylpiperidin-2-one |
| 144 | 1-((1S)-1-(4-bromophenyl)ethyl)-4-(3-hydroxypropyl)-4-isopropylpiperidin-2-one |
| 145 | (S)-4-(4-fluorophenyl)-4-(3-hydroxypropyl)-1-((S)-1-(4-methoxyphenyl)ethyl)piperidin-2-one |
| 146 | (S)-1-((S)-1-(4-chlorophenyl)ethyl)-4-(4-fluorophenyl)-4-(3-hydroxypropyl)piperidin-2-one |
| 147 | (4R)-1-((S)-1-(4-chlorophenyl)ethyl)-4-(4-fluorophenyl)-4-(2-hydroxypropyl)piperidin-2-one |
| 148 | (R)-4-(2-hydroxyethyl)-4-phenyl-1-((S)-1-(4-(pyridin-3-yl)phenyl)ethyl)piperidin-2-one |
| 149 | (R)-4-((R)-2,3-dihydroxypropyl)-4-(4-fluorophenyl)-1-((S)-1-(4-methoxyphenyl)ethyl)piperidin-2-one |
| 150 | (R)-4-((S)-2,3-dihydroxypropyl)-4-(4-fluorophenyl)-1-((S)-1-(4-methoxyphenyl)ethyl)piperidin-2-one |
| 151 | (S)-1-((S)-1-(2',4'-difluorobiphenyl-4-yl)ethyl)-4-(2-hydroxyethyl)-4-isopropylpiperidin-2-one |
| 152 | (R)-1-((S)-1-(2',4'-difluorobiphenyl-4-yl)ethyl)-4-(2-hydroxyethyl)-4-isopropylpiperidin-2-one |
| 153 | (S)-tert-butyl 3-((S)-4-(3-hydroxypropyl)-2-oxo-4-phenylpiperidin-1-yl)pyrrolidine-1-carboxylate |
| 154 | N-(2-((S)-3-((S)-1-(2',4'-difluorobiphenyl-4-yl)ethyl)-6-(4-fluorophenyl)-2-oxo-1,3-oxazinan-6-yl)ethyl)methanesulfonamide |
| 155 | (S)-4-(3-hydroxypropyl)-4-phenyl-1-((S)-1-(4-(pyridin-4-yl)phenyl)ethyl)piperidin-2-one |
| 156 | (S)-4-(3-hydroxypropyl)-4-phenyl-1-((S)-1-(4-(pyridin-3-yl)phenyl)ethyl)piperidin-2-one |
| 157 Isomer 1 | (R)-1-((S)-1-(2',4'-difluorobiphenyl-4-yl)ethyl)-4-(3-hydroxypropyl)-4-isopropylpiperidin-2-one |
| 157 Isomer 2 | (S)-1-((S)-1-(2',4'-difluorobiphenyl-4-yl)ethyl)-4-(3-hydroxypropyl)-4-isopropylpiperidin-2-one |
| 158 | (R)-4-(4-fluorophenyl)-4-(2-hydroxyethyl)-1-((S)-1-(4-(pyridin-3-yl)phenyl)ethyl)piperidin-2-one |
| 159 | (S)-4-(3-hydroxypropyl)-4-phenyl-1-((S)-1-(4-(thiophen-2-yl)phenyl)ethyl)piperidin-2-one |
| 160 | (S)-4-allyl-4-(4-fluorophenyl)-1-((S)-1-(4-morpholinophenyl)ethyl)piperidin-2-one |

| Number | Compound Name |
| --- | --- |
| 161 | (R)-1-((S)-1-(4'-fluorobiphenyl-4-yl)ethyl)-4-(2-hydroxyethyl)-4-(thiophen-2-yl)piperidin-2-one |
| 162 | 3-((S)-1-((S)-1-(4'-fluorobiphenyl-4-yl)ethyl)-2-oxo-4-phenylpiperidin-4-yl)propanenitrile |
| 163 | (S)-1-((S)-1-(4-bromophenyl)propyl)-4-(3-hydroxypropyl)-4-phenylpiperidin-2-one |
| 164 | 5-(4-((S)-1-((S)-4-(3-hydroxypropyl)-2-oxo-4-phenylpiperidin-1-yl)ethyl)phenyl)pyridin-2(1H)-one |
| 165 | 3-(4-((S)-1-((S)-4-(3-hydroxypropyl)-2-oxo-4-phenylpiperidin-1-yl)ethyl)phenyl)pyridine 1-oxide |
| 166 | 1-((1S)-1-(2',4'-difluorobiphenyl-4-yl)ethyl)-4-((S)-2,3-dihydroxypropyl)-4-isopropylpiperidin-2-one |
| 167 | 1-((1S)-1-(2',4'-difluorobiphenyl-4-yl)ethyl)-4-((R)-2,3-dihydroxypropyl)-4-isopropylpiperidin-2-one |
| 168 | (4R)-1-((S)-1-(4'-fluorobiphenyl-4-yl)ethyl)-4-(2-hydroxypropyl)-4-phenylpiperidin-2-one |
| 169 | (R)-1-((S)-1-(4'-fluorobiphenyl-4-yl)ethyl)-4-((R)-2-hydroxypropyl)-4-phenylpiperidin-2-one |
| 170 | (R)-1-((S)-1-(4'-fluorobiphenyl-4-yl)ethyl)-4-((S)-2-hydroxypropyl)-4-phenylpiperidin-2-one |
| 171 | (S)-4-(4-fluorophenyl)-4-(3-hydroxypropyl)-1-((S)-1-(4-(pyridin-3-yl)phenyl)ethyl)piperidin-2-one |
| 172 | (S)-1-((S)-1-(2',4'-difluorobiphenyl-4-yl)ethyl)-4-phenyl-4-propylpiperidin-2-one |
| 173 | (S)-1-((S)-1-(4-bromophenyl)ethyl)-4-(4-fluorophenyl)-4-(3-hydroxypropyl)piperidin-2-one |
| 174 | (S)-1-((S)-1-(2',4'-difluorobiphenyl-4-yl)ethyl)-4-(4-fluorophenyl)-4-(2-(methylsulfonyl)ethyl)piperidin-2-one |
| 175 | (S)-4-allyl-4-(4-fluorophenyl)-1-((S)-1-(4-(5-methyl-1,3,4-thiadiazol-2-yl)phenyl)ethyl)piperidin-2-one |
| 176 | (S)-1-((S)-1-(4'-fluorobiphenyl-4-yl)ethyl)-4-(3-hydroxypropyl)-4-(thiophen-2-yl)piperidin-2-one |
| 177 | (R)-1-((S)-1-(2',4'-difluorobiphenyl-4-yl)ethyl)-4-(2-hydroxyethyl)-4-(thiophen-2-yl)piperidin-2-one |
| 178 | 3-((S)-1-((S)-1-(4'-fluorobiphenyl-4-yl)ethyl)-2-oxo-4-phenylpiperidin-4-yl)propanamide |
| 179 | (S)-4-(3-hydroxypropyl)-1-((S)-1-(4-(6-methoxypyridin-3-yl)phenyl)ethyl)-4-phenylpiperidin-2-one |
| 180 | 3-((S)-4-(4-fluorophenyl)-2-oxo-1-((S)-1-(4-(pyridin-3-yl)phenyl)ethyl)piperidin-4-yl)propanamide |
| 181 | (S)-1-((S)-1-(4'-fluorobiphenyl-4-yl)propyl)-4-(3-hydroxypropyl)-4-phenylpiperidin-2-one |
| 182 | (R)-1-((S)-1-(4'-fluorobiphenyl-4-yl)ethyl)-4-(2-hydroxy-2-methylpropyl)-4-phenylpiperidin-2-one |
| 183 Isomer 1 | (R)-1-((S)-1-(4-bromophenyl)propyl)-4-((S)-2,3-dihydroxypropyl)-4-phenylpiperidin-2-one |
| 183 Isomer 2 | (R)-1-((S)-1-(4-bromophenyl)propyl)-4-((R)-2,3-dihydroxypropyl)-4-phenylpiperidin-2-one |
| 184 | 3-((S)-1-((S)-1-(4-bromophenyl)ethyl)-4-(4-fluorophenyl)-2-oxopiperidin-4-yl)propanamide |
| 185 | (S)-1-((S)-1-(4-bromophenyl)propyl)-4-(4-fluorophenyl)-4-(3-hydroxypropyl)piperidin-2-one |
| 186 | 2-((R)-1-((S)-1-(2',4'-difluorobiphenyl-4-yl)ethyl)-4-(4-fluorophenyl)-2-oxopiperidin-4-yl)acetonitrile |
| 187 | (S)-4-allyl-1-((S)-1-(4-(2,4-dimethylthiazol-5-yl)phenyl)ethyl)-4-(4-fluorophenyl)piperidin-2-one |
| 188 | (S)-1-((S)-1-(4'-fluorobiphenyl-4-yl)ethyl)-4-(4-fluorophenyl)-4-(3-hydroxypropyl)piperidin-2-one |
| 189 | (S)-1-((S)-1-(4'-fluorobiphenyl-4-yl)ethyl)-4-(2-fluorophenyl)-4-(3-hydroxypropyl)piperidin-2-one |
| 190 | (R)-1-((S)-1-(4'-fluorobiphenyl-4-yl)ethyl)-4-(2-fluorophenyl)-4-(3-hydroxypropyl)piperidin-2-one |
| 191 | (S)-1-((S)-1-(4'-fluorobiphenyl-4-yl)ethyl)-4-(3-fluorophenyl)-4-(3-hydroxypropyl)piperidin-2-one |
| 192 | (S)-1-((S)-1-(4'-fluorobiphenyl-4-yl)ethyl)-4-(3-hydroxy-3-methylbutyl)-4-phenylpiperidin-2-one |
| 193 | (S)-1-((S)-1-(4-(5-acetylthiophen-2-yl)phenyl)ethyl)-4-(3-hydroxypropyl)-4-phenylpiperidin-2-one |
| 194 | 3-((S)-1-((S)-1-(2',4'-difluorobiphenyl-4-yl)ethyl)-2-oxo-4-phenylpiperidin-4-yl)propanamide |
| 195 | (4S)-(S)-1-((1S)-1-(4-(5-(1-aminoethyl)thiophen-2-yl)phenyl)ethyl)-4-(3-hydroxypropyl)-4-phenylpiperidin-2-one |
| 196 | (S)-1-((S)-1-(4'-fluorobiphenyl-4-yl)propyl)-4-(4-fluorophenyl)-4-(3-hydroxypropyl)piperidin-2-one |
| 197 | (S)-1-((S)-1-(2',4'-difluorobiphenyl-4-yl)propyl)-4-(3-hydroxypropyl)-4-phenylpiperidin-2-one |
| 198 | (4S)-1-((1S)-1-(4-(5-(1-hydroxyethyl)thiophen-2-yl)phenyl)ethyl)-4-(3-hydroxypropyl)-4-phenylpiperidin-2-one |
| 199 | (R)-1-((S)-1-(4-bromophenyl)propyl)-4-((R)-2,3-dihydroxypropyl)-4-(4-fluorophenyl)piperidin-2-one |
| 200 | (R)-1-((S)-1-(4-bromophenyl)propyl)-4-((S)-2,3-dihydroxypropyl)-4-(4-fluorophenyl)piperidin-2-one |
| 201 | (S)-4-(3-aminopropyl)-1-((S)-1-(2',4'-difluorobiphenyl-4-yl)ethyl)-4-(4-fluorophenyl)piperidin-2-one |
| 202 | (S)-1-((S)-1-(2',4'-difluorobiphenyl-4-yl)ethyl)-4-(4-fluorophenyl)-4-(2-(methylamino)ethyl)piperidin-2-one |
| 203 | (S)-4-allyl-4-(4-fluorophenyl)-1-((S)-1-(4-(3-(trifluoromethyl)-1H-pyrazol-1-yl)phenyl)ethyl)piperidin-2-one |
| 204 | (S)-1-((S)-1-(2',4'-difluorobiphenyl-4-yl)ethyl)-4-(3-hydroxy-3-methylbutyl)-4-phenylpiperidin-2-one |
| 205 | (S)-1-((S)-1-(2',4'-difluorobiphenyl-4-yl)propyl)-4-(4-fluorophenyl)-4-(3-hydroxypropyl)piperidin-2-one |
| 206 | (S)-1-((S)-1-(2',4'-difluorobiphenyl-4-yl)ethyl)-4-(4-fluorophenyl)-4-(2-(methylthio)ethyl)piperidin-2-one |
| 207 | 1-(2-((S)-1-((S)-1-(2',4'-difluorobiphenyl-4-yl)ethyl)-4-(4-fluorophenyl)-2-oxopiperidin-4-yl)ethyl)urea |
| 208 | 2-((R)-1-((S)-1-(2',4'-difluorobiphenyl-4-yl)ethyl)-4-(4-fluorophenyl)-2-oxopiperidin-4-yl)ethyl carbamate |
| 209 | (R)-1-((S)-1-(2',4'-difluorobiphenyl-4-yl)ethyl)-4-(4-fluorophenyl)-4-(2-(2-hydroxyethoxy)ethyl)piperidin-2-one |
| 210 | (R)-4-(2-(1H-imidazol-1-yl)ethyl)-1-((S)-1-(2',4'-difluorobiphenyl-4-yl)ethyl)-4-(4-fluorophenyl)piperidin-2-one |
| 211 | N-(2-((R)-3-((S)-1-(2',4'-difluorobiphenyl-4-yl)ethyl)-6-(4-fluorophenyl)-2-oxo-1,3-oxazinan-6-yl)ethyl)-N-methylacetamide |
| 212 | N-(3-((S)-1-((S)-1-(4'-fluorobiphenyl-4-yl)ethyl)-2-oxo-4-phenylpiperidin-4-yl)propyl)methanesulfonamide |
| 213 | 1-(3-((S)-1-((S)-1-(2',4'-difluorobiphenyl-4-yl)ethyl)-4-(4-fluorophenyl)-2-oxopiperidin-4-yl)propyl)urea |
| 214 | 3-((S)-1-((S)-1-(2',4'-difluorobiphenyl-4-yl)ethyl)-4-(4-fluorophenyl)-2-oxopiperidin-4-yl)propyl carbamate |
| 215 | 4-(2-(2-amino-1H-imidazol-1-yl)ethyl)-1-(1-(2',4'-difluorobiphenyl-4-yl)ethyl)-4-(4-fluorophenyl)piperidin-2-one |
| 216 | 1-(3-((S)-1-((S)-1-(2',4'-difluorobiphenyl-4-yl)ethyl)-4-(4-fluorophenyl)-2-oxopiperidin-4-yl)propyl)-3-methylurea |
| 217 | 1-(3-((R)-1-((S)-1-(2',4'-difluorobiphenyl-4-yl)ethyl)-4-(4-fluorophenyl)-2-oxopiperidin-4-yl)-2-hydroxypropyl)urea |
| 218 | N-(3-((R)-1-((S)-1-(4'-fluorobiphenyl-4-yl)ethyl)-4-(4-fluorophenyl)-2-oxopiperidin-4-yl)-2-hydroxypropyl)methanesulfonamide |
| 219 | N-((R)-3-((R)-1-((S)-1-(4'-fluorobiphenyl-4-yl)ethyl)-4-(4-fluorophenyl)-2-oxopiperidin-4-yl)-2-hydroxypropyl)-N-methylmethanesulfonamide |
| 220 | (S)-4-(4-fluorophenyl)-4-(3-hydroxypropyl)-1-((S)-1-(4-(6-(trifluoromethyl)pyridin-3-yl)phenyl)ethyl)piperidin-2-one |
| 221 | (S)-4-(3-hydroxypropyl)-1-((S)-1-(4-methoxyphenyl)ethyl)-4-phenylpiperidin-2-one |
| 222 | (S)-4-(4-fluorophenyl)-1-((S)-1-(3-fluorophenyl)ethyl)-4-(3-hydroxypropyl)piperidin-2-one |
| 223 | (S)-4-(4-fluorophenyl)-1-((S)-1-(2-fluorophenyl)ethyl)-4-(3-hydroxypropyl)piperidin-2-one |
| 224 | (S)-4-(4-fluorophenyl)-1-((S)-1-(4-fluorophenyl)ethyl)-4-(3-hydroxypropyl)piperidin-2-one |
| 225 | (R)-4-((S)-2,3-dihydroxypropyl)-1-((S)-1-(4-methoxyphenyl)ethyl)-4-phenylpiperidin-2-one |
| 226 | (R)-4-((R)-2,3-dihydroxypropyl)-1-((S)-1-(4-methoxyphenyl)ethyl)-4-phenylpiperidin-2-one |
| 227 | 3-((S)-1-((S)-1-(4-chlorophenyl)ethyl)-2-oxo-4-phenylpiperidin-4-yl)propanamide |
| 228 | 3-((S)-4-(4-fluorophenyl)-1-((S)-1-(4-methoxyphenyl)ethyl)-2-oxopiperidin-4-yl)propanamide |
| 229 | (S)-4-allyl-1-((S)-1-(4-(difluoromethoxy)phenyl)ethyl)-4-(4-fluorophenyl)piperidin-2-one |
| 230 | (S)-1-((S)-1-(4-(1H-pyrazol-3-yl)phenyl)ethyl)-4-(3-hydroxypropyl)-4-phenylpiperidin-2-one |
| 231 | (S)-4-allyl-1-((S)-1-(4-(5-fluoropyridin-3-yl)phenyl)ethyl)-4-phenylpiperidin-2-one |
| 232 | (S)-4-(4-fluorophenyl)-4-(3-hydroxypropyl)-1-((S)-1-(3-(trifluoromethyl)phenyl)ethyl)piperidin-2-one |
| 233 | (S)-4-(4-fluorophenyl)-4-(3-hydroxypropyl)-1-((S)-1-(4-(trifluoromethyl)phenyl)ethyl)piperidin-2-one |

PROPHETIC COMPOUNDS

| Number | Compound Name |
|---|---|
| 234 | 3-((S)-2-oxo-4-phenyl-1-((S)-1-(4-(pyridin-3-yl)phenyl)ethyl)piperidin-4-yl)propanamide |
| 235 | 3-((S)-2-oxo-4-phenyl-1-((S)-1-(4-(pyridin-4-yl)phenyl)ethyl)piperidin-4-yl)propanamide |
| 236 | (R)-1-((S)-1-(4'-fluorobiphenyl-4-yl)ethyl)-4-(3-hydroxypropyl)-4-phenylpiperidin-2-one |
| 237 | (S)-1-((S)-1-(4-(5-fluoropyridin-3-yl)phenyl)ethyl)-4-(3-hydroxypropyl)-4-phenylpiperidin-2-one |
| 238 | N-(2-((R)-4-(4-fluorophenyl)-1-((S)-1-(4-methoxyphenyl)ethyl)-2-oxopiperidin-4-yl)ethyl)methanesulfonamide |
| 239 | (S)-4-(4-fluorophenyl)-1-((S)-1-(4-(5-fluoropyridin-3-yl)phenyl)ethyl)-4-(3-hydroxypropyl)piperidin-2-one |
| 240 | 3-((S)-1-((S)-1-(4'-fluorobiphenyl-4-yl)ethyl)-2-oxo-4-phenylpiperidin-4-yl)-2,2-dimethylpropanenitrile |
| 241 | 3-((S)-1-((S)-1-(4-(6-methoxypyridin-3-yl)phenyl)ethyl)-2-oxo-4-phenylpiperidin-4-yl)propanamide |
| 242 | (S)-4-(4-fluorophenyl)-4-(3-hydroxypropyl)-1-((S)-1-(4-(5-methoxypyridin-3-yl)phenyl)ethyl)piperidin-2-one |
| 243 | (S)-1-((S)-1-(4-(5-chloropyridin-3-yl)phenyl)ethyl)-4-(4-fluorophenyl)-4-(3-hydroxypropyl)piperidin-2-one |
| 244 | N-(2-((R)-2-oxo-4-phenyl-1-((S)-1-(4-(pyridin-3-yl)phenyl)ethyl)piperidin-4-yl)ethyl)methanesulfonamide |
| 245 | (S)-1-((S)-1-(4-(difluoromethoxy)phenyl)ethyl)-4-(4-fluorophenyl)-4-(3-hydroxypropyl)piperidin-2-one |
| 246 | 3-((S)-1-((S)-1-(4'-fluorobiphenyl-4-yl)ethyl)-2-oxo-4-phenylpiperidin-4-yl)propyl dihydrogen phosphate |
| 247 | (S)-4-(4-fluorophenyl)-4-(3-hydroxypropyl)-1-((S)-1-(4-(2-methylpyridin-4-yl)phenyl)ethyl)piperidin-2-one |
| 248 | (S)-1-((S)-1-(4-(2-hydroxy-2-methylpropyl)phenyl)ethyl)-4-(3-hydroxypropyl)-4-phenylpiperidin-2-one |
| 249 | 5-(4-((S)-1-((S)-4-(3-hydroxypropyl)-2-oxo-4-phenylpiperidin-1-yl)ethyl)phenyl)-1-methylpyridin-2(1H)-one |
| 250 | N-(3-((S)-4-(4-fluorophenyl)-1-((S)-1-(4-methoxyphenyl)ethyl)-2-oxopiperidin-4-yl)propyl)methanesulfonamide |
| 251 | 3-((S)-1-((S)-1-(4-methoxyphenyl)ethyl)-2-oxo-4-phenylpiperidin-4-yl)propanamide |
| 252 | 3-((S)-4-(4-fluorophenyl)-1-((S)-1-(4-fluorophenyl)ethyl)-2-oxopiperidin-4-yl)propanamide |
| 253 | 3-((S)-1-((S)-1-cyclohexylethyl)-4-(4-fluorophenyl)-2-oxopiperidin-4-yl)propanamide |
| 254 | N-(2-((R)-1-((S)-1-cyclohexylethyl)-4-(4-fluorophenyl)-2-oxopiperidin-4-yl)ethyl)methanesulfonamide |
| 255 | N-(3-((S)-1-((S)-1-cyclohexylethyl)-4-(4-fluorophenyl)-2-oxopiperidin-4-yl)propyl)methanesulfonamide |

The compounds of the invention are useful for ameliorating or treating disorders or diseases in which decreasing the level of cortisol is effective in treating a disease state. Thus, the compounds of the invention can be used in the treatment or prevention of diabetes mellitus, obesity (especially abdominal obesity), symptoms of metabolic syndrome, prothrombotic state, proinflammatory state, glucose intolerance, hyperglycemica, hypertension, hyperlipidemia, insulin resistance, cardiovascular disease, dyslipidemia, atherosclerosis, lipodystrophy, osteoporosis, glaucoma, Cushing's syndrome, Addison's Disease, visceral fat obesity associated with glucocorticoid therapy, depression, anxiety, Alzheimer's disease, dementia, cognitive decline (including age-related cognitive decline), polycystic ovarian syndrome, infertility and hypergonadism. The compounds of the invention can be used as therapeutic agents for pseudo Cushing's Syndrome associated with alcoholic liver disease. In addition, the compounds modulate the function of B and T cells of the immune system and can therefore be used to treat diseases such as tuberculosis, leprosy and psoriasis. They can also be used to promote wound healing, particularly in diabetic patients.

Additional diseases or disorders that are related to 11β-HSD1 activity include those selected from the group consisting of lipid disorders, hypretriglyceridemia, hypercholesterolemia, low HDL levels, high LDL levels, vascular restenosis, pancreatitis, abdominal obesity, neurodegenerative disease, retinopathy, nephropathy, neuropathy, diabetes, coronary heart disease, stroke, peripheral vascular disease, Cushing's syndrome, hyperinsulinemia, viral diseases, and Syndrome X. A further disease related to 11β-HSD1 activity is pseudo Cushing's Syndrome associated with alcoholic liver disease. Alternatively, a pharmaceutical composition of the invention may comprise a compound of Formula I, Ia-s$^2$ or a pharmaceutical salt thereof as the only pharmaceutically active agent in the pharmaceutical composition. The disclosed 11β-HSD1 inhibitors can be used alone or in a combination therapy with one or more additional agents for the treatment of diabetes, dyslipidemia, cardiovascular disease, hypertension, obesity, cancer or glaucoma. A pharmaceutical composition of the invention may, alternatively or in addition to a compound of Formula I, comprise a pharmaceutically acceptable salt of a compound of Formula I or a prodrug or pharmaceutically active metabolite of such a compound or salt and one or more pharmaceutically acceptable carriers therefore. Alternatively, a pharmaceutical composition of the invention may comprise a compound of the invention or a pharmaceutical salt thereof as the only pharmaceutically active agent in the pharmaceutical composition. The disclosed 11β-HSD1 inhibitors can be used alone or in a combination therapy with one or more additional agents for the treatment of diabetes, dyslipidemia, cardiovascular disease, hypertension, obesity, cancer or glaucoma.

The compositions of the invention are 11β-HSD1 inhibitors. Said compositions contain compounds having a mean inhibition constant ($IC_{50}$) against 11β-HSD1 of below about 1,000 nM; preferably below about 100 nM; more preferably below about 50 nM; even more preferably below about 5 nM; and most preferably below about 1 nM.

The invention includes a therapeutic method for treating or ameliorating an 11β-HSD1 mediated disorder in a subject in need thereof comprising administering to a subject in need thereof an effective amount of a compound of Formula I, or an enantiomer, diastereomer, or pharmaceutically acceptable salt thereof of composition thereof. As used herein, "treating" or "treatment" includes both therapeutic and prophylactic treatment. Therapeutic treatment includes reducing the symptoms associated with a disease or condition and/or increasing the longevity of a subject with the disease or condition. Prophylactic treatment includes delaying the onset of a disease or condition in a subject at risk of developing the disease or condition or reducing the likelihood that a subject will then develop the disease or condition in a subject that is at risk for developing the disease or condition.

An embodiment of the invention includes administering an 11β-HSD1 inhibiting compound of Formula I or composition thereof in a combination therapy with one or more additional agents for the treatment of diabetes, dyslipidemia, cardiovascular disease, hypertension, obesity, cancer or glaucoma. Agents for the treatment of diabetes include insulins, such as Humulin® (Eli Lilly), Lantus® (Sanofi Aventis), Novolin (Novo Nordisk), and Exubera® (Pfizer); PPAR gamma agonists, such as Avandia® (rosiglitizone maleate, GSK) and Actos® (pioglitazone hydrochloride, Takeda/Eli Lilly); sulfonylureas, such as Amaryl® (glimepiride, Sanofi Aventis), Diabeta® (glyburide, Sanofi Aventis), Micronase®/Glynase® (glyburide, Pfizer), and Glucotrol®/Glucotrol XL® and (glipizide, Pfizer); meglitinides, such as Prandin®/NovoNorm® (repaglinide, Novo Nordisk), Starlix® (nateglinide, Novartis), and Glufast® (mitiglinide, Takeda); biguanides, such as Glucophase®/Glucophase XR® (metformin HCl, Bristol Myers Squibb) and Glumetza (metformin HCl, Depomed); thiazolidinediones; amylin analogs, GLP-1 analogs; DPP-IV inhibitors; PTB-1B inhibitors; protein kinase inhibitors (including AMP-activated protein kinase inhibitors); glucagon antagonists, glycogen synthase kinase-3 beta inhibitors; glucose-6-phoshatase inhibitors; glycogen phosphorylase inhibitors; sodium glucose co-transporter inhibitors, and alpha-glucosidase inhibitors, such as Precose®/Glucobay®/Prandase®/Glucor® (acarbose, Bayer) and Glyset® (miglitol, Pfizer). Agents for the treatment of dyslipidemia and cardiovascular disease include statins, fibrates, and ezetimbe. Agents for the treatment of hypertension include alpha-blockers, beta-blockers, calcium channel blockers, diuretics, angiotensin converting enzyme (ACE) inhibitors, dual ACE and neutral endopeptidase (NEP) inhibitors, angiotensin-receptor blockers (ARBs), aldosterone synthase inhibitor, aldosterone-receptor antagonists, or endothelin receptor antagonist. Agents for the treatment of obesity include orlistat, phentermine, sibutramine and rimonabant.

An embodiment of the invention includes administering an 11β-HSD1 inhibiting compound of Formula I or composition thereof in a combination therapy with one or more other 11β-HSD1 inhibitors (whether such inhibitors are also compounds of Formula I or are compounds of a different class/genus), or with combination products, such as Avandamet® (metformin HCl and rosiglitazone maleate, GSK); Avandaryl® (glimepiride and rosiglitazone maleate, GSK); Metaglip® (glipizide and metformin HCl, Bristol Myers Squibb); and Glucovance® (glyburide and metformin HCl, Bristol Myers Squibb).

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Additionally, the compounds of the present invention can be administered intranasally or transdermally. It will be obvious to those skilled in the art that the following dosage forms may comprise as the active ingredient, either compounds or a corresponding pharmaceutically acceptable salt of a compound of the present invention.

For preparing pharmaceutical compositions from the compounds of the present invention, pharmaceutically acceptable carriers can either be solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is in a mixture with the finely divided active ingredient.

In tablets, the active ingredient is mixed with the carrier having the necessary binding properties in suitable proportions and compacted in the shape and size desired.

The powders and tablets preferably contain from about one to about seventy percent of the active ingredient. Suitable carriers are magnesium carbonate, magnesium stearate, talc, sugar, lactose, pectin, dextrin, starch, gelatin, tragacanth, methylcellulose, sodium caboxymethylcellulose, a low-melting wax, cocoa butter, and the like. Tablets, powders, cachets, lozenges, fast-melt strips, capsules and pills can be used as solid dosage forms containing the active ingredient suitable for oral administration.

For preparing suppositories, a low-melting wax, such as a mixture of fatty acid glycerides or cocoa butter, is first-melted and the active ingredient is dispersed homogeneously therein, as by stirring. The molten homogeneous mixture is then poured into convenient sized molds, allowed to cool, and thereby to solidify.

Liquid form preparations include solutions, suspensions, retention enemas, and emulsions, for example, water or water propylene glycol solutions. For parenteral injection, liquid preparations can be formulated in solution in aqueous polyethylene glycol solution.

Aqueous solutions suitable for oral administration can be prepared by dissolving the active ingredient in water and adding suitable colorants, flavors, stabilizing, and thickening agents as desired. Aqueous suspensions for oral administration can be prepared by dispersing the finely divided active ingredient in water with viscous material, such as natural or synthetic gums, resins, methylcellulose, sodium carboxymethylcellulose, and other well-known suspending agents.

The pharmaceutical composition is preferably in unit dosage form. In such form, the composition is subdivided into unit doses containing appropriate quantities of the active ingredient. The unit dosage form can be a packaged preparation, the package containing discrete quantities of, for example, tablets, powders, and capsules in vials or ampules. Also, the unit dosage form can be a tablet, cachet, capsule, or lozenge itself, or it can be the appropriate amount of any of these in packaged form.

The quantity of active ingredient in a unit dose preparation may be varied or adjusted from about 0.1 mg to about 1000.0 mg, preferably from about 0.1 mg to about 100 mg. The dosages, however, may be varied depending upon the requirements of the patient, the severity of the condition being treated, and the compound being employed. Determination of the proper dosage for a particular situation is within the skill in the art. Also, the pharmaceutical composition may contain, if desired, other compatible therapeutic agents.

In therapeutic treatment or as a method-of-use as an inhibitor of 11β-HSD1 or an inhibitor in the production of cortisol in the cell, the active ingredient is preferably administered orally in a solid dosage form as disclosed above in an amount of about 0.1 mg to about 100 mg per daily dose where the dose is administered once or more than once daily.

All publications, patents and patent applications mentioned in this specification are herein incorporated by reference to the same extent as if each individual publication or patent application were specifically and individually designated as having been incorporated by reference. It is understood that the examples and embodiments described herein are for illustrative purposes only, and it will be appreciated that the invention is susceptible to modification, variation and change without departing from the proper scope or fair meaning of the appended claims.

What is claimed is:

1. A compound of Formula (I):

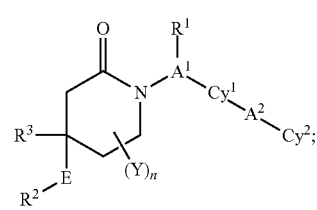

wherein:
R$^1$ is (a) absent or (b) is selected from (C$_1$-C$_6$)alkyl, (C$_2$-C$_6$)alkenyl, (C$_2$-C$_6$)alkynyl, (C$_1$-C$_3$)alkoxy(C$_1$-C$_3$)alkoxy, and (C$_1$-C$_3$)alkoxy(C$_1$-C$_3$)alkyl, each of which is optionally substituted with up to four groups independently selected from fluorine, cyano, oxo, R$^4$, R$^4$O—, $(R^4)_2N-$, $R^4O_2C-$, $R^4S$, $R^4S(=O)-$, $R^4S(=O)_2-$, $R^4C(=O)NR^4-$, $(R^4)_2NC(=O)-$, $(R^4)_2NC(=O)O-$, $(R^4)_2NC(=O)NR^4-$, $R^4OC(=O)NR^4-$, $(R^4)_2NC(=NCN)NR^4-$, $(R^4O)_2P(=O)O-$, $(R^4O)_2P(=O)NR^4-$, $R^4OS(=O)_2NR^4-$, $(R^4)_2NS(=O)_2O-$, $(R^4)_2NS(=O)_2NR^4-$, $R^4S(=O)_2NR^4-$, $R^4S(=O)_2NHC(=O)-$, $R^4S(=O)_2NHC(=O)O-$, $R^4S(=O)_2NHC(=O)NR^4-$, $R^4OS(=O)_2NHC(=O)-$, $R^4OS(=O)_2NHC(=O)O-$, $R^4OS(=O)_2NHC(=O)NR^4-$, $(R^4)_2NS(=O)_2NHC(=O)-$, $(R^4)_2NS(=O)_2NHC(=O)O-$, $(R^4)_2NS(=O)_2NHC(=O)NR^4-$, $R^4C(=O)NHS(=O)_2-$, $R^4C(=O)NHS(=O)_2O-$, $R^4C(=O)NHS(=O)_2NR^4-$, $R^4OC(=O)NHS(=O)_2-$, $R^4OC(=O)NHS(=O)_2O-$, $R^4OC(=O)NHS(=O)_2NR^4-$, $(R^4)_2NC(=O)NHS(=O)_2-$, $(R^4)_2NC(=O)NHS(=O)_2O-$, $(R^4)_2NC(=O)NHS(=O)_2NR^4-$, aryl, cycloalkyl, heterocyclyl, heteroaryl, arylamino and heteroarylamino;

$A^1$ is (a) a bond, or (b) $(C_1-C_3)$alkylene, $CH_2CH_2O$, wherein the oxygen is attached to $Cy^1$, or $CH_2C(=O)$, wherein the carbonyl carbon is attached to $Cy^1$;

$Cy^1$ is aryl, heteroaryl, monocyclic cycloalkyl or monocyclic heterocyclyl, each of which is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl, $(C_1-C_6)$alkylamino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, $\{(C_3-C_6)$cycloalkyl$\}\{(C_1-C_6)$alkyl$\}$aminocarbonyl, di$(C_3-C_6)$cycloalkylaminocarbonyl, $(C_3-C_6)$cycloalkylaminosulfonyl, $\{(C_3-C_6)$cycloalkyl$\}\{(C_1-C_6)$alkyl$\}$amino sulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, $\{(C_3-C_6)$cycloalkyl$\}\{(C_1-C_6)$alkyl$\}$aminocarbonyl$(C_1-C_6)$alkyl and di$(C_3-C_6)$cycloalkylaminocarbonyl$(C_1-C_6)$alkyl;

$A^2$ is (a) a bond, O, S or $NR^4$; or (b) $(C_1-C_3)$alkylene or $(C_1-C_2)$alkyleneoxy, each of which is optionally substituted with 1 to 4 groups independently selected from methyl, ethyl, trifluoromethyl and oxo;

$Cy^2$ is aryl, cycloalkyl, a heteroaryl selected from 2- or 3-thienyl, 2- or 3-furanyl, 2- or 3-pyrrolyl, 2-,3-, or 4-pyridyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, 5-, 6-, 7- or 8-quinazolinyl, 2-, 3-, 5-, 6-, 7- or 8-quinoxalinyl, 2-, 3-, 4-, 5-, 6-, 7- or 8-quinolinyl, 1-, 3-, 4-, 5-, 6-, 7- or 8-isoquinolinyl, 2-, 4-, or 5-thiazolyl, 2-, 3-, 4-, and 5-imidazolyl, or a heterocyclyl selected from pyrrolidine, pyrrolidin-2-one, 1-methylpyrrolidin-2-one, piperidine, piperidin-2-one, 2-pyridone, 4-pyridone, 1-(2,2,2-trifluoroethyl)piperazine, piperazin-2-one, 5,6-dihydropyrimidin-4-one, pyrimidin-4-one, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide and isothiazolidine 1,1-dioxide, wherein the aryl, cycloalkyl or heterocyclyl represented by $Cy^2$ are optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$ alkylamino($C_1$-$C_6$)alkyl, di($C_1$-$C_6$)alkylamino($C_1$-$C_6$) alkylamino($C_2$-$C_6$)alkoxy, ($C_1$-$C_6$)alkylamino($C_2$-$C_6$) alkoxy, di($C_1$-$C_6$)alkylamino($C_2$-$C_6$)alkoxy, ($C_1$-$C_6$) alkylcarbonyl, ($C_3$-$C_6$)cycloalkylcarbonyl, ($C_3$-$C_6$) cycloalkylaminocarbonyl, {($C_3$-$C_6$)cycloalkyl}{($C_1$-$C_6$)alkyl}aminocarbonyl, di($C_3$-$C_6$) cycloalkylaminocarbonyl, ($C_3$-$C_6$) cycloalkylaminosulfonyl, {($C_3$-$C_6$)cycloalkyl}{($C_1$-$C_6$)alkyl}aminosulfonyl, di($C_3$-$C_6$) cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$) alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl;

Y is ($C_1$-$C_6$)alkyl or halo($C_1$-$C_6$)alkyl;

n is 0, 1 or 2;

E is (a) a bond or (b) ($C_1$-$C_3$)alkylene or ($C_1$-$C_2$)alkylenyloxy, wherein the 0 is attached to $R^2$, each of which is optionally substituted with 1 to 4 groups independently selected from methyl, ethyl, trifluoromethyl and oxo;

$R^2$ is ($C_2$-$C_6$)alkyl, aryl, heteroaryl, cycloalkyl or heterocyclyl, each of which is optionally substituted with up to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$) alkenyl, ($C_2$-$C_6$)alkynyl, ($C_3$-$C_6$)cycloalkyl($C_2$-$C_4$) alkynyl, halo($C_1$-$C_6$)alkyl, halo($C_3$-$C_6$)cycloalkyl, halo ($C_4$-$C_7$)cycloalkylalkyl, ($C_1$-$C_6$)alkoxy, ($C_3$-$C_6$) cycloalkoxy, ($C_4$-$C_7$)cycloalkylalkoxy, halo($C_1$-$C_6$) alkoxy, halo($C_3$-$C_6$)cycloalkoxy, halo($C_4$-$C_7$) cycloalkylalkoxy, ($C_1$-$C_6$)alkylthio, ($C_3$-$C_6$) cycloalkylhio, ($C_4$-$C_7$)cycloalkylalkylthio, halo($C_1$-$C_6$) alkylthio, halo($C_3$-$C_6$)cycloalkylhio, halo($C_4$-$C_7$) cycloalkylalkylthio, ($C_1$-$C_6$)alkanesulfinyl, ($C_3$-$C_6$) cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$) alkanesulfonyl, ($C_3$-$C_6$)cycloalkanesulfonyl, ($C_4$-$C_7$) cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$) alkylamino, ($C_1$-$C_6$)alkoxy($C_1$-$C_6$)alkoxy, halo($C_1$-$C_6$) alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy ($C_1$-$C_6$)alkyl, halo($C_1$-$C_6$)alkoxy($C_1$-$C_6$)alkyl, hydroxy ($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino ($C_1$-$C_6$)alkylamino($C_2$-$C_6$)alkoxy, ($C_1$-$C_6$)alkylamino ($C_2$-$C_6$)alkoxy, di($C_1$-$C_6$)alkylamino($C_2$-$C_6$)alkoxy, ($C_1$-$C_6$)alkylcarbonyl, ($C_3$-$C_6$)cycloalkylcarbonyl, ($C_3$-$C_6$)cycloalkylaminocarbonyl, {($C_3$-$C_6$)cycloalkyl}{ ($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$) cycloalkyl}{($C_1$-$C_6$)alkyl}aminosulfonyl, di($C_3$-$C_6$) cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$) alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl;

$R^3$ is selected from ($C_2$-$C_6$)alkyl, ($C_2$-$C_6$)alkenyl, ($C_2$-$C_6$) alkynyl, ($C_3$-$C_5$)cycloalkyl($C_1$-$C_4$)alkyl, ($C_1$-$C_3$)alkoxy ($C_1$-$C_3$)alkoxy, and ($C_1$-$C_3$)alkoxy($C_1$-$C_3$)alkyl, each of which is optionally substituted with up to four groups independently selected from fluorine, cyano, oxo, $R^4$, $R^4O-$, $(R^4)_2N-$, $R^4O_2C-$, $R^4S$, $R^4S(=O)-$, $R^4S(=O)_2-$, $R^4C(=O)NR^4-$, $(R^4)_2NC(=O)-$, $(R^4)_2NC(=O)O-$, $(R^4)_2NC(=O)NR^4-$, $R^4OC(=O)NR^4-$, $(R^4)_2NC(=NCN)NR^4-$, $(R^4O)_2P(=O)O-$, $(R^4O)_2P(=O)NR^4-$, $R^4OS(=O)_2NR^4-$, $(R^4)_2NS(=O)_2O-$, $(R^4)_2NS(=O)_2NR^4-$, $R^4S(=O)_2NR^4-$, $R^4S(=O)_2NHC(=O)-$, $R^4S(=O)_2NHC(=O)O-$, $R^4S(=O)_2NHC(=O)NR^4-$, $R^4OS(=O)_2NHC(=O)-$, $R^4OS(=O)_2NHC(=O)O-$, $R^4OS(=O)_2NHC(=O)NR^4-$, $(R^4)_2NS(=O)_2NHC(=O)-$, $(R^4)_2NS(=O)_2NHC(=O)O-$, $(R^4)_2NS(=O)_2NHC(=O)NR^4-$, $R^4C(=O)NHS(=O)_2-$, $R^4C(=O)NHS(=O)_2O-$, $R^4C(=O)NHS(=O)_2NR^4-$, $R^4OC(=O)NHS(=O)_2-$, $R^4OC(=O)NHS(=O)_2O-$, $R^4OC(=O)NHS(=O)_2NR^4-$, $(R^4)_2NC(=O)NHS(=O)_2-$, $(R^4)_2NC(=O)NHS(=O)_2O-$, $(R^4)_2NC(=O)NHS(=O)_2NR^4-$, spirocycloalkyl; heterocyclyl (which in turn may be optionally substituted with alkyl, haloalkyl, halogen or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo); and $R^4$ is independently selected from H, ($C_1$-$C_6$)alkyl, halo ($C_1$-$C_6$)alkyl, amino($C_1$-$C_6$)alkyl, ($C_1$-$C_6$)alkylamino ($C_1$-$C_6$)alkyl, di($C_1$-$C_6$)alkylamino($C_1$-$C_6$)alkyl, hydroxy($C_1$-$C_6$)alkyl and ($C_1$-$C_6$)alkoxy($C_1$-$C_6$)alkyl;

or a pharmaceutically acceptable salt, enantiomer or diastereomer thereof.

2. The compound of claim 1, wherein:

$R^1$ is (a) absent or (b) is selected from ($C_1$-$C_6$)alkyl, ($C_2$-$C_6$)alkenyl, ($C_2$-$C_6$)alkynyl and ($C_1$-$C_3$)alkoxy($C_1$-$C_3$) alkyl, each of which is optionally substituted with up to four groups independently selected from fluorine, cyano, oxo, $R^4$, $R^4O-$, $(R^4)_2N-$, $R^4O_2C-$, $R^4S$, $R^4S(=O)-$, $R^4S(=O)_2-$, $R^4C(=O)NR^4-$, $(R^4)_2NC(=O)-$, $(R^4)_2NC(=O)O-$, $(R^4)_2NC(=O)NR^4-$, $R^4OC(=O)NR^4-$, $(R^4)_2NC(=NCN)NR^4-$, $(R^4O)_2P(=O)O-$, $(R^4O)_2P(=O)NR^4-$, $R^4OS(=O)_2NR^4-$, $(R^4)_2NS(=O)_2O-$, $(R^4)_2NS(=O)_2NR^4-$, $R^4S(=O)_2NR^4-$, $R^4S(=O)_2NHC(=O)-$, $R^4S(=O)_2NHC(=O)O-$, $R^4S(=O)_2NHC(=O)NR^4-$, $R^4OS(=O)_2NHC(=O)-$, $R^4OS(=O)_2NHC(=O)O-$, $R^4OS(=O)_2NHC(=O)NR^4-$, $(R^4)_2NS(=O)_2NHC(=O)-$, $(R^4)_2NS(=O)_2NHC(=O)O-$, $(R^4)_2NS(=O)_2NHC(=O)NR^4-$, $R^4C(=O)NHS(=O)_2-$, $R^4C(=O)NHS(=O)_2O-$, $R^4C(=O)NHS(=O)_2$ NR$^4$—, R$^4$OC(=O)NHS(=O)$_2$—, R$^4$OC(=O)NHS(=O)$_2$O—, R$^4$OC(=O)NHS(=O)$_2$NR$^4$—, (R$^4$)$_2$NC(=O)NHS(=O)$_2$—, (R$^4$)$_2$NC(=O)NHS(=O)$_2$O—, (R$^4$)$_2$NC(=O)NHS(=O)$_2$NR$^4$—, aryl, cycloalkyl, heterocyclyl, heteroaryl, arylamino and heteroarylamino;

A$^1$ is (a) a bond, or (b) (C$_1$-C$_3$)alkylene, CH$_2$CH$_2$O, wherein the oxygen is attached to Cy$^1$, or CH$_2$C(=O), wherein the carbonyl carbon is attached to Cy$^1$;

Cy$^1$ is aryl, heteroaryl, monocyclic cycloalkyl or heterocyclyl, each of which is optionally substituted with 1 to 4 groups independently selected from fluorine, chlorine, bromine, iodine, cyano, nitro, amino, hydroxy, carboxy, (C$_1$-C$_6$)alkyl, hydroxy(C$_1$-C$_6$)alkyl, (C$_3$-C$_6$)cycloalkyl, hydroxy(C$_3$-C$_6$)cycloalkyl, (C$_4$-C$_7$)cycloalkylalkyl, (C$_2$-C$_6$)alkenyl, halo(C$_2$-C$_6$)alkenyl, hydroxy(C$_2$-C$_6$)alkenyl, (C$_2$-C$_6$)alkynyl, (C$_3$-C$_6$)cycloalkyl(C$_2$-C$_4$)alkynyl, halo(C$_1$-C$_6$)alkyl, halo(C$_3$-C$_6$)cycloalkyl, halo(C$_4$-C$_7$)cycloalkylalkyl, (C$_1$-C$_6$)alkoxy, (C$_3$-C$_6$)cycloalkoxy, (C$_4$-C$_7$)cycloalkylalkoxy, halo(C$_1$-C$_6$)alkoxy, halo(C$_3$-C$_6$)cycloalkoxy, halo(C$_4$-C$_7$)cycloalkylalkoxy, (C$_1$-C$_6$)alkylthio, (C$_3$-C$_6$)cycloalkylhio, (C$_4$-C$_7$)cycloalkylalkylthio, halo(C$_1$-C$_6$)alkylthio, halo(C$_3$-C$_6$)cycloalkylhio, halo(C$_4$-C$_7$)cycloalkylalkylthio, (C$_1$-C$_6$)alkanesulfinyl, (C$_3$-C$_6$)cycloalkanesulfinyl, (C$_4$-C$_7$)cycloalkylalkanesulfinyl, halo(C$_1$-C$_6$)alkane-sulfinyl, halo(C$_3$-C$_6$)cycloalkanesulfinyl, halo(C$_4$-C$_7$)cycloalkylalkanesulfinyl, (C$_1$-C$_6$)alkanesulfonyl, (C$_3$-C$_6$)cycloalkanesulfonyl, (C$_4$-C$_7$)cycloalkylalkanesulfonyl, halo(C$_1$-C$_6$)alkanesulfonyl, halo(C$_3$-C$_6$)cycloalkanesulfonyl, halo(C$_4$-C$_7$)cycloalkylalkanesulfonyl, (C$_1$-C$_6$)alkylamino, di(C$_1$-C$_6$)alkylamino, (C$_1$-C$_6$)alkoxy(C$_1$-C$_6$)alkoxy, halo(C$_1$-C$_6$)alkoxy(C$_1$-C$_6$)alkoxy, (C$_1$-C$_6$)alkoxycarbonyl, H$_2$NCO, H$_2$NSO$_2$, (C$_1$-C$_6$)alkylaminocarbonyl, di(C$_1$-C$_6$)alkylaminocarbonyl, (C$_1$-C$_3$)alkoxy(C$_1$-C$_3$)alkylaminocarbonyl, heterocyclylcarbonyl, (C$_1$-C$_6$)alkylaminosulfonyl, di(C$_1$-C$_6$)alkylaminosulfonyl, heterocyclsulfonyl, (C$_1$-C$_6$)alkylcarbonylamino, (C$_1$-C$_6$)alkylcarbonylamino(C$_1$-C$_6$)alkyl, (C$_1$-C$_6$)alkylsulfonylamino, (C$_1$-C$_6$)alkylsulfonylamino(C$_1$-C$_6$)alkyl, (C$_1$-C$_6$)alkoxycarbonyl(C$_1$-C$_6$)alkoxy, (C$_1$-C$_6$)alkoxy(C$_1$-C$_6$)alkyl, halo(C$_1$-C$_6$)alkoxy(C$_1$-C$_6$)alkyl, hydroxy(C$_1$-C$_6$)alkoxy, heteroaryl, oxo, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkyl, (C$_1$-C$_6$)alkylamino(C$_2$-C$_6$)alkoxy, (C$_1$-C$_6$)alkylamino(C$_2$-C$_6$)alkoxy, di(C$_1$-C$_6$)alkylamino(C$_2$-C$_6$)alkoxy and (C$_1$-C$_6$)alkylcarbonyl;

A$^2$ is (a) a bond, O, S or NR$^4$; or (b) (C$_1$-C$_3$)alkylene or (C$_1$-C$_2$)alkyleneoxy, each of which is optionally substituted with 1 to 4 groups independently selected from methyl, ethyl, trifluoromethyl and oxo;

Cy$^2$ is aryl, cycloalkyl, a heteroaryl selected from 2- or 3-thienyl, 2- or 3-furanyl, 2- or 3-pyrrolyl, 2-,3-, or 4-pyridyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, 5-, 6-, 7- or 8-quinazolinyl, 2-, 3-, 5-, 6-, 7- or 8-quinoxalinyl, 2-, 3-, 4-, 5-, 6-, 7- or 8-quinolinyl, 1-, 3-, 4-, 5-, 6-, 7- or 8-isoquinolinyl, 2-, 4-, or 5-thiazolyl, 2-, 3-, 4-, and 5-imidazolyl, or a heterocyclyl selected from pyrrolidine, pyrrolidin-2-one, 1-methylpyrrolidin-2-one, piperidine, piperidin-2-one, 2-pyridone, 4-pyridone, 1-(2,2,2-trifluoroethyl)piperazine, piperazin-2-one, 5,6-dihydropyrimidin-4-one, pyrimidin-4-one, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide and isothiazolidine 1,1-dioxide, wherein the aryl, cycloalkyl or heterocyclyl represented by Cy$^2$, is optionally substituted with 1 to 4 groups independently selected from fluorine, chlorine, bromine, iodine, cyano, nitro, amino, hydroxy, carboxy, (C$_1$-C$_6$)alkyl, hydroxy(C$_1$-C$_6$)alkyl, (C$_3$-C$_6$)cycloalkyl, hydroxy(C$_3$-C$_6$)cycloalkyl, (C$_4$-C$_7$)cycloalkylalkyl, (C$_2$-C$_6$)alkenyl, halo(C$_2$-C$_6$)alkenyl, hydroxy(C$_2$-C$_6$)alkenyl, (C$_2$-C$_6$)alkynyl, (C$_3$-C$_6$)cycloalkyl(C$_2$-C$_4$)alkynyl, halo(C$_1$-C$_6$)alkyl, halo(C$_3$-C$_6$)cycloalkyl, halo(C$_4$-C$_7$)cycloalkylalkyl, (C$_1$-C$_6$)alkoxy, (C$_3$-C$_6$)cycloalkoxy, (C$_4$-C$_7$)cycloalkylalkoxy, halo(C$_1$-C$_6$)alkoxy, halo(C$_3$-C$_6$)cycloalkoxy, halo(C$_4$-C$_7$)cycloalkylalkoxy, (C$_1$-C$_6$)alkylthio, (C$_3$-C$_6$)cycloalkylhio, (C$_4$-C$_7$)cycloalkylalkylthio, halo(C$_1$-C$_6$)alkylthio, halo(C$_3$-C$_6$)cycloalkylhio, halo(C$_4$-C$_7$)cycloalkylalkylthio, (C$_1$-C$_6$)alkanesulfinyl, (C$_3$-C$_6$)cycloalkanesulfinyl, (C$_4$-C$_7$)cycloalkylalkanesulfinyl, halo(C$_1$-C$_6$)alkane-sulfinyl, halo(C$_3$-C$_6$)cycloalkanesulfinyl, halo(C$_4$-C$_7$)cycloalkylalkanesulfinyl, (C$_1$-C$_6$)alkanesulfonyl, (C$_3$-C$_6$)cycloalkanesulfonyl, (C$_4$-C$_7$)cycloalkylalkanesulfonyl, halo(C$_1$-C$_6$)alkanesulfonyl, halo(C$_3$-C$_6$)cycloalkanesulfonyl, halo(C$_4$-C$_7$)cyclo-alkylalkanesulfonyl, (C$_1$-C$_6$)alkylamino, di(C$_1$-C$_6$)alkylamino, (C$_1$-C$_6$)alkoxy(C$_1$-C$_6$)alkoxy, halo(C$_1$-C$_6$)alkoxy(C$_1$-C$_6$)alkoxy, (C$_1$-C$_6$)alkoxycarbonyl, H$_2$NCO, H$_2$NSO$_2$, (C$_1$-C$_6$)alkylaminocarbonyl, di(C$_1$-C$_6$)alkylaminocarbonyl, (C$_1$-C$_3$)alkoxy(C$_1$-C$_3$)alkylaminocarbonyl, heterocyclylcarbonyl, (C$_1$-C$_6$)alkylaminosulfonyl, di(C$_1$-C$_6$)alkylaminosulfonyl, heterocyclsulfonyl, (C$_1$-C$_6$)alkylcarbonylamino, (C$_1$-C$_6$)alkylcarbonylamino(C$_1$-C$_6$)alkyl, (C$_1$-C$_6$)alkylsulfonylamino, (C$_1$-C$_6$)alkylsulfonylamino(C$_1$-C$_6$)alkyl, (C$_1$-C$_6$)alkoxycarbonyl(C$_1$-C$_6$)alkoxy, (C$_1$-C$_6$)alkoxy(C$_1$-C$_6$)alkyl, halo(C$_1$-C$_6$)alkoxy(C$_1$-C$_6$)alkyl, hydroxy(C$_1$-C$_6$)alkoxy, heteroaryl, oxo, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkyl, (C$_1$-C$_6$)alkylamino(C$_2$-C$_6$)alkoxy, (C$_1$-C$_6$)alkylamino(C$_2$-C$_6$)alkoxy, di(C$_1$-C$_6$)alkylamino(C$_2$-C$_6$)alkoxy and (C$_1$-C$_6$)alkylcarbonyl;

Y is (C$_1$-C$_6$)alkyl or halo(C$_1$-C$_6$)alkyl;

n is 0, 1 or 2;

E is (a) a bond or (b) (C$_1$-C$_3$)alkylene or (C$_1$-C$_2$)alkylenyloxy, wherein the O is attached to R$^2$, each of which is optionally substituted with 1 to 4 groups independently selected from methyl, ethyl, trifluoromethyl and oxo;

R$^2$ is (C$_2$-C$_6$)alkyl, aryl, heteroaryl, cycloalkyl or heterocyclyl, each of which is optionally substituted with up to 4 groups independently selected from fluorine, chlorine, bromine, iodine, cyano, nitro, amino, hydroxy, carboxy, (C$_1$-C$_6$)alkyl, hydroxy(C$_1$-C$_6$)alkyl, (C$_3$-C$_6$)cycloalkyl, hydroxy(C$_3$-C$_6$)cycloalkyl, (C$_4$-C$_7$)cycloalkylalkyl, (C$_2$-C$_6$)alkenyl, halo(C$_2$-C$_6$)alkenyl, hydroxy(C$_2$-C$_6$)alkenyl, (C$_2$-C$_6$)alkynyl, (C$_3$-C$_6$)cycloalkyl(C$_2$-C$_4$)alkynyl, halo(C$_1$-C$_6$)alkyl, halo(C$_3$-C$_6$)cycloalkyl, halo(C$_4$-C$_7$)cycloalkylalkyl, (C$_1$-C$_6$)alkoxy, (C$_3$-C$_6$)cycloalkoxy, (C$_4$-C$_7$)cycloalkylalkoxy, halo(C$_1$-C$_6$)alkoxy, halo(C$_3$-C$_6$)cycloalkoxy, halo(C$_4$-C$_7$)cycloalkylalkoxy, (C$_1$-C$_6$)alkylthio, (C$_3$-C$_6$)cycloalkylhio, (C$_4$-C$_7$)cycloalkylalkylthio, halo(C$_1$-C$_6$)

alkylthio, halo(C₃-C₆)cycloalkylthio, halo(C₄-C₇)cycloalkylalkylthio, (C₁-C₆)alkanesulfinyl, (C₃-C₆)cycloalkanesulfinyl, (C₄-C₇)cycloalkylalkanesulfinyl, halo(C₁-C₆)alkane-sulfinyl, halo(C₃-C₆)cycloalkanesulfinyl, halo(C₄-C₇)cycloalkylalkanesulfinyl, (C₁-C₆) alkanesulfonyl, (C₃-C₆)cycloalkanesulfonyl, (C₄-C₇) cycloalkylalkanesulfonyl, halo(C₁-C₆)alkanesulfonyl, halo(C₃-C₆)cycloalkanesulfonyl, halo(C₄-C₇)cycloalkylalkanesulfonyl, (C₁-C₆)alkylamino, di(C₁-C₆) alkylamino, (C₁-C₆)alkoxy(C₁-C₆)alkoxy, halo(C₁-C₆) alkoxy(C₁-C₆)alkoxy, (C₁-C₆)alkoxycarbonyl, H₂NCO, H₂NSO₂, (C₁-C₆)alkylaminocarbonyl, di(C₁-C₆) alkylaminocarbonyl, (C₁-C₃)alkoxy(C₁-C₃)alkylaminocarbonyl, heterocyclylcarbonyl, (C₁-C₆)alkylaminosulfonyl, di(C₁-C₆)alkylaminosulfonyl, heterocyclsulfonyl, (C₁-C₆)alkylcarbonylamino, (C₁-C₆)alkylcarbonylamino(C₁-C₆)alkyl, (C₁-C₆)alkylsulfonylamino, (C₁-C₆)alkylsulfonylamino(C₁-C₆)alkyl, (C₁-C₆) alkoxycarbonyl(C₁-C₆)alkoxy, (C₁-C₆)alkoxy(C₁-C₆) alkyl, halo(C₁-C₆)alkoxy(C₁-C₆)alkyl, hydroxy(C₁-C₆) alkoxy, heteroaryl, oxo, amino(C₁-C₆)alkyl, (C₁-C₆) alkylamino(C₁-C₆)alkyl, di(C₁-C₆)alkylamino(C₁-C₆) alkylamino(C₂-C₆)alkoxy, (C₁-C₆)alkylamino(C₂-C₆) alkoxy, di(C₁-C₆)alkylamino(C₂-C₆)alkoxy and (C₁-C₆)alkylcarbonyl;

R³ is selected from (C₂-C₆)alkyl, (C₂-C₆)alkenyl, (C₂-C₆) alkynyl and (C₁-C₃)alkoxy(C₁-C₃)alkyl, each of which is optionally substituted with up to four groups independently selected from fluorine, cyano, oxo, R⁴, R⁴O—, (R⁴)₂N—, R⁴O₂C—, R⁴S, R⁴S(═O)—, R⁴S(═O)₂—, R⁴C(═O)NR⁴, (R⁴)₂NC(═O)—, (R⁴)₂NC(═O)O—, (R⁴)₂NC(═O)NR⁴—, R⁴OC(═O)NR⁴—, (R⁴)₂NC (═NCN)NR⁴, (R⁴O)₂P(═O)O—, (R⁴O)₂P(═O) NR⁴—, R⁴OS(═O)₂NR⁴—, (R⁴)₂NS(═O)₂O—, (R⁴)₂NS(═O)₂NR⁴, R⁴S(═O)₂NR⁴—, R⁴S(═O)₂ NHC(═O)—, R⁴S(═O)₂NHC(═O)O—, R⁴S(═O)₂ NHC(═O)NR⁴, R⁴OS(═O)₂NHC(═O)—, R⁴OS (═O)₂NHC(═O)O—, R⁴OS(═O)₂NHC(═O)NR⁴, (R⁴)₂NS(═O)₂NHC(═O)—, (R⁴)₂NS(═O)₂NHC (═O)O—, (R⁴)₂NS(═O)₂NHC(═O)NR⁴, R⁴C(═O) NHS(═O)₂—, R⁴C(═O)NHS(═O)₂O—, R⁴C(═O) NHS(═O)₂NR⁴, R⁴OC(═O)NHS(═O)₂—, R⁴OC (═O)NHS(═O)₂O—, R⁴OC(═O)NHS(═O)₂NR⁴, (R⁴)₂NC(═O)NHS(═O)₂—, (R⁴)₂NC(═O)NHS (═O)₂O—, (R⁴)₂NC(═O)NHS(═O)₂NR⁴, heterocyclyl (which in turn may be optionally substituted with alkyl, haloalkyl or oxo), heteroaryl (which in turn may be optionally substituted with alkyl, haloalkyl, alkoxy, alkylthio, alkylsulfonyl, halogen, trifluoromethyl, dialkylamino, nitro, cyano, CO₂H, CONH₂, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, CO₂H, CONH₂, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, CO₂H, CONH₂, N-monoalkyl-substituted amido, N,N-dialkyl-substituted amido, or oxo); and R⁴ is independently selected from H, (C₁-C₆)alkyl, halo (C₁-C₆)alkyl, amino(C₁-C₆)alkyl, (C₁-C₆)alkylamino (C₁-C₆)alkyl, di(C₁-C₆)alkylamino(C₁-C₆)alkyl, hydroxy(C₁-C₆)alkyl and (C₁-C₆)alkoxy(C₁-C₆)alkyl;

or a pharmaceutically acceptable salt, enantiomer or diastereomer thereof.

3. A compound of Formula (I):

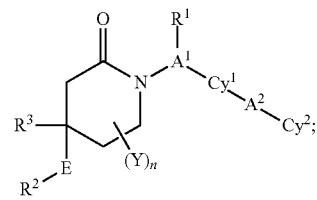

wherein:
R¹ is absent or is methyl or ethyl;
A¹ is a bond or CH₂ or if R¹ is present, then A¹ is CH;
Cy¹ is phenyl, cyclopropyl, cyclohexyl, pyrrolidinyl, pyridyl, N-oxo-pyridyl, thiazolyl or pyrimidinyl each of which is optionally substituted with 1 to 4 groups independently selected from halo, methyl, trifluoromethyl, hydroxy, methoxy, methoxycarbonyl, carboxy, ethoxycarbonylmethoxy 2-hydroxy-2-methylpropoxy, cyano, difluoromethoxy, t-butoxycarbonyl, hydroxy, hydroxymethyl, 2-hydroxyethyl, 2-hydroxy-2-propyl, methoxymethyl, methylsulfonyl and methylsulfonylamino;
A² is a bond, O, OCH₂CO or C═O;
Cy² is phenyl, thienyl, pyridyl, N-oxo-pyridyl, cyclopropyl, piperidinyl, morpholinyl, thiazolyl, oxadiazolyl, thiadiazolyl, S,S-dioxothiazinyl, 2-oxo-1,2-dihydropyridyl each of which is optionally substituted by 1 to 4 groups independently selected from aminomethyl, 1-aminoethyl, halo, hydroxy, methoxy, hydroxymethyl, methoxycarbonyl, amino, carbamoyl, methylcarbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethylaminosulfonyl, pyrrolidine-1-sulfonyl, methylsulfonylaminomethyl, tetrazolyl, methyl, trifluoromethyl, acetyl, 2-hydroxyethyl and 1-aminoethyl;
Y is (C₁-C₆)alkyl or halo(C₁-C₆)alkyl;
n is 0;
E is a bond or CH₂;
R² is cyclohexyl, isopropyl, thienyl, phenyl or pyridyl, each of which is optionally substituted with one group selected from halo, methyl, methylthio and (4-morpholino)methyl; and
R³ is methyl, ethyl, propyl, butyl, vinyl, allyl or ethoxyethyl, each of which is optionally substituted with up to two groups independently selected from methyl, H₂C═CH, HO—, MeO—, MeC(═O), H₂N—, MeC (═O)NH—, MeS(═O)₂NH—, H₂NC(═O)—, MeNHC(═O)—, HO₂C—, HO—(CH₂)₂O—, (HO)₂P (═O)O—, H₂NS(═O)₂O—, H₂NS(═O)₂NH—, MeNHC(═O)NH—, MeNHC(═O)O—, cyano, HO₂C—, HOCH₂CH₂NH—, 4-morpholino, HOCH₂C (═O)NH—, H₂NCH₂C(═O)NH—, EtNHC(═O)NH, H₂NHC(═O)NH, H₂NHC(═O)O—, CH₃C(═O)—, MeOC(═O)NH—, MeNHC(═NCN)NH—, Me-, MeS—, MeSO₂— MeSO₂N(Me)—, MeS(═O)₂NHC (═O)—, imidazolylamino-, imidazolyl, morpholino, tetrazolyl, H₂NCONH—, H₂NCO₂—, HOCH₂CH₂O—, MeNH—, Me₂N— and MeCONMe;
or a pharmaceutically acceptable salt, enantiomer or diastereomer thereof.

4. The compound of claim 2, wherein the compound is of Formula (Ia):

Ia wherein;

r is 0, 1, 2, 3 or 4; and

G is independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkyl, $(C_1-C_6)$alkylamino$(C_2-C_6)$alkoxy, $(C_1-C_6)$alkylamino$(C_2-C_6)$alkoxy, di$(C_1-C_6)$alkylamino$(C_2-C_6)$alkoxy and $(C_1-C_6)$alkylcarbonyl;

or a pharmaceutically acceptable salt, enantiomer or diastereomer thereof.

5. The compound of claim 2, wherein the compound is of Formula (Ib):

Ib or a pharmaceutically acceptable salt, enantiomer or diastereomer thereof.

6. The compound of claim 2, wherein the compound is of Formula (Ic):

Ic or a pharmaceutically acceptable salt, enantiomer or diastereomer thereof.

7. The compound of claim 2, wherein the compound is of Formula (Id):

Id wherein:

m is 0, 1, 2, 3 or 4; and

X is independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylhio, $(C_4-C_7)$cycloalkylalkylthio, halo$(C_1-C_6)$alkylthio, halo$(C_3-C_6)$cycloalkylhio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkane-sulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylamino-sulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy ($C_1$-$C_6$)alkyl, halo($C_1$-$C_6$)alkoxy($C_1$-$C_6$)alkyl, hydroxy ($C_1$-$C_6$)alkoxy, heteroaryl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy and ($C_1$-$C_6$)alkylcarbonyl;

or a pharmaceutically acceptable salt, enantiomer or diastereomer thereof.

8. The compound of claim 2, wherein the compound is of Formula (Ie):

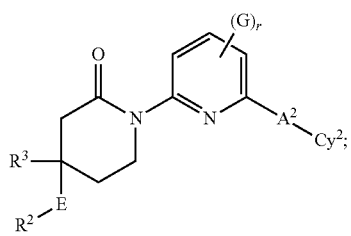

wherein:

r is 0, 1, 2, 3 or 4; and

G is independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylhio, ($C_4$-$C_7$)cycloalkylalkylthio, halo($C_1$-$C_6$)alkylthio, halo($C_3$-$C_6$)cycloalkylhio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkane-sulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkyl-aminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy and ($C_1$-$C_6$)alkylcarbonyl;

or a pharmaceutically acceptable salt, enantiomer or diastereomer thereof.

9. The compound of claim 2, wherein the compound is of Formula (If):

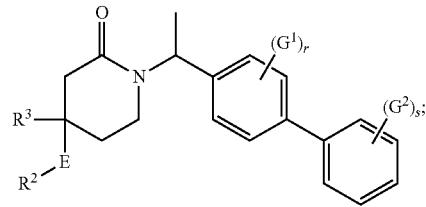

wherein:

r and s are independently 0, 1, 2, 3 or 4; and $G^1$ and $G^2$ are independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkylhio, ($C_4$-$C_7$)cycloalkylalkylthio, halo($C_1$-$C_6$)alkylthio, halo($C_3$-$C_6$)cycloalkylhio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkyl-aminocarbonyl, heterocyclylcarbonyl, ($C_1$-$C_6$)alkylaminosulfonyl, di($C_1$-$C_6$)alkylaminosulfonyl, heterocyclsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy and ($C_1$-$C_6$)alkylcarbonyl;

or a pharmaceutically acceptable salt, enantiomer or diastereomer thereof.

10. The compound of claim 2, wherein the compound is of Formula (If*):

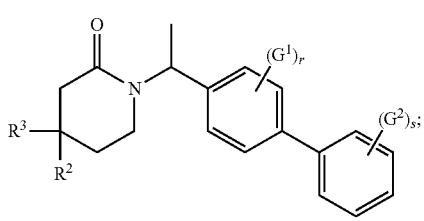

wherein:

r and s are independently 0, 1, 2, 3 or 4; and $G^1$ and $G^2$ are independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkyl-aminocarbonyl, heterocyclylcarbonyl, $(C_1-C_6)$alkylaminosulfonyl, di$(C_1-C_6)$alkylaminosulfonyl, heterocyclsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy and $(C_1-C_6)$alkylcarbonyl;

or a pharmaceutically acceptable salt, enantiomer or diastereomer thereof.

11. A pharmaceutical composition comprising: i) a pharmaceutically acceptable carrier or diluent; and ii) the compound of claim 1; or a pharmaceutically acceptable salt, enantiomer or diastereomer thereof.

12. The compound of claim 2, wherein the compound is represented by the following structural formula:

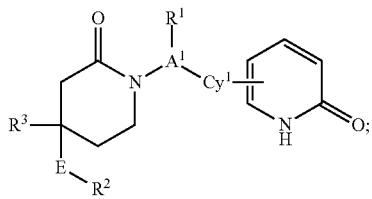

or a pharmaceutically acceptable salt, enantiomer or diastereomer thereof, wherein the oxodihydropyridyl group is optionally substituted with one to four substituents selected from 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkylthio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonyl-amino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkylamino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, {$(C_3-C_6)$cycloalkyl}{$(C_1-C_6)$alkyl}aminocarbonyl, di$(C_3-C_6)$cycloalkylaminocarbonyl, $(C_3-C_6)$cycloalkylaminosulfonyl, {$(C_3-C_6)$cycloalkyl}{$(C_1-C_6)$alkyl}aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, {$(C_3-C_6)$cycloalkyl}{$(C_1-C_6)$alkyl}aminocarbonyl$(C_1-C_6)$alkyl and di$(C_3-C_6)$cycloalkylaminocarbonyl$(C_1-C_6)$alkyl.

13. The compound of claim 2, wherein the compound is represented by a structural formula selected from:

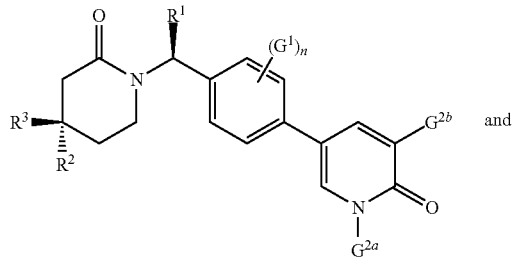

and

-continued

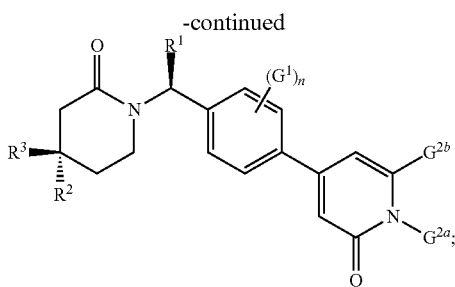

or a pharmaceutically acceptable salt, enantiomer or diastereomer thereof, wherein:

$G^1$ is $(C_1-C_4)$alkyl, $(C_1-C_4)$alkoxy, $(C_1-C_4)$haloalkyl, $(C_1-C_4)$haloalkoxy, halogen, cyano or nitro;

n is 0, 1 or 2; and $G^{2a}$ is $(C_1-C_4)$alkyl, $(C_3-C_4)$cycloalkyl or $(C_1-C_4)$haloalkyl; and $G^{2b}$ is hydrogen, fluorine, chlorine, cyano, hydroxy, amino, $(C_1-C_4)$alkyl, $(C_3-C_4)$cycloalkyl, $(C_3-C_4)$cycloalkyl $(C_1-C_2)$alkyl, halo$(C_1-C_4)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl or $(C_1-C_4)$alkylcarbonylamino.

14. The compound of claim 13, wherein:
$R^1$ is methyl or ethyl;
$R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and
$R^3$ is $H_2NC(=O)CMe_2CH_2$, 3-hydroxy-3-methylbutyl, 2-hydroxy-2-methylpropyl or 2-cyano-2-methylpropyl.

15. The compound of claim 1, wherein the compound is selected from:
(R)-1-((S)-1-(4'-fluorobiphenyl-4-yl)ethyl)-4-(2-hydroxyethyl)-4-phenylpiperidin-2-one;
5-(4-((S)-1-((S)-4-(4-fluorophenyl)-4-(3-hydroxypropyl)-2-oxopiperidin-1-yl)ethyl)phenyl)-1-methylpyridin-2(1H)-one;
4-(4-((S)-1-((R)-4-(2-hydroxy-2-methylpropyl)-2-oxo-4-phenylpiperidin-1-yl)ethyl)phenyl)-1-methylpyridin-2(1H)-one;
5-(4-((S)-1-((R)-4-(2-hydroxy-2-methylpropyl)-2-oxo-4-phenylpiperidin-1-yl)ethyl)phenyl)-1-methylpyridin-2(1H)-one;
4-(4-((S)-1-((R)-4-(2-hydroxy-2-methylpropyl)-2-oxo-4-phenylpiperidin-1-yl)ethyl)phenyl)pyridin-2(1H)-one; and
5-(4-((S)-1-((R)-4-(2-hydroxy-2-methylpropyl)-2-oxo-4-phenylpiperidin-1-yl)ethyl)phenyl)pyridin-2(1H)-one;
or a pharmaceutically acceptable salt thereof.

* * * * *